(12) United States Patent
Funahashi

(10) Patent No.: US 8,709,613 B2
(45) Date of Patent: *Apr. 29, 2014

(54) AROMATIC AMINE DERIVATIVE, ORGANIC ELECTROLUMINESCENT ELEMENT EMPLOYING THE SAME, AND PROCESS FOR PRODUCING AROMATIC AMINE DERIVATIVE

(75) Inventor: Masakazu Funahashi, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 1392 days.

This patent is subject to a terminal disclaimer.

(21) Appl. No.: 11/596,299

(22) PCT Filed: Sep. 17, 2004

(86) PCT No.: PCT/JP2004/014020
§ 371 (c)(1),
(2), (4) Date: Nov. 13, 2006

(87) PCT Pub. No.: WO2005/108348
PCT Pub. Date: Nov. 17, 2005

(65) Prior Publication Data
US 2007/0252511 A1 Nov. 1, 2007

(30) Foreign Application Priority Data

May 12, 2004 (JP) ................. 2004-141900

(51) Int. Cl.
*H01L 51/50* (2006.01)
*C07C 211/54* (2006.01)
*B32B 9/04* (2006.01)

(52) U.S. Cl.
USPC ........... 428/690; 428/917; 313/504; 313/506; 564/426

(58) Field of Classification Search
None
See application file for complete search history.

(56) References Cited

U.S. PATENT DOCUMENTS

| | | | |
|---|---|---|---|
| 4,233,384 A | 11/1980 | Turner et al. | |
| 5,153,073 A | 10/1992 | Ohnuma et al. | |
| 7,651,786 B2 * | 1/2010 | Matsuura et al. | 428/690 |
| 7,705,183 B2 * | 4/2010 | Funahashi et al. | 564/308 |
| 7,981,523 B2 * | 7/2011 | Hosokawa et al. | 428/690 |
| 2003/0118866 A1 * | 6/2003 | Oh et al. | 428/690 |
| 2004/0053069 A1 * | 3/2004 | Sotoyama et al. | 428/690 |
| 2004/0137270 A1 | 7/2004 | Seo et al. | |
| 2005/0038296 A1 | 2/2005 | Hosokawa et al. | |
| 2005/0064233 A1 * | 3/2005 | Matsuura et al. | 428/690 |
| 2006/0033421 A1 | 2/2006 | Matsuura et al. | |
| 2006/0152146 A1 | 7/2006 | Funahashi | |
| 2006/0189828 A1 | 8/2006 | Hosokawa et al. | |
| 2006/0194074 A1 | 8/2006 | Funahashi | |
| 2006/0210830 A1 | 9/2006 | Funahashi et al. | |
| 2006/0251925 A1 | 11/2006 | Hosokawa et al. | |
| 2007/0009758 A1 | 1/2007 | Funahashi | |
| 2007/0252511 A1 | 11/2007 | Funahashi | |

FOREIGN PATENT DOCUMENTS

| | | |
|---|---|---|
| DE | 10002561 | 7/2001 |
| DE | 19963009 | 8/2001 |
| EP | 1 403 354 A | 3/2004 |
| EP | 1 604 974 A | 12/2005 |
| EP | 1 737 277 A | 12/2006 |
| EP | 1 746 080 A1 | 1/2007 |
| JP | 61 129648 | 6/1986 |
| JP | 4-118658 | 4/1992 |
| JP | 4-133064 | 5/1992 |
| JP | 04-175395 | 6/1992 |
| JP | 8-176293 | 7/1996 |
| JP | 08 199162 | 8/1996 |
| JP | 10-088122 A | 4/1998 |
| JP | 10-251633 | 9/1998 |
| JP | 2003-005392 | 1/2003 |
| KR | 10-2013-0047771 | 5/2013 |
| WO | 2004 018588 | 3/2004 |
| WO | WO 2004/018588 | * 3/2004 |

OTHER PUBLICATIONS

U.S. Appl. No. 11/568,578, filed Nov. 2, 2006, Funahashi.
U.S. Appl. No. 11/550,519, filed Oct. 18, 2006, Funahashi, et al.
U.S. Appl. No. 11/575,441, filed Mar. 16, 2007, Funahashi.
U.S. Appl. No. 11/761,437, filed Jun. 12, 2007, Matsuura, et al.
Office Action issued May 9, 2011, in Korea Patent Application No. 10-2006-7023676.
Sheila I. Hauck, et al., "Tetraazacyclophanes by Palladium-Catalyzed Aromatic Amination. Geometrically Defined, Stable, High-Spin Diradicals", Organic Letters, 1999, vol. 1, No. 3, pp. 2057-2060.
Ken-ichi Sugiura, et al., "Synthesis, properties, molecular structure and electron transfer salts of 13,13,14,14-tetracyano-1,6- and -1,8-pyrenoquinodimethanes (1,6-TCNP and 1,8-TCNP)", J. Mater. Chem., 2000, vol. 10, pp. 315-319.
Office Action issued May 23, 2013 in Korean Patent Application No. 10-2012-7017422.
Shinichiro Tamura, et al., "Organic Electroluminescent Devices With High Durability and Using N-Phenylaminopyrene Derivatives", XP002424830, Publication date: Apr. 1998.

* cited by examiner

Primary Examiner — Dawn L. Garrett
(74) Attorney, Agent, or Firm — Oblon, Spivak, McClelland, Maier & Neustadt, L.L.P.

(57) ABSTRACT

An aromatic amine derivative with a special structure obtained by bonding a diphenylamino group having a substituent to a substituted pyrene structure; and a process for producing the aromatic amine derivative. An organic electroluminescence device which comprises at least one organic thin film layer comprising a light emitting layer sandwiched between a pair of electrodes consisting of an anode and a cathode, wherein at least one of the organic thin film layer comprises the aromatic amine derivative singly or as its mixture component. An organic electroluminescence device having a prolonged lifetime and emits blue light with an enhanced efficiency of light emission and an aromatic amine derivative realizing the device are provided.

17 Claims, 18 Drawing Sheets

AROMATIC AMINE DERIVATIVE, ORGANIC ELECTROLUMINESCENT ELEMENT EMPLOYING THE SAME, AND PROCESS FOR PRODUCING AROMATIC AMINE DERIVATIVE

TECHNICAL FIELD

The present invention relates to an organic electroluminescence device used as a light source for a planar light emitting member such as a flat panel display of wall televisions and for a back light of displays and having a prolonged lifetime as well as an enhanced efficiency of light emission. Further, the present invention relates to a novel aromatic amine derivative realizing the organic electroluminescence device, and relates to a process for efficiently preparing an aromatic amine derivative having a three-dimensionally bulky substituent at its central skeleton.

BACKGROUND ART

Organic electroluminescence ("electroluminescence" will be occasionally referred to as "EL", hereinafter) devices which utilize organic substances are expected to be useful for application as an inexpensive full color display device of the solid light emission type having a great size and various developments on the organic EL devices are being conducted. In general, an organic EL device has a construction comprising a light emitting layer and a pair of electrodes sandwiching the light emitting layer. The light emission of the organic EL device is a phenomenon in which, when an electric field is applied between the two electrodes, electrons are injected from the cathode side and holes are injected from the anode side, the electrons are recombined with the holes in the light emitting layer to form an excited state, and energy generated when the excited state returns to the ground state is emitted as light.

As compared with an inorganic light emitting diode, conventional organic EL devices requires high driving voltage and only exhibited low luminance or low efficiency of light emission. Moreover, characteristic degradation of the conventional organic EL devices was also extravagant and as a result, they were not practically used. Although recent organic EL devices are improved step by steps, it has been still demanded to develop organic EL devices operable at low driving voltage, with excellent luminance and favorable efficiency of light emission.

For example, there is disclosed such a technology using a single monoanthracene compound as an organic light emitting material (refer to Japanese Unexamined Patent Application Laid-Open No. Hei 11-3782). However, in this technology, a luminance obtained by using the material is as low as 1650 cd/m$^2$, for example, at a current density of 165 mA/cm$^2$, and an efficiency of light emission thereof is very low, i.e., only 1 cd/A, which is practically unusable. Also, there is disclosed a technology using a single bisanthracene compound as an organic light emitting material (refer to Japanese Unexamined Patent Application Laid-Open No. Hei 8-012600). However, in this technology, an efficiency of light emission obtained by using the material is also as low as about 1 to 3 cd/A. Therefore, further improvement of the technology has been demanded for rendering it practically usable. Further, there is disclosed a technology using a mono- or bis-anthracene compound together with a distearyl compound in an organic light emitting medium layer (refer to International Application Published under PCT No. WO 00/06402). However, the device described therein fails to show a sufficiently long half lifetime and, therefore; further improvement has been demanded.

Moreover, an aromatic diamine compound is used as a charge transporting material for an electronic photographic photosensitive article or a material for the organic EL device. Particularly regarding with the organic EL device, the aromatic diamine compound is actively developed in late years in order to use as a material for a hole injecting layer, a hole transporting layer or a light emitting layer.

When it is used as an organic EL material, because any material except having high glass transition temperature fails to exhibit heat resistance in the organic EL device, the aromatic diamine derivative having many aromatic rings such as benzene rings or heterocycles in their molecules are developed extensively.

On the other hand, a pyrene derivative being a polycyclic aromatic ring is practical as a light emitting material (refer to, for example, Japanese Unexamined Patent Application Laid-Open Nos. Hei 4-68076, 2002-63988 and 2002-329578) however, because a pyrene skeleton is highly planar and accordingly has high crystallinity, crystallization easily advances in its amorphous film condition or when it drives the device. Damages in the thin film induced by crystallization invite either degradation of luminance or non-light emitting state both of the device. Further, when it is highly planar, a molecular association easily generates, and a thin film-formation of itself causes an extension of wavelength as compared with fluorescent spectrum in monomolecular state.

In order for overcoming the above problems, it is necessary to suppress crystallization or generation of an excimer either by three-dimensionally bulky property of the pyrene derivative itself or by introducing a bulky substituent having steric repulsion with pyrene skeleton or other substituent. Besides, an introduction of a substituent different from each other will suppress crystallization further more.

For example, Japanese Unexamined Patent Application Laid-Open No. Hei 4-175395 discloses binary substituted diaminopyrenes such as 1,6-substituted product, 1,8-substituted product, etc.; and Japanese Unexamined Patent Application Laid-Open Nos. Hei 07-101911 and Hei 07-249490 disclose monoaminopyrene derivatives. Further, Japanese Unexamined Patent Application Laid-Open No. Hei 10-88122 discloses 1,3,6,8-tetra aminopyrene derivative.

However, because the binary substituted derivative easily causes molecular association and because the tetra-substituted derivative has the same substituent, they do not suppress crystallization enough.

Furthermore, although fabrication of an organic EL device employing the diaminopyrene derivative described in Japanese Unexamined Patent Application Laid-Open No. Hei 4-175395 as a doping material enables to obtain an organic EL device having an enhanced efficiency of light emission, its lifetime is not long enough, and accordingly, further improvement was demanded. Moreover, although Japanese Unexamined Patent Application Laid-Open No. Hei 10-251633 discloses 1,6-substituted diaminopyrene compound as its embodiments, an employment of the compound for a light emitting material easily cause decomposition in an occasion of vapor deposition because its molecular weight is large.

DISCLOSURE OF THE INVENTION

The present invention has been made to overcome the above problems and has an object of providing an organic EL device having a prolonged lifetime and an enhanced efficiency of light emission, providing a novel aromatic amine derivative realizing the organic EL device, and providing a process for efficiently preparing an aromatic amine derivative having a three-dimensionally bulky substituent at its central skeleton.

As a result of extensive and intensive researches for developing aromatic amine derivatives having the above suitable properties and organic EL devices using the aromatic amine derivatives, the inventors have found that the object of the present invention can be achieved by employing an aromatic amine derivative represented by any one of following general formula (A), general formula (A') or general formula (A") whose substituted pyrene structure is bonded with a diphenylamino group having a substituent. Further, the inventors have found that the object of the present invention can be also achieved by halogenating 3,8-positions of 1,6-substituted pyrene as an initiating material and further preparing the aromatic amine derivative by aminating the 3,8-dihalogeno-1,6-substituted pyrene. The present invention has been accomplished on the basis of the above finding.

Thus, the present invention provides an aromatic amine derivative represented by any one of following general formulae (A), (A') and (A"):

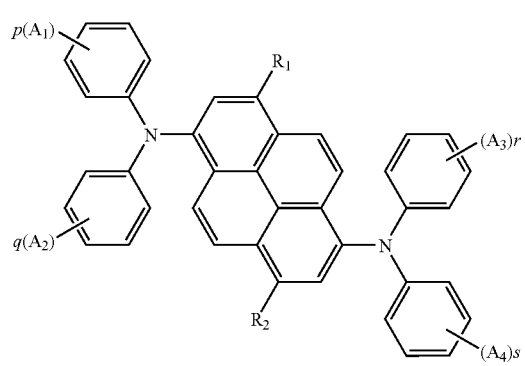

wherein $R_1$ and $R_2$ each independently represents a substituted or unsubstituted aryl group having 5 to 25 carbon atoms, a substituted or unsubstituted aralkyl group having 6 to 25 carbon atoms, a substituted or unsubstituted cycloalkyl group having 3 to 25 carbon atoms, a substituted or unsubstituted alkoxyl group having 1 to 20 carbon atoms, a substituted or unsubstituted aryloxy group having 5 to 25 carbon atoms, a substituted or unsubstituted arylamino group having 5 to 20 carbon atoms, a substituted or unsubstituted alkylamino group having 1 to 20 carbon atoms, or a cyano group;

$A_1$, $A_2$, $A_3$ and $A_4$ each independently represents a hydrogen atom, a substituted or unsubstituted alkyl group having 1 to 20 carbon atoms, a substituted or unsubstituted aryl group having 5 to 25 carbon atoms, a substituted or unsubstituted aralkyl group having 6 to 25 carbon atoms, a substituted or unsubstituted cycloalkyl group having 3 to 25 carbon atoms, a substituted or unsubstituted alkoxyl group having 1 to 20 carbon atoms, a substituted or unsubstituted aryloxy group having 5 to 25 carbon atoms, a substituted or unsubstituted arylamino group having 5 to 25 carbon atoms, a substituted or unsubstituted alkylamino group having 1 to 20 carbon atoms, or a cyano group; however, a case where any substituent of the groups represented by $R_1$, $R_2$, $A_1$, $A_2$, $A_3$ and $A_4$ comprises a vinyl group is excluded;

p, q, r and s each independently represents an integer of 1 to 5; when p represents an integer of 2 or greater, each of plural $A_1$ may be the same with, or different from each other, and may bond each other to form a saturated or unsaturated ring; when q represents an integer of 2 or greater, each of plural $A_2$ may be the same with, or different from each other, and may bond each other to form a saturated or unsaturated ring; when r represents an integer of 2 or greater, each of plural $A_3$ may be the same with, or different from each other, and may bond each other to form a saturated or unsaturated ring; and when s represents an integer of 2 or greater, each of plural $A_4$ may be the same with, or different from each other, and may bond each other to form a saturated or unsaturated ring.

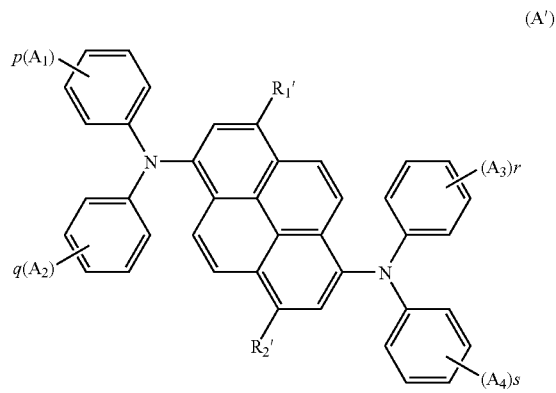

wherein $R_1'$ and $R_2'$ each independently represents a hydrogen atom or an alkyl group having 1 to 20 carbon atoms; excluding a case where both $R_1'$ and $R_2'$ are hydrogen atoms;

$A_1$, $A_2$, $A_3$ and $A_4$ each independently represent almost the same as the above description;

however, any one substituent for $A_1$, $A_2$, $A_3$ and $A_4$ bonds to meta-position of a bonding position where a nitrogen atom bonds;

further, a case where any substituent of the groups represented by $R_1'$, $R_2'$, $A_1$, $A_2$, $A_3$ and $A_4$ comprises a vinyl group is excluded; and p, q, r and s each independently represents the same as the above description.

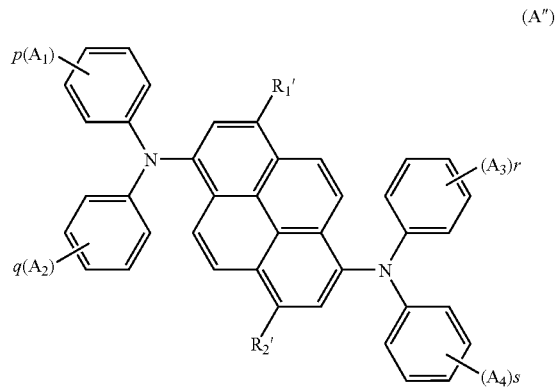

wherein $R_1'$ and $R_2'$ each independently represents the same as the above description;

$A_1$, $A_2$, $A_3$ and $A_4$ each independently represent almost the same as the above description;

however, when $A_1$, $A_2$, $A_3$ and $A_4$ all represent alkyl groups, a total sum made by adding numbers of carbon atoms in $A_1$, $A_2$, $A_3$ and $A_4$ does not exceed 10;

further, a case where any substituent of the groups represented by $R_1'$, $R_2'$, $A_1$, $A_2$, $A_3$ and $A_4$ comprises a vinyl group is excluded; and p, q, r and s each independently represents the same as the above description.

Further, the present invention provides an organic EL device which comprises at least one organic thin film layer comprising a light emitting layer sandwiched between a pair of electrodes consisting of an anode and a cathode, wherein at least one of the organic thin film layer comprises the aromatic amine derivative singly or as its mixture component.

Furthermore, the present invention provides a process for producing an aromatic amine derivative represented by a following general formula (2) by aminating 3,8-dihalogeno-1,6-substituted pyrene represented by a following general formula (1):

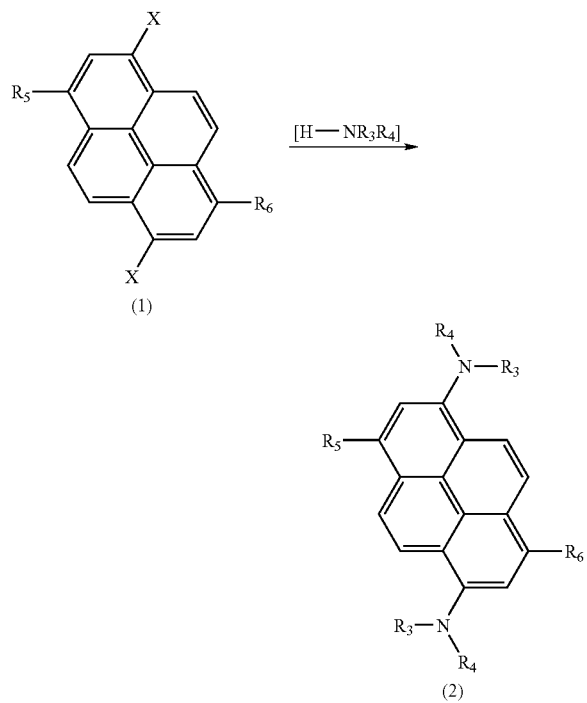

wherein $R_5$ and $R_6$ each independently represents a substituted or unsubstituted alkyl group having 1 to 50 carbon atoms, a substituted or unsubstituted aryl group having 5 to 50 carbon atoms, a substituted or unsubstituted aralkyl group having 6 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a halogen atom, cyano group or a silyl group;

X in the general formula (1) represents a halogen atom; and $R_3$ and $R_4$ in the general formula (2) each independently represents a substituted or unsubstituted aryl group having 5 to 50 carbon atoms or a substituted or unsubstituted alkyl group having 1 to 20 carbon atoms.

PREFERRED EMBODIMENTS TO CARRY OUT THE INVENTION

Figure 1:
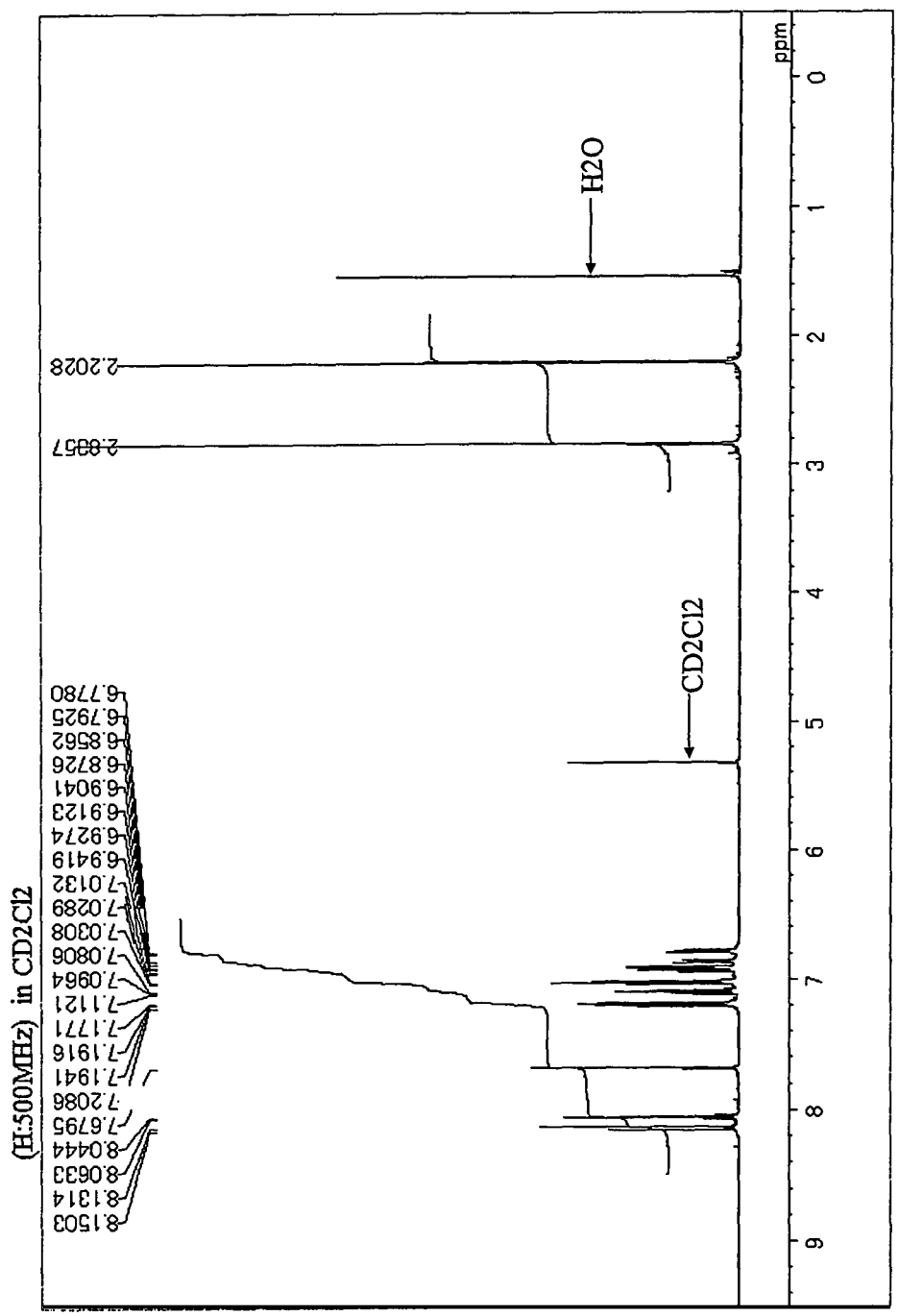
FIG. 1 is a chart showing a result of NMR measurement about Compound (D-3) as the aromatic amine derivative of the present invention.

The present invention provides an aromatic amine derivative represented by any one of following general formula (A), general formula (A') or general formula (A"):

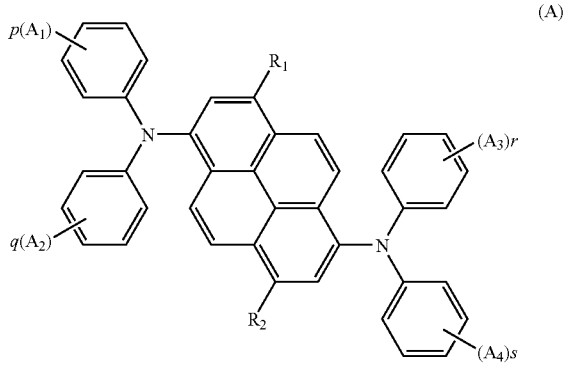

(A)

wherein $R_1$ and $R_2$ each independently represents a substituted or unsubstituted aryl group having 5 to 25 (preferably 5 to 10) carbon atoms, a substituted or unsubstituted aralkyl group having 6 to 25 (preferably 6 to 10) carbon atoms, a substituted or unsubstituted cycloalkyl group having 3 to 25 (preferably 3 to 10) carbon atoms, a substituted or unsubstituted alkoxyl group having 1 to 20 (preferably 1 to 6) carbon atoms, a substituted or unsubstituted aryloxy group having 5 to 25 (preferably 5 to 10) carbon atoms, a substituted or unsubstituted arylamino group having 5 to 20 (preferably 5 to 10) carbon atoms, a substituted or unsubstituted alkylamino group having 1 to 20 (preferably 1 to 6) carbon atoms or a cyano group.

Examples of the aryl group represented by the above $R_1$ or $R_2$ include phenyl group, 2-methylphenyl group, 3-methylphenyl group, 4-methylphenyl group, 4-ethylphenyl group, 3,4-dimethylphenyl group, 3,5-dimethylphenyl group, 3,4,5-trimethylphenyl group, o-biphenyl group, m-biphenyl group, p-biphenyl group, 4-cyanophenyl group, 3-cyanophenyl group, 4-methylbiphenyl group, 4-ethylbiphenyl group, 4-cyclohexylbiphenyl group, terphenyl group, 3,5-dichlorophenyl group, 1-naphthyl group, 2-naphthyl group, 5-methylnaphthyl group, anthryl group, pyrenyl group, 1,2,3,4-tetrahydronaphthyl group, 2,3-dihydroindanyl group, fluorenyl group and julolidinyl group; among those, phenyl group, 1-naphthyl group, 2-naphthyl group, 4-methylphenyl group, 3-methylphenyl group, 3,4-dimethylphenyl group, 3,5-dimethylphenyl group, 3,4,5-trimethylphenyl group, o-biphenyl group, m-biphenyl group, p-biphenyl group, 4-cyanophenyl group, 3-cyanophenyl group, 1,2,3,4-tetrahydro naphthyl group, 2,3-dihydro indanyl group, fluorenyl group and julolidinyl group are preferable; and further, phenyl group, 1-naphthyl group and 2-naphthyl group are more preferable.

Examples of the substituted or unsubstituted aralkyl group represented by the above $R_1$ or $R_2$ include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group, etc.

Examples of the cycloalkyl group represented by the above $R_1$ or $R_2$ include cyclopropyl group, cyclobutyl group, cyclopentyl group, cyclohexyl group, norbornene group, adamantyl group, etc.

Examples of the alkoxy group represented by the above $R_1$ or $R_2$ include methoxy group, ethoxy group, propoxy group, isopropoxy group, butoxy group, isobutoxy group, sec-butoxy group, tert-butoxy group, various pentyloxy groups, various hexyloxy groups, etc.

Examples of the aryloxy group represented by the above $R_1$ or $R_2$ include phenoxy group, tolyloxy group, naphthyloxy group, etc.

Examples of the arylamino group represented by the above $R_1$ or $R_2$ include diphenylamino group, ditolylamino group, isopropyldiphenylamino group, t-butyldiphenylamino group, diisopropyldiphenylamino group, di-t-butyldiphenylamino group, dinaphthylamino group, naphthylphenylamino group, etc.

Examples of the alkylamino group represented by the above $R_1$ or $R_2$ include dimethylamino group, diethylamino group, dihexylamino group, etc.

In the general formula (A), $A_1$, $A_2$, $A_3$ and $A_4$ each independently represents a hydrogen atom, a substituted or unsubstituted alkyl group having 1 to 20 (preferably 1 to 6) carbon atoms, a substituted or unsubstituted aryl group having 5 to 25 (preferably 5 to 10) carbon atoms, a substituted or unsubstituted aralkyl group having 6 to 25 (preferably 6 to 10) carbon atoms, a substituted or unsubstituted cycloalkyl group having 3 to 25 (preferably 3 to 10) carbon atoms, a substituted or unsubstituted alkoxyl group having 1 to 20 (preferably 1 to 6) carbon atoms, a substituted or unsubstituted aryloxy group having 5 to 25 (preferably 5 to 10) carbon atoms, a substituted or unsubstituted arylamino group having 5 to 25 (preferably 5 to 10) carbon atoms, a substituted or unsubstituted alkylamino group having 1 to 20 (preferably 1 to 6) carbon atoms, or a cyano group.

Examples of the alkyl group represented by the above $A_1$, $A_2$, $A_3$ or $A_4$ include methyl group, ethyl group, propyl group, isopropyl group, butyl group, sec-butyl group, tert-butyl group, pentyl group, hexyl group, heptyl group, octyl group, stearyl group, 2-phenylisopropyl group, trichloromethyl group, trifluoromethyl group, benzyl group, α-phenoxybenzyl group, α,α-dimethylbenzyl group, α,α-methylphenylbenzyl group, α,α-ditrifluoromethylbenzyl group, triphenylmethyl group, α-benzyloxybenzyl group, etc.; and among those, methyl group, ethyl group, propyl group, isopropyl group, butyl group, sec-butyl group and tert-butyl group are preferable.

Specific examples of the above aryl group, the above aralkyl group, the above cycloalkyl group, the above alkoxyl group, the above aryloxy group, the above arylamino group and the above alkylamino group are the same as the specific examples described about the foregoing $R_1$ and $R_2$.

In the general formula (A), a case where any substituent of the groups represented by $R_1$, $R_2$, $A_1$, $A_2$, $A_3$ and $A_4$ comprises a vinyl group is excluded.

In the general formula (A), p, q, r and s each independently represents an integer of 1 to 5; at least one of p, q, r and s is preferably 2 or greater because the organic EL device will have prolonged lifetime and will emit colors of high purity; further preferably 3 or greater.

Further, when p represents an integer of 2 or greater, each of plural $A_1$ may be the same with, or different from each other, and may bond each other to form a saturated or unsaturated ring. When q represents an integer of 2 or greater, each of plural $A_2$ may be the same with, or different from each other, and may bond each other to form a saturated or unsaturated ring. When r represents an integer of 2 or greater, each of plural $A_3$ may be the same with, or different from each other, and may bond each other to form a saturated or unsaturated ring. When s represents an integer of 2 or greater, each of plural $A_4$ may be the same with, or different from each other, and may bond each other to form a saturated or unsaturated ring.

Examples of the saturated or unsaturated ring are the same as those explained about the foregoing aryl group and the foregoing cycloalkyl group.

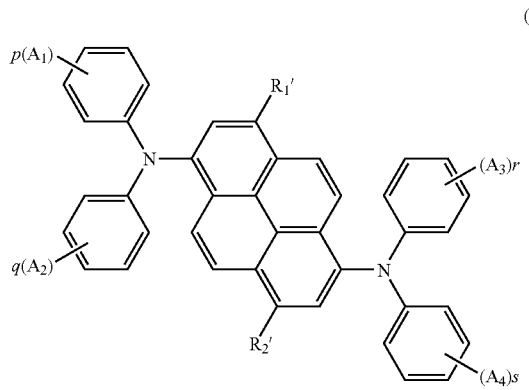

(A')

In the general formula (A'), $R_1'$ and $R_2'$ each independently represents a hydrogen atom or an alkyl group having 1 to 20 (preferably 1 to 6) carbon atoms; excluding a case where both $R_1'$ and $R_2'$ are hydrogen atoms.

Examples of the alkyl group represented by $R_1'$ or $R_2'$ include methyl group, ethyl group, propyl group, isopropyl group, butyl group, sec-butyl group, tert-butyl group, pentyl group, hexyl group, heptyl group, octyl group, stearyl group, 2-phenylisopropyl group, trichloromethyl group, trifluoromethyl group, benzyl group, α-phenoxybenzyl group, α,α-dimethylbenzyl group, α,α-methylphenylbenzyl group, α,α-ditrifluoromethyl benzyl group, triphenylmethyl group, α-benzyloxy benzyl group, etc.; and among those, methyl group, ethyl group, propyl group, isopropyl group, butyl group, sec-butyl group and tert-butyl group are preferable.

In the general formula (A'), $A_1, A_2, A_3$ and $A_4$ are almost the same as aforementioned including the specific examples.

However, any one substituent for $A_1, A_2, A_3$ and $A_4$ in the general formula (A') bonds to meta-position of a bonding position where a nitrogen atom bonds. This bonding position enables to further prolong the lifetime without lengthening wavelength of light emission as compared with a substrate having no substituent.

In the general formula (A'), a case where any substituent of the groups represented by $R_1'$, $R_2'$, $A_1, A_2, A_3$ and $A_4$ comprises a vinyl group is excluded.

In the general formula (A'), p, q, r and s each independently represents the same as aforementioned.

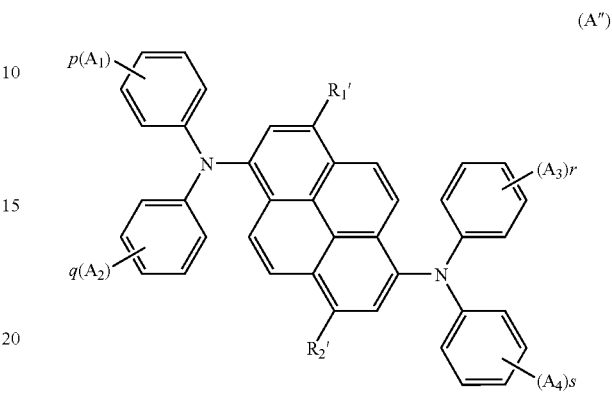

(A")

In the general formula (A"), $R_1'$ and $R_2'$ each independently represents a hydrogen atom or an alkyl group having 1 to 20 (preferably 1 to 5) carbon atoms; excluding a case where both $R_1'$ and $R_2'$ are hydrogen atoms.

Examples of the alkyl group represented by $R_1'$ or $R_2'$ include methyl group, ethyl group, propyl group, isopropyl group, butyl group, sec-butyl group, tert-butyl group, pentyl group, hexyl group, heptyl group, octyl group, stearyl group, 2-phenylisopropyl group, trichloromethyl group, trifluoromethyl group, benzyl group, α-phenoxybenzyl group, α,α-dimethylbenzyl group, α,α-methylphenylbenzyl group, α,α-ditrifluoromethylbenzyl group, triphenylmethyl group, α-benzyloxybenzyl group, etc.; among those, the alkyl group having 5 or less carbon atoms such as ethyl group, propyl group, isopropyl group, butyl group, sec-butyl group and tert-butyl group are preferable.

In the general formula (A"), $A_1, A_2, A_3$ and $A_4$ are almost the same as aforementioned including the specific examples.

However, when $A_1, A_2, A_3$ and $A_4$ in the general formula (A") all represent alkyl groups, a total sum made by adding numbers of carbon atoms in $A_1, A_2, A_3$ and $A_4$ does not exceed 10.

In the general formula (A"), a case where any substituent of the groups represented by $R_1'$, $R_2'$, $A_1, A_2, A_3$ and $A_4$ comprises a vinyl group is excluded.

In the general formula (A"), p, q, r and s each independently represents the same as aforementioned.

Specific examples of the aromatic amine derivatives represented by the general formula (A), the general formula (A') or the general formula (A") will be shown below, though not particularly limited thereto. Meanwhile, in the following compounds, Me represents a methyl group.

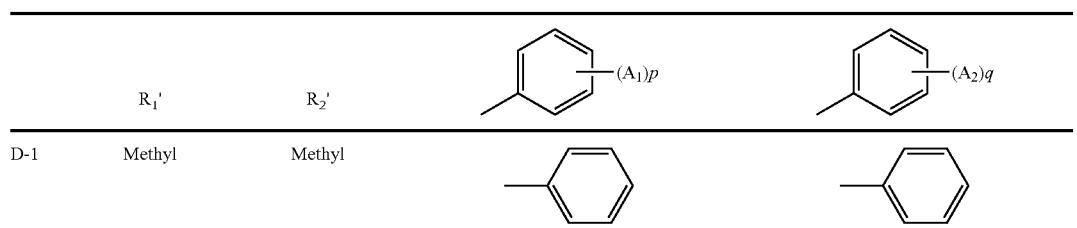

-continued
| | | | 11 | 12 |
|---|---|---|---|---|
| D-2 | Methyl | Methyl | 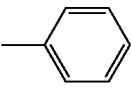 | 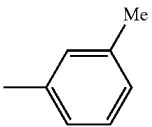 |
| D-3 | Methyl | Methyl | 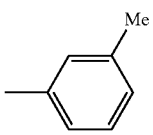 | 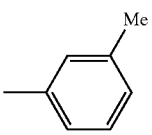 |
| D-4 | Methyl | Methyl | 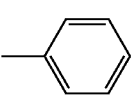 |  |
| D-5 | Methyl | Methyl | 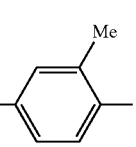 | 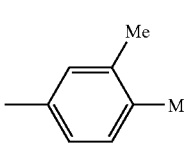 |
| D-6 | Methyl | Methyl | 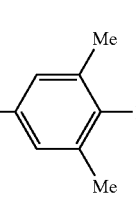 | 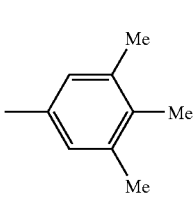 |
| D-7 | Methyl | Methyl | 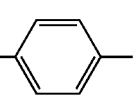 | 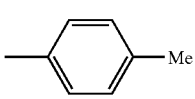 |
| D-8 | Methyl | Methyl | 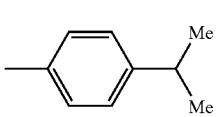 | 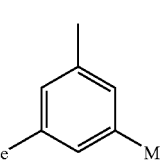 |
| D-9 | Methyl | Methyl | 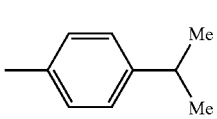 | 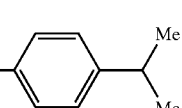 |
| D-10 | Methyl | Methyl | 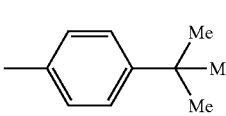 | 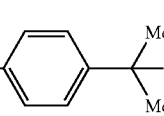 |
| D-11 | Methyl | Methyl | 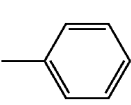 | 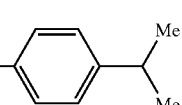 |
| D-12 | Methyl | Methyl | 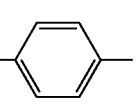 | 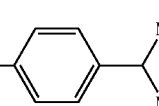 |
| D-13 | Methyl | Methyl | 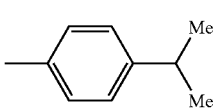 | 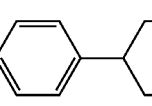 |

-continued
| | | | | |
|---|---|---|---|---|
| D-14 | Methyl | Methyl | 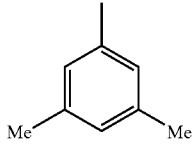 | 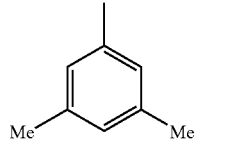 |
| D-15 | Methyl | Methyl | 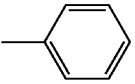 | 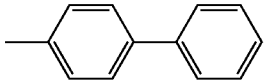 |
| D-16 | Methyl | Methyl | 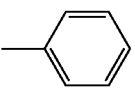 | 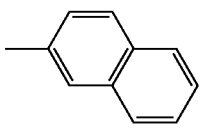 |
| D-17 | Methyl | Methyl | 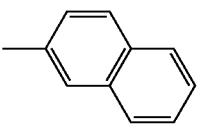 | 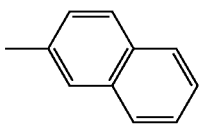 |
| D-18 | Methyl | Methyl | 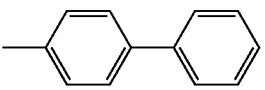 | 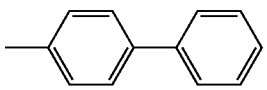 |
| D-19 | Ethyl | Ethyl | 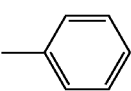 | 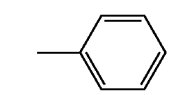 |
| D-20 | Ethyl | Ethyl | 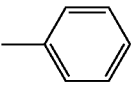 | 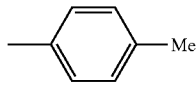 |
| D-21 | Ethyl | Ethyl | 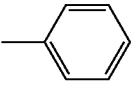 | 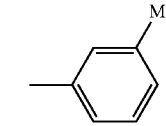 |
| D-22 | Ethyl | Ethyl | 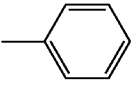 | 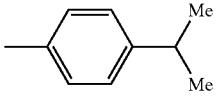 |
| D-23 | Ethyl | Ethyl | 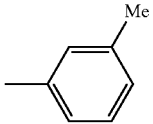 | 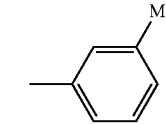 |
| D-24 | Ethyl | Ethyl | 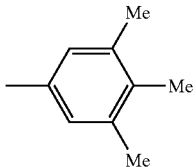 | 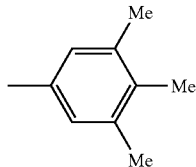 |
| D-25 | Ethyl | Ethyl | 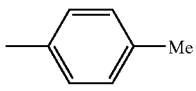 | 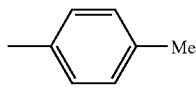 |
| D-26 | Ethyl | Ethyl | 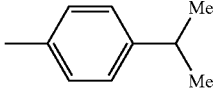 | 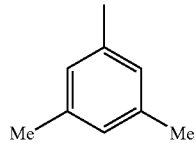 |

-continued

| | | | | |
|---|---|---|---|---|
| D-27 | Ethyl | Ethyl | 4-(isopropyl)phenyl | 4-(isopropyl)phenyl |
| D-28 | Ethyl | Ethyl | 4-(tert-butyl)phenyl | 4-(tert-butyl)phenyl |
| D-29 | Ethyl | Ethyl | 2,3-dimethylphenyl | 2,3-dimethylphenyl |
| D-30 | Ethyl | Ethyl | 4-methylphenyl | 4-ethylphenyl (with isopropyl group) |
| D-31 | Ethyl | Ethyl | 3,5-dimethylphenyl | 3,5-dimethylphenyl |
| D-32 | Ethyl | Ethyl | 4-(isopropyl)phenyl | 4-cyclohexylphenyl |
| D-33 | Ethyl | Ethyl | phenyl | 4-biphenyl |
| D-34 | Ethyl | Ethyl | phenyl | 2-naphthyl |
| D-35 | Ethyl | Ethyl | 2-naphthyl | 2-naphthyl |
| D-36 | Ethyl | Ethyl | 4-biphenyl | 4-biphenyl |
| D-37 | Isopropyl | Isopropyl | phenyl | phenyl |
| D-38 | Isopropyl | Isopropyl | phenyl | 3-methylphenyl |
| D-39 | Isopropyl | Isopropyl | 3-methylphenyl | 3-methylphenyl |

-continued
| | | | | |
|---|---|---|---|---|
| D-40 | Isopropyl | Isopropyl | 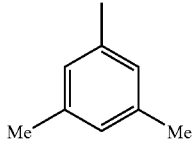 | 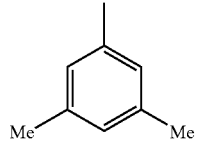 |
| D-41 | Isopropyl | Isopropyl |  |  |
| D-42 | Isopropyl | Isopropyl | 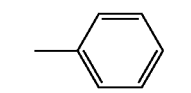 | 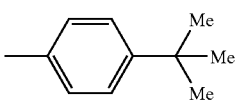 |
| D-43 | Isopropyl | Isopropyl | 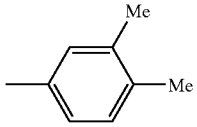 | 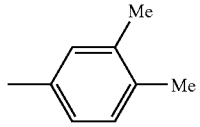 |
| D-44 | Isopropyl | Isopropyl | 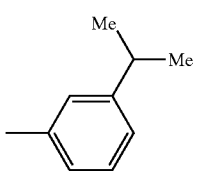 | 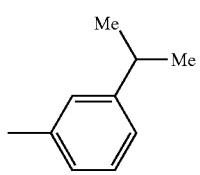 |
| D-45 | Isopropyl | Isopropyl | 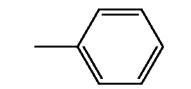 | 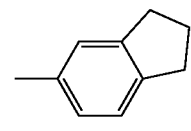 |
| D-46 | Isopropyl | Isopropyl | 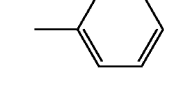 | 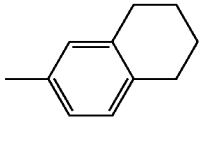 |
| D-47 | Isopropyl | Isopropyl | 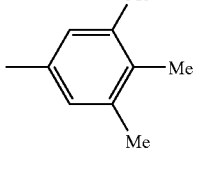 | 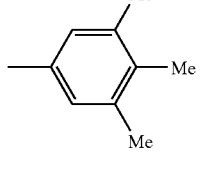 |
| D-48 | Isopropyl | Isopropyl | 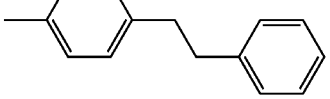 | 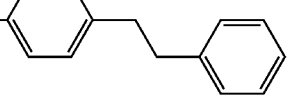 |
| D-49 | Isopropyl | Isopropyl | 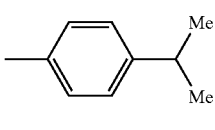 | 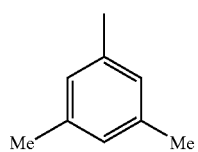 |
| D-50 | Isopropyl | Isopropyl | 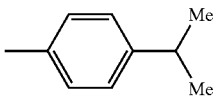 | 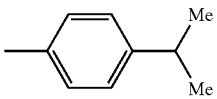 |
| D-51 | Isopropyl | Isopropyl | 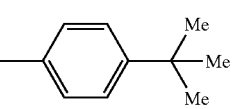 | 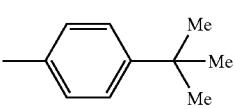 |

-continued
| | | | | |
|---|---|---|---|---|
| D-52 | Isopropyl | Isopropyl | 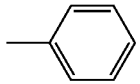 | 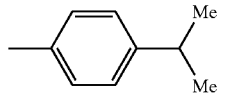 |
| D-53 | Isopropyl | Isopropyl | 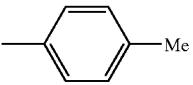 | 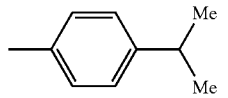 |
| D-54 | Isopropyl | Isopropyl | 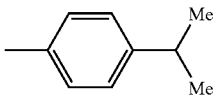 | 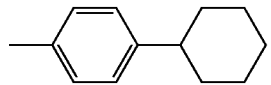 |
| D-55 | Isopropyl | Isopropyl | 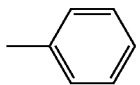 | 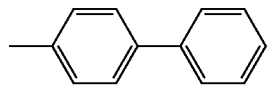 |
| D-56 | Isopropyl | Isopropyl | 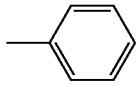 | 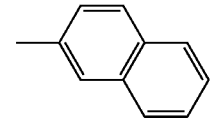 |
| D-57 | Isopropyl | Isopropyl | 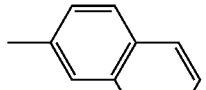 |  |
| D-58 | Isopropyl | Isopropyl | 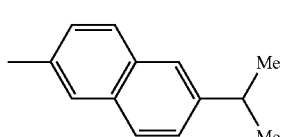 | 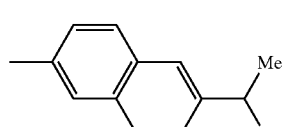 |
| D-59 | Isopropyl | Isopropyl | 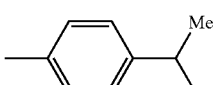 | 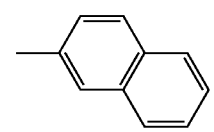 |
| D-60 | Isopropyl | Isopropyl | 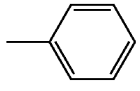 | 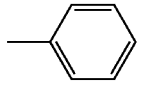 |
| D-61 | Isopropyl | Isopropyl | 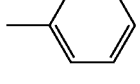 | 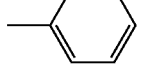 |
| D-62 | Isopropyl | Isopropyl | 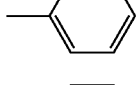 | 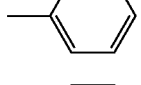 |
| D-63 | Isopropyl | Isopropyl | 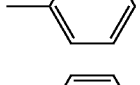 | 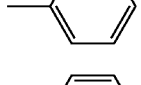 |
| D-64 | Isopropyl | Isopropyl | 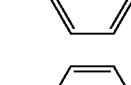 | 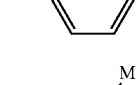 |
| D-65 | sec-butyl | sec-butyl | 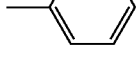 | 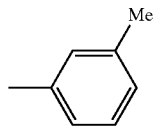 |

-continued

| | | | 21 | 22 |
|---|---|---|---|---|
| D-66 | sec-butyl | sec-butyl | 3-methylphenyl | 3-methylphenyl |
| D-67 | sec-butyl | sec-butyl | 3,5-dimethylphenyl (mesityl-like, 3,5-Me) | 3,5-dimethylphenyl |
| D-68 | sec-butyl | sec-butyl | 2,4,5-trimethylphenyl | 2,4,5-trimethylphenyl |
| D-69 | sec-butyl | sec-butyl | 2,3,4,6-tetramethylphenyl | 2,3,4,6-tetramethylphenyl |
| D-70 | sec-butyl | sec-butyl | 4-methylphenyl | 4-methylphenyl |
| D-71 | sec-butyl | sec-butyl | 4-ethylphenyl | 4-ethylphenyl |
| D-72 | sec-butyl | sec-butyl | 4-isopropylphenyl | 4-isopropylphenyl |
| D-73 | H | Methyl | phenyl | 4-(2-phenylpropan-2-yl)phenyl |
| D-74 | H | Methyl | 4-isopropylphenyl | 4-(2-phenylpropan-2-yl)phenyl |
| D-75 | H | Methyl | 9,9-dimethylfluoren-2-yl | 9,9-dimethylfluoren-2-yl |
| D-76 | H | Methyl | 2,4-dimethylphenyl | 2,4-dimethylphenyl |
| D-77 | H | Ethyl | 3-methylphenyl | 3-methylphenyl |

-continued
| | | | | |
|---|---|---|---|---|
| D-78 | H | Ethyl | 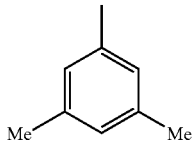 | 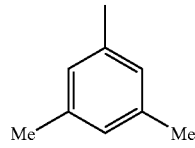 |
| D-79 | H | Isopropyl | 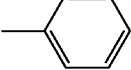 | 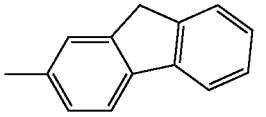 |
| D-80 | H | Isopropyl | 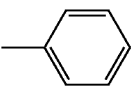 |  |
| D-81 | H | Isopropyl | 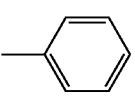 | 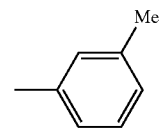 |
| D-82 | Cyclohexyl | Cyclohexyl | 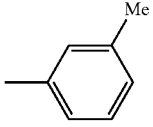 | 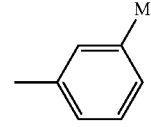 |
| D-83 | Cyclohexyl | Cyclohexyl | 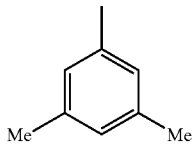 | 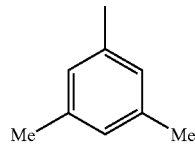 |
| D-84 | Cyclohexyl | Cyclohexyl | 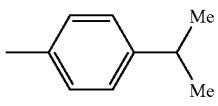 | 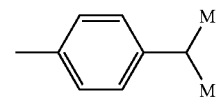 |
| D-85 | Cyclohexyl | Cyclohexyl | 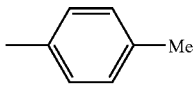 | 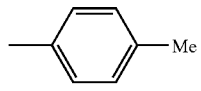 |
| D-86 | Cyclohexyl | Cyclohexyl | 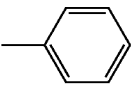 | 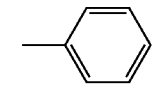 |
| D-87 | Butyl | Butyl | 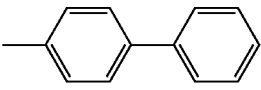 | 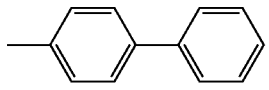 |
| D-88 | Butyl | Butyl | 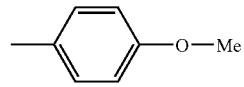 | 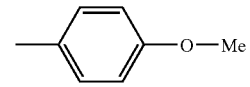 |
| D-89 | Butyl | Butyl | 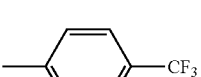 | 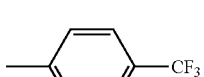 |
| D-90 | Butyl | Butyl | 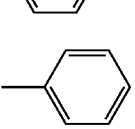 | 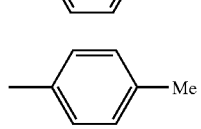 |

-continued

| | R₁ | R₂ | p | q |
|---|---|---|---|---|
| D-91 | Phenyl | Phenyl | phenyl | phenyl |
| D-92 | Phenyl | Phenyl | phenyl | 2,3-dimethylphenyl (Me, Me) |
| D-93 | Phenyl | Phenyl | 3-methylphenyl (Me) | 3-methylphenyl (Me) |
| D-94 | Phenyl | Phenyl | 3,5-dimethylphenyl (Me, Me) | 3,5-dimethylphenyl (Me, Me) |
| D-95 | Phenyl | Phenyl | 4-methylphenyl (Me) | 4-methylphenyl (Me) |
| D-96 | Phenyl | Phenyl | phenyl | 4-tert-butylphenyl (CMe₃) |
| D-97 | Phenyl | Phenyl | 3,4-dimethylphenyl (Me, Me) | 3,4-dimethylphenyl (Me, Me) |
| D-98 | Phenyl | Phenyl | 3-isopropylphenyl (CHMe₂) | 3-isopropylphenyl (CHMe₂) |
| D-99 | Phenyl | Phenyl | phenyl | indanyl |
| D-100 | Phenyl | Phenyl | phenyl | tetrahydronaphthyl |
| D-101 | Phenyl | Phenyl | 3,4,5-trimethylphenyl (Me, Me, Me) | 3,4,5-trimethylphenyl (Me, Me, Me) |

-continued

| ID | | | | |
|---|---|---|---|---|
| D-102 | Phenyl | Phenyl | 4-(propyl)phenyl | 4-(propyl)phenyl |
| D-103 | Phenyl | Phenyl | 4-(isopropyl)phenyl | 3,5-dimethylphenyl |
| D-104 | Phenyl | Phenyl | 4-(isopropyl)phenyl | 4-(isopropyl)phenyl |
| D-105 | Phenyl | Phenyl | 4-(tert-butyl)phenyl | 4-(tert-butyl)phenyl |
| D-106 | Phenyl | Phenyl | phenyl | 4-(isopropyl)phenyl |
| D-107 | Phenyl | Phenyl | 4-methylphenyl | 4-(isopropyl)phenyl |
| D-108 | o-biphenyl | o-biphenyl | phenyl | phenyl |
| D-109 | o-biphenyl | o-biphenyl | 3-methylphenyl | 3-methylphenyl |
| D-110 | o-biphenyl | o-biphenyl | 3,4-dimethylphenyl | 3,4-dimethylphenyl |
| D-111 | 4-methylphenyl | 4-methylphenyl | phenyl | 5,6,7,8-tetrahydronaphthalen-2-yl |
| D-112 | 4-methylphenyl | 4-methylphenyl | 4-methylphenyl | 4-methylphenyl |
| D-113 | 4-methylphenyl | 4-methylphenyl | 3,4-dimethylphenyl | 3,4-dimethylphenyl |
| D-114 | 4-methylphenyl | 4-methylphenyl | 4-(isopropyl)phenyl | 4-(naphthalen-2-yl)phenyl |

-continued

| | | | | |
|---|---|---|---|---|
| D-115 | 4-methylphenyl | 4-methylphenyl | 2,3,5-trimethylphenyl | 2,3,5-trimethylphenyl |
| D-116 | α,α-dimethylbenzyl | α,α-dimethylbenzyl | 4-isopropylphenyl | 4-(α,α-dimethylbenzyl)phenyl |
| D-117 | α,α-dimethylbenzyl | α,α-dimethylbenzyl | phenyl | 4-(α,α-dimethylbenzyl)phenyl |
| D-118 | Diphenylamino | Diphenylamino | 4-methylphenyl | 4-methylphenyl |
| D-119 | Diphenylamino | Diphenylamino | 4-biphenyl | 4-biphenyl |
| D-120 | Cyano | Cyano | 4-cyanophenyl | 4-cyanophenyl |
| D-121 | Cyano | Cyano | 4-trifluoromethylphenyl | 4-trifluoromethylphenyl |
| D-122 | 4-cyanophenyl | 4-cyanophenyl | 3,4-dimethylphenyl | 3,4-dimethylphenyl |
| D-123 | 4-cyanophenyl | 4-cyanophenyl | 3,4,5-trimethylphenyl | 3,4,5-trimethylphenyl |
| D-124 | 2-phenylethyl | 2-phenylethyl | 4-cyclohexylphenyl | 4-cyclohexylphenyl |
| D-125 | 2-phenylethyl | 2-phenylethyl | 4-isopropylphenyl | 4-isopropylphenyl |
| D-126 | 1-naphthyl | 1-naphthyl | phenyl | phenyl |
| D-127 | 1-naphthyl | 1-naphthyl | phenyl | 3-methylphenyl |

-continued
| | | | | |
|---|---|---|---|---|
| D-128 | 1-naphthyl | 1-naphthyl | 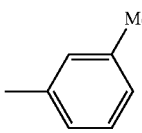 | 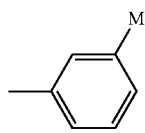 |
| D-129 | 1-naphthyl | 1-naphthyl | 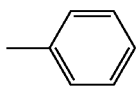 | 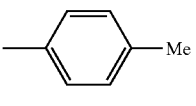 |
| D-130 | 1-naphthyl | 1-naphthyl | 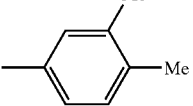 | 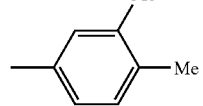 |
| D-131 | 1-naphthyl | 1-naphthyl | 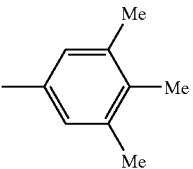 | 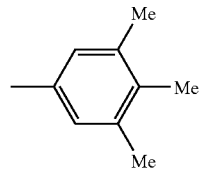 |
| D-132 | 1-naphthyl | 1-naphthyl | 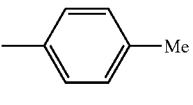 | 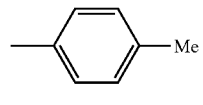 |
| D-133 | 1-naphthyl | 1-naphthyl | 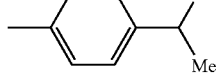 | 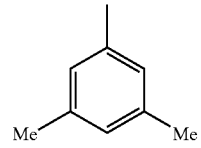 |
| D-134 | 1-naphthyl | 1-naphthyl | 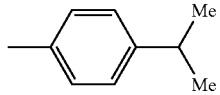 | 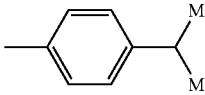 |
| D-135 | 1-naphthyl | 1-naphthyl | 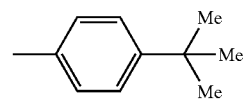 | 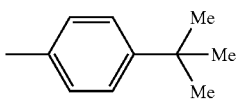 |
| D-136 | 1-naphthyl | 1-naphthyl | 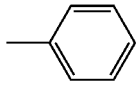 | 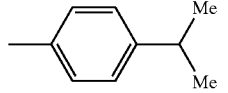 |
| D-137 | 1-naphthyl | 1-naphthyl | 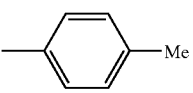 | 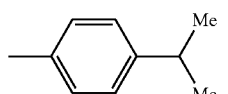 |
| D-138 | 1-naphthyl | 1-naphthyl | 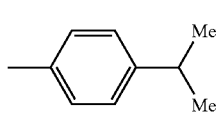 | 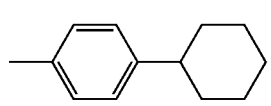 |
| D-139 | 1-naphthyl | 1-naphthyl | 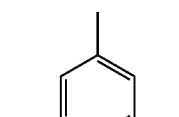 | 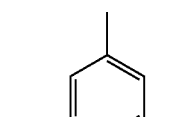 |
| D-140 | 1-naphthyl | 1-naphthyl | 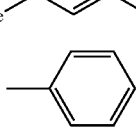 | 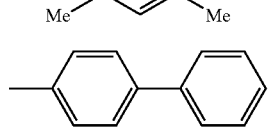 |

-continued

| | | | 33 | 34 |
|---|---|---|---|---|
| D-141 | 1-naphthyl | 1-naphthyl | phenyl | 2-naphthyl |
| D-142 | 1-naphthyl | 1-naphthyl | 2-naphthyl | 2-naphthyl |
| D-143 | 2-naphthyl | 2-naphthyl | phenyl | phenyl |
| D-144 | 2-naphthyl | 2-naphthyl | phenyl | 4-methylphenyl |
| D-145 | 2-naphthyl | 2-naphthyl | phenyl | 3-methylphenyl |
| D-146 | 2-naphthyl | 2-naphthyl | phenyl | 4-isopropylphenyl |
| D-147 | 2-naphthyl | 2-naphthyl | 3-methylphenyl | 3-methylphenyl |
| D-148 | 2-naphthyl | 2-naphthyl | 3,4,5-trimethylphenyl | 3,4,5-trimethylphenyl |
| D-149 | 2-naphthyl | 2-naphthyl | 4-methylphenyl | 4-methylphenyl |
| D-150 | 2-naphthyl | 2-naphthyl | 4-isopropylphenyl | 3,5-dimethylphenyl |
| D-151 | 2-naphthyl | 2-naphthyl | 4-isopropylphenyl | 4-isopropylphenyl |
| D-152 | 2-naphthyl | 2-naphthyl | 4-tert-butylphenyl | 4-tert-butylphenyl |

-continued
| | | | | |
|---|---|---|---|---|
| D-153 | 2-naphthyl | 2-naphthyl | 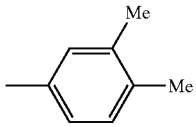 | 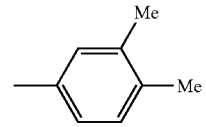 |
| D-154 | 2-naphthyl | 2-naphthyl | 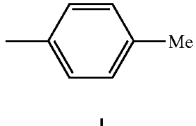 | 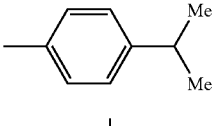 |
| D-155 | 2-naphthyl | 2-naphthyl | 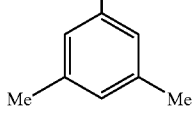 | 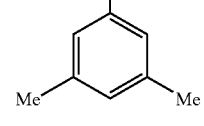 |
| D-156 | 2-naphthyl | 2-naphthyl | 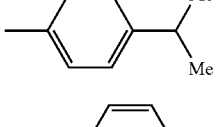 | 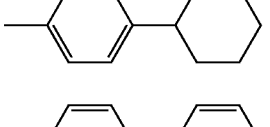 |
| D-157 | 2-naphthyl | 2-naphthyl | 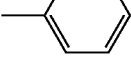 | 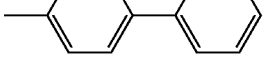 |
| D-158 | 2-naphthyl | 2-naphthyl | 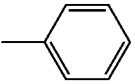 | 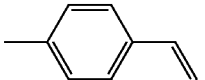 |
| D-159 | 2-naphthyl | 2-naphthyl | 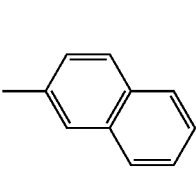 | 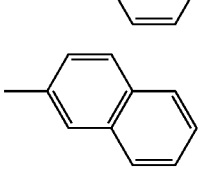 |
| | $R_1'$ | $R_2'$ | ⟨phenyl⟩–$(A_3)r$ | ⟨phenyl⟩–$(A_4)s$ |
|---|---|---|---|---|
| D-1 | Methyl | Methyl | 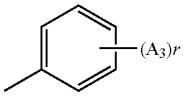 | 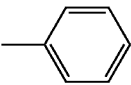 |
| D-2 | Methyl | Methyl | | 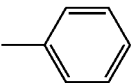 |
| D-3 | Methyl | Methyl | | |
| D-4 | Methyl | Methyl | |  |
| D-5 | Methyl | Methyl | 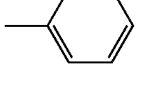 | 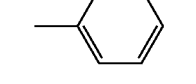 |

| | | | 37 | 38 |
|---|---|---|---|---|
| | | | -continued | |
| D-6 | Methyl | Methyl | 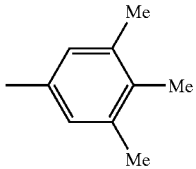 | 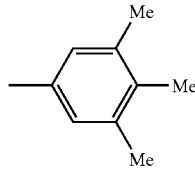 |
| D-7 | Methyl | Methyl | 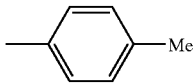 |  |
| D-8 | Methyl | Methyl | 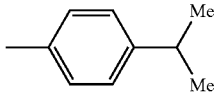 | 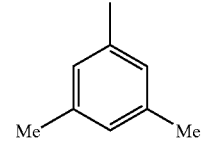 |
| D-9 | Methyl | Methyl | 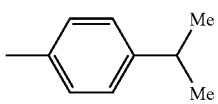 | 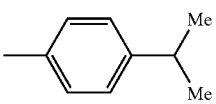 |
| D-10 | Methyl | Methyl | 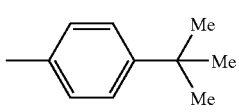 | 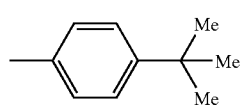 |
| D-11 | Methyl | Methyl | 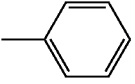 | 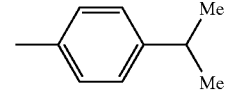 |
| D-12 | Methyl | Methyl | 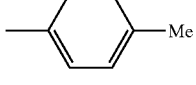 | 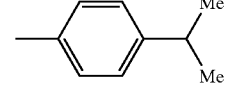 |
| D-13 | Methyl | Methyl | 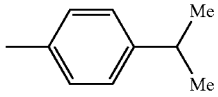 | 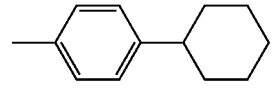 |
| D-14 | Methyl | Methyl | 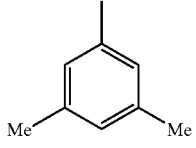 | 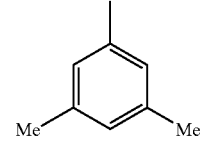 |
| D-15 | Methyl | Methyl | 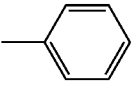 | 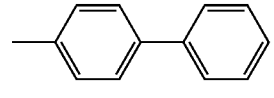 |
| D-16 | Methyl | Methyl | 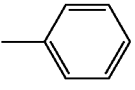 | 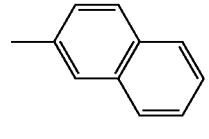 |
| D-17 | Methyl | Methyl | 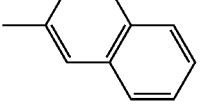 | 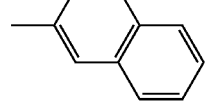 |
| D-18 | Methyl | Methyl | 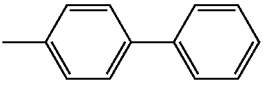 | 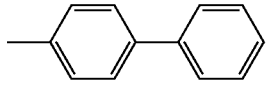 |

-continued

| | | | Ar1 | Ar2 |
|---|---|---|---|---|
| D-19 | Ethyl | Ethyl | phenyl | phenyl |
| D-20 | Ethyl | Ethyl | phenyl | 4-Me-phenyl |
| D-21 | Ethyl | Ethyl | phenyl | 3-Me-phenyl |
| D-22 | Ethyl | Ethyl | phenyl | 4-isopropyl-phenyl |
| D-23 | Ethyl | Ethyl | 3-Me-phenyl | 3-Me-phenyl |
| D-24 | Ethyl | Ethyl | 3,4,5-triMe-phenyl | 3,4,5-triMe-phenyl |
| D-25 | Ethyl | Ethyl | 4-Me-phenyl | 4-Me-phenyl |
| D-26 | Ethyl | Ethyl | 4-isopropyl-phenyl | 3,5-diMe-phenyl |
| D-27 | Ethyl | Ethyl | 4-isopropyl-phenyl | 4-isopropyl-phenyl |
| D-28 | Ethyl | Ethyl | 4-tBu-phenyl | 4-tBu-phenyl |
| D-29 | Ethyl | Ethyl | 3,4-diMe-phenyl | 3,4-diMe-phenyl |
| D-30 | Ethyl | Ethyl | 4-Me-phenyl | 4-isopropyl-phenyl |

-continued
| | | | 41 | 42 |
|---|---|---|---|---|
| D-31 | Ethyl | Ethyl | 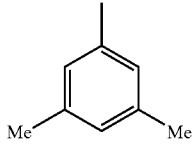 | 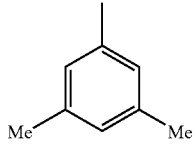 |
| D-32 | Ethyl | Ethyl | 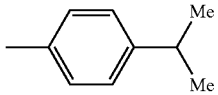 | 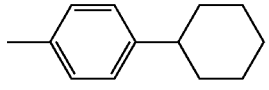 |
| D-33 | Ethyl | Ethyl | 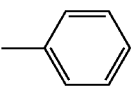 | 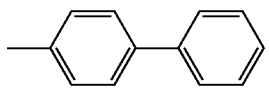 |
| D-34 | Ethyl | Ethyl | 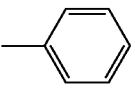 | 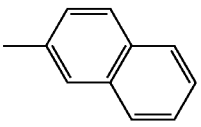 |
| D-35 | Ethyl | Ethyl | 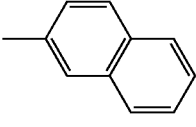 | 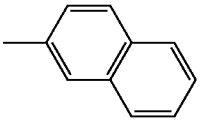 |
| D-36 | Ethyl | Ethyl | 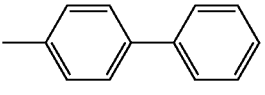 | 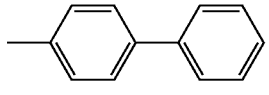 |
| D-37 | Isopropyl | Isopropyl | 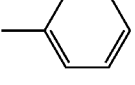 | 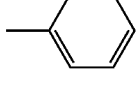 |
| D-38 | Isopropyl | Isopropyl | 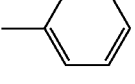 | 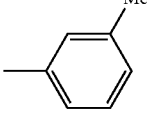 |
| D-39 | Isopropyl | Isopropyl | 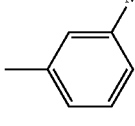 | 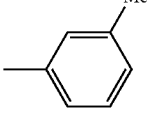 |
| D-40 | Isopropyl | Isopropyl | 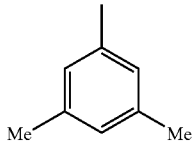 | 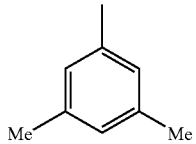 |
| D-41 | Isopropyl | Isopropyl | 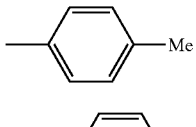 | 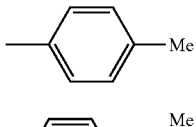 |
| D-42 | Isopropyl | Isopropyl | 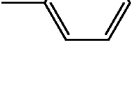 | 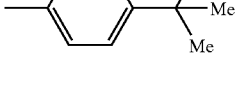 |
| D-43 | Isopropyl | Isopropyl | 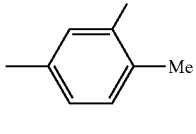 | 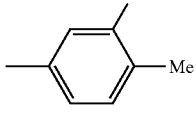 |

-continued
| | | | | |
|---|---|---|---|---|
| D-44 | Isopropyl | Isopropyl | 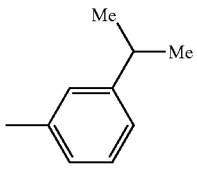 | 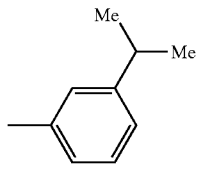 |
| D-45 | Isopropyl | Isopropyl | 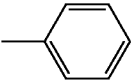 | 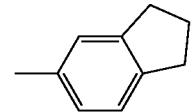 |
| D-46 | Isopropyl | Isopropyl | 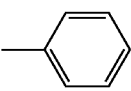 | 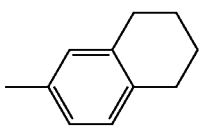 |
| D-47 | Isopropyl | Isopropyl | 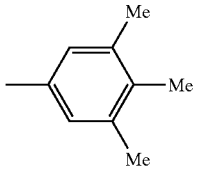 | 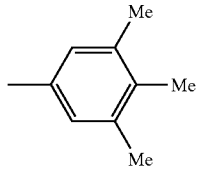 |
| D-48 | Isopropyl | Isopropyl | 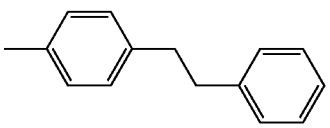 | 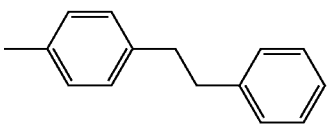 |
| D-49 | Isopropyl | Isopropyl | 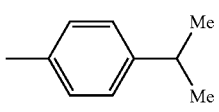 | 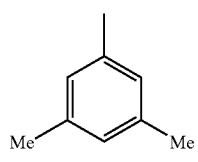 |
| D-50 | Isopropyl | Isopropyl | 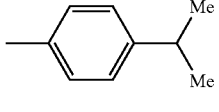 | 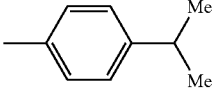 |
| D-51 | Isopropyl | Isopropyl | 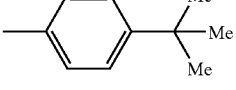 | 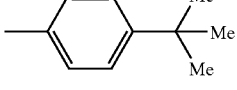 |
| D-52 | Isopropyl | Isopropyl | 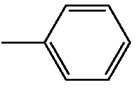 | 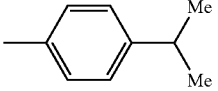 |
| D-53 | Isopropyl | Isopropyl | 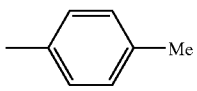 | 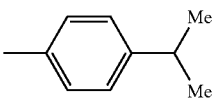 |
| D-54 | Isopropyl | Isopropyl | 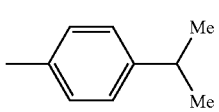 | 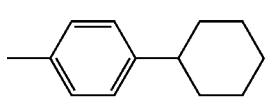 |
| D-55 | Isopropyl | Isopropyl | 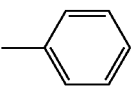 | 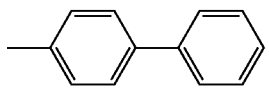 |

-continued
| | | | | |
|---|---|---|---|---|
| D-56 | Isopropyl | Isopropyl | 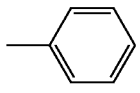 | 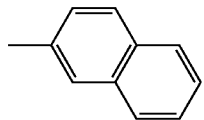 |
| D-57 | Isopropyl | Isopropyl | 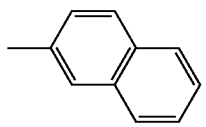 | 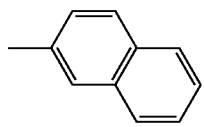 |
| D-58 | Isopropyl | Isopropyl | 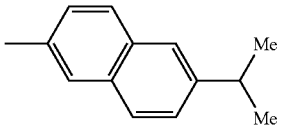 | 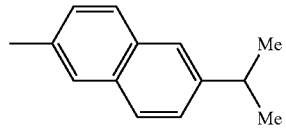 |
| D-59 | Isopropyl | Isopropyl | 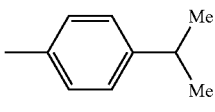 | 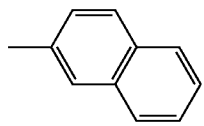 |
| D-60 | Isopropyl | Isopropyl | 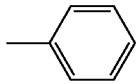 |  |
| D-61 | Isopropyl | Isopropyl | 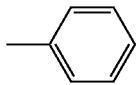 | 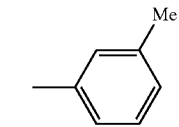 |
| D-62 | Isopropyl | Isopropyl | 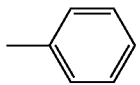 | 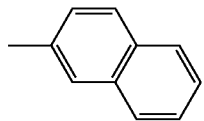 |
| D-63 | Isopropyl | Isopropyl | 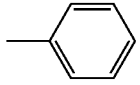 | 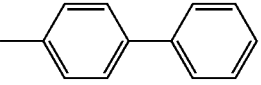 |
| D-64 | Isopropyl | Isopropyl | 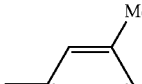 |  |
| D-65 | sec-butyl | sec-butyl | 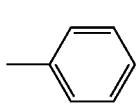 | 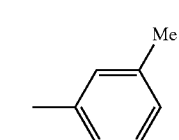 |
| D-66 | sec-butyl | sec-butyl | 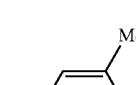 | 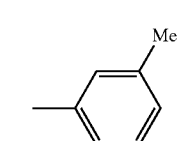 |
| D-67 | sec-butyl | sec-butyl | 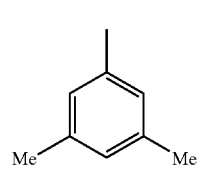 | 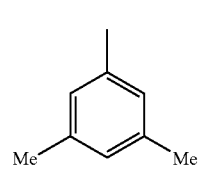 |

-continued

| | | | 47 | 48 |
|---|---|---|---|---|
| D-68 | sec-butyl | sec-butyl | 2,4-dimethylphenyl | 2,4-dimethylphenyl |
| D-69 | sec-butyl | sec-butyl | 2,4,6-trimethylphenyl | 2,4,6-trimethylphenyl |
| D-70 | sec-butyl | sec-butyl | 4-methylphenyl | 4-methylphenyl |
| D-71 | sec-butyl | sec-butyl | 4-(ethyl)phenyl | 4-(ethyl)phenyl |
| D-72 | sec-butyl | sec-butyl | 4-(isopropyl)phenyl | 4-(isopropyl)phenyl |
| D-73 | H | Methyl | phenyl | 4-(2-phenylpropan-2-yl)phenyl |
| D-74 | H | Methyl | 4-(isopropyl)phenyl | 4-(2-phenylpropan-2-yl)phenyl |
| D-75 | H | Methyl | 9,9-dimethylfluoren-2-yl | 9,9-dimethylfluoren-2-yl |
| D-76 | H | Methyl | 2,4-dimethylphenyl | 2,4-dimethylphenyl |
| D-77 | H | Ethyl | 3-methylphenyl | 3-methylphenyl |
| D-78 | H | Ethyl | 3,5-dimethylphenyl | 3,5-dimethylphenyl |
| D-79 | H | Isopropyl | phenyl | fluoren-2-yl |

-continued
| | $R_1$ | $R_2$ | 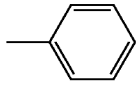 | 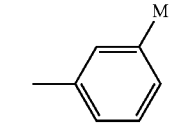 |
|---|---|---|---|---|
| D-80 | H | Isopropyl | 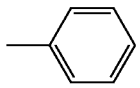 |  |
| D-81 | H | Isopropyl | 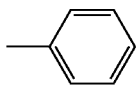 | 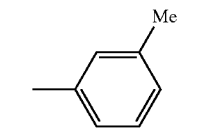 |
| D-82 | Cyclohexyl | Cyclohexyl | 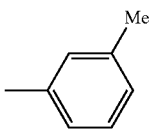 | 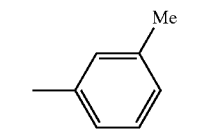 |
| D-83 | Cyclohexyl | Cyclohexyl | 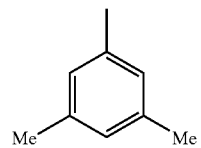 | 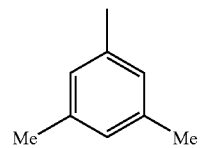 |
| D-84 | Cyclohexyl | Cyclohexyl | 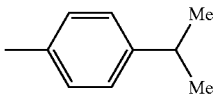 | 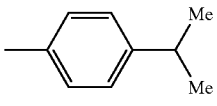 |
| D-85 | Cyclohexyl | Cyclohexyl |  | 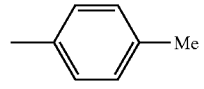 |
| D-86 | Cyclohexyl | Cyclohexyl | 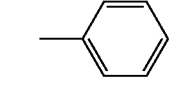 | 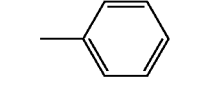 |
| D-87 | Butyl | Butyl | 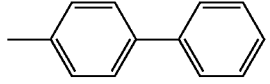 | 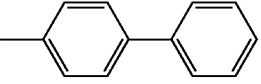 |
| D-88 | Butyl | Butyl | 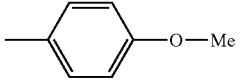 | 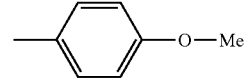 |
| D-89 | Butyl | Butyl | 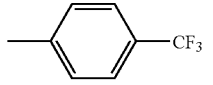 |  |
| D-90 | Butyl | Butyl | 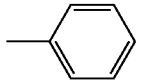 |  |
| D-91 | Phenyl | Phenyl | 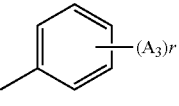 | 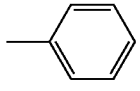 |
| D-92 | Phenyl | Phenyl | 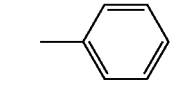 | 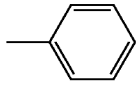 |

-continued
| | | | | |
|---|---|---|---|---|
| D-93 | Phenyl | Phenyl | 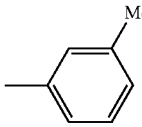 | 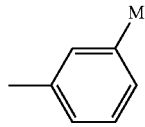 |
| D-94 | Phenyl | Phenyl | 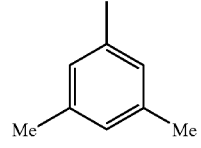 | 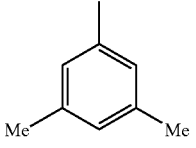 |
| D-95 | Phenyl | Phenyl |  | 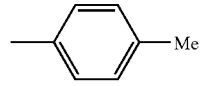 |
| D-96 | Phenyl | Phenyl | 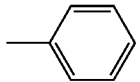 | 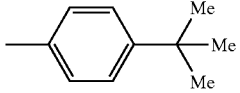 |
| D-97 | Phenyl | Phenyl | 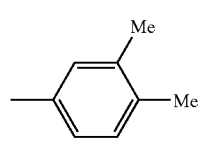 | 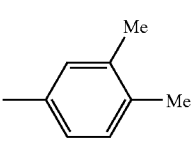 |
| D-98 | Phenyl | Phenyl | 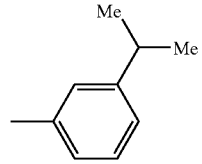 | 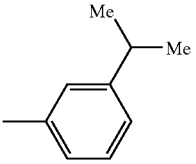 |
| D-99 | Phenyl | Phenyl | 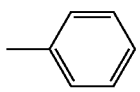 | 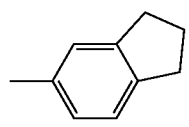 |
| D-100 | Phenyl | Phenyl | 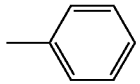 | 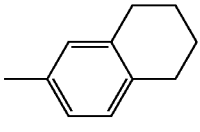 |
| D-101 | Phenyl | Phenyl | 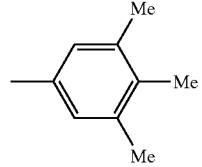 | 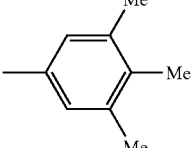 |
| D-102 | Phenyl | Phenyl | 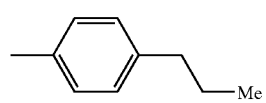 | 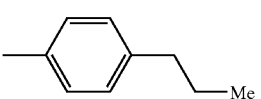 |
| D-103 | Phenyl | Phenyl | 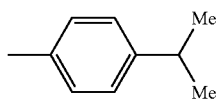 | 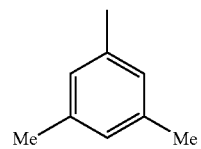 |
| D-104 | Phenyl | Phenyl | 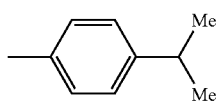 | 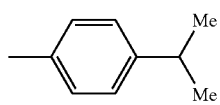 |

-continued
| | | | | |
|---|---|---|---|---|
| D-105 | Phenyl | Phenyl | 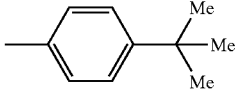 | 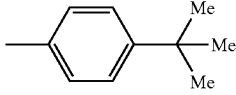 |
| D-106 | Phenyl | Phenyl | 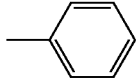 | 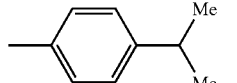 |
| D-107 | Phenyl | Phenyl | 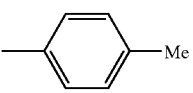 | 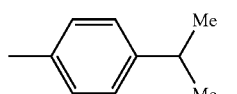 |
| D-108 | o-biphenyl | o-biphenyl | 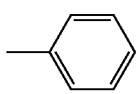 | 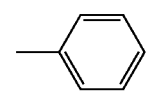 |
| D-109 | o-biphenyl | o-biphenyl | 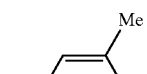 | 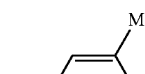 |
| D-110 | o-biphenyl | o-biphenyl | 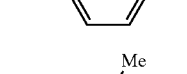 | 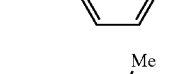 |
| D-111 | 4-methylphenyl | 4-methylphenyl | 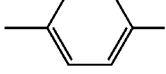 | 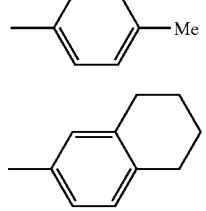 |
| D-112 | 4-methylphenyl | 4-methylphenyl | 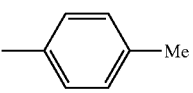 |  |
| D-113 | 4-methylphenyl | 4-methylphenyl | 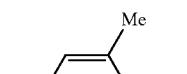 | 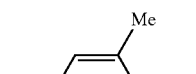 |
| D-114 | 4-methylphenyl | 4-methylphenyl | 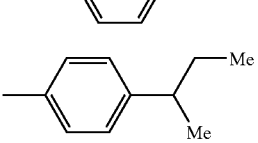 | 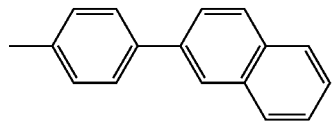 [SMILES: Cc1ccc(-c2ccc3ccccc3c2)cc1] |
| D-115 | 4-methylphenyl | 4-methylphenyl | 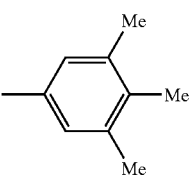 | 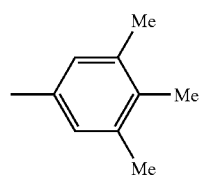 |
| D-116 | α,α-dimethylbenzyl | α,α-dimethylbenzyl | 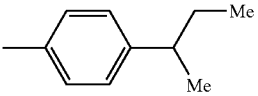 | 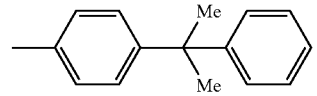 |
| D-117 | α,α-dimethylbenzyl | α,α-dimethylbenzyl | 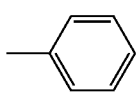 | 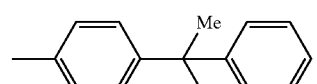 |

-continued
| | | | | |
|---|---|---|---|---|
| D-118 | Diphenylamino | Diphenylamino |  |  |
| D-119 | Diphenylamino | Diphenylamino | 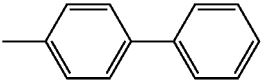 | 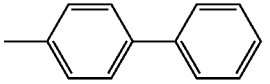 |
| D-120 | Cyano | Cyano | 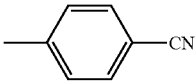 |  |
| D-121 | Cyano | Cyano | 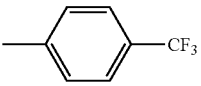 | 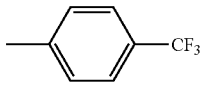 |
| D-122 | 4-cyanophenyl | 4-cyanophenyl | 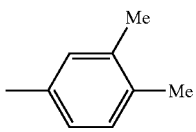 | 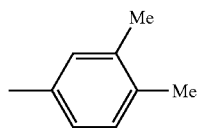 |
| D-123 | 4-cyanophenyl | 4-cyanophenyl | 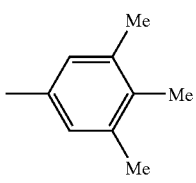 | 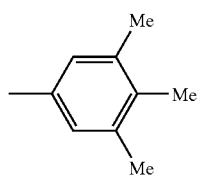 |
| D-124 | 2-phenylethyl | 2-phenylethyl | 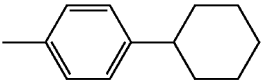 | 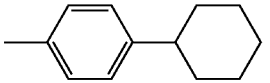 |
| D-125 | 2-phenylethyl | 2-phenylethyl | 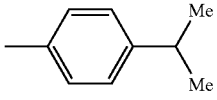 | 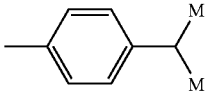 |
| D-126 | 1-naphthyl | 1-naphthyl | 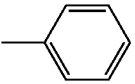 | 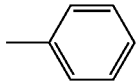 |
| D-127 | 1-naphthyl | 1-naphthyl | 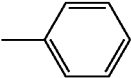 | 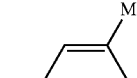 |
| D-128 | 1-naphthyl | 1-naphthyl |  | 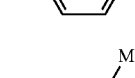 |
| D-129 | 1-naphthyl | 1-naphthyl | 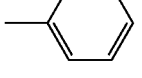 | 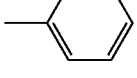 |
| D-130 | 1-naphthyl | 1-naphthyl | 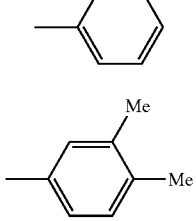 | 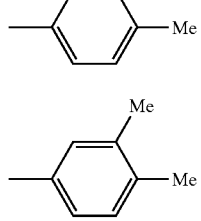 |

-continued
| | | | | |
|---|---|---|---|---|
| D-131 | 1-naphthyl | 1-naphthyl | 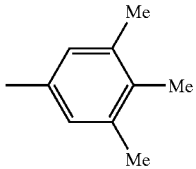 | 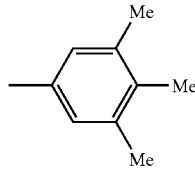 |
| D-132 | 1-naphthyl | 1-naphthyl | 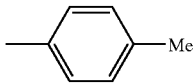 |  |
| D-133 | 1-naphthyl | 1-naphthyl | 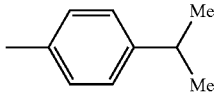 | 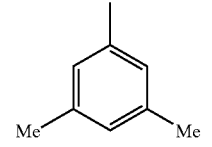 |
| D-134 | 1-naphthyl | 1-naphthyl | 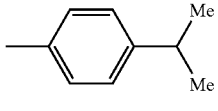 | 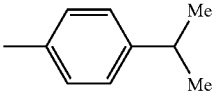 |
| D-135 | 1-naphthyl | 1-naphthyl | 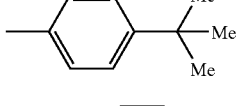 | 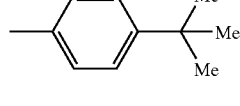 |
| D-136 | 1-naphthyl | 1-naphthyl | 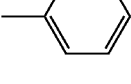 | 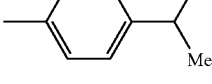 |
| D-137 | 1-naphthyl | 1-naphthyl | 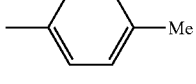 | 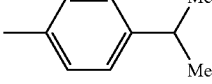 |
| D-138 | 1-naphthyl | 1-naphthyl | 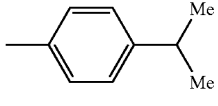 | 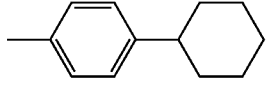 |
| D-139 | 1-naphthyl | 1-naphthyl | 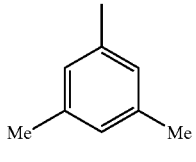 | 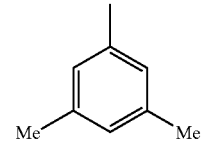 |
| D-140 | 1-naphthyl | 1-naphthyl | 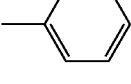 | 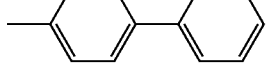 |
| D-141 | 1-naphthyl | 1-naphthyl | 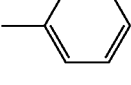 | 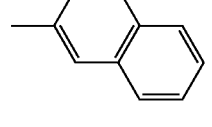 |
| D-142 | 1-naphthyl | 1-naphthyl | 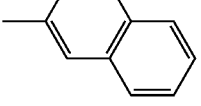 | 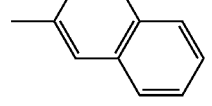 |
| D-143 | 2-naphthyl | 2-naphthyl | 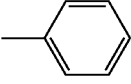 | 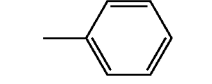 |

-continued
| | | | | |
|---|---|---|---|---|
| D-144 | 2-naphthyl | 2-naphthyl | 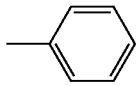 |  |
| D-145 | 2-naphthyl | 2-naphthyl | 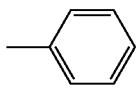 | 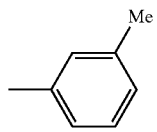 |
| D-146 | 2-naphthyl | 2-naphthyl | 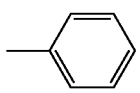 | 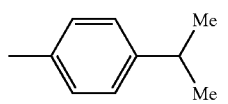 |
| D-147 | 2-naphthyl | 2-naphthyl | 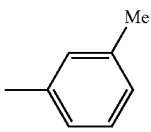 | 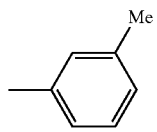 |
| D-148 | 2-naphthyl | 2-naphthyl | 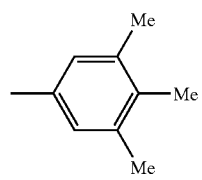 | 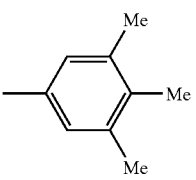 |
| D-149 | 2-naphthyl | 2-naphthyl |  | 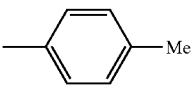 |
| D-150 | 2-naphthyl | 2-naphthyl | 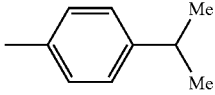 | 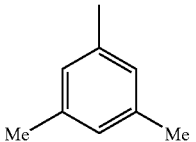 |
| D-151 | 2-naphthyl | 2-naphthyl | 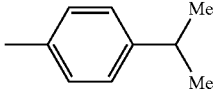 | 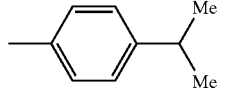 |
| D-152 | 2-naphthyl | 2-naphthyl | 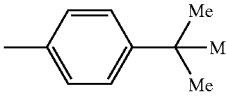 | 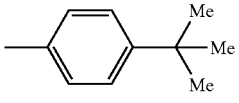 |
| D-153 | 2-naphthyl | 2-naphthyl | 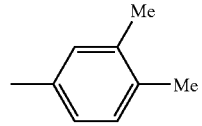 | 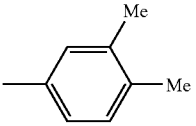 |
| D-154 | 2-naphthyl | 2-naphthyl | 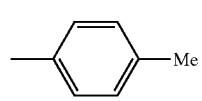 | 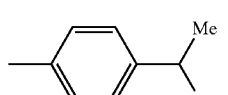 |
| D-155 | 2-naphthyl | 2-naphthyl | 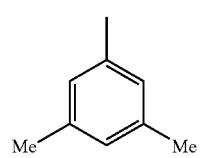 | 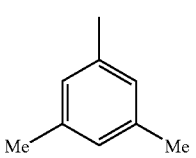 |

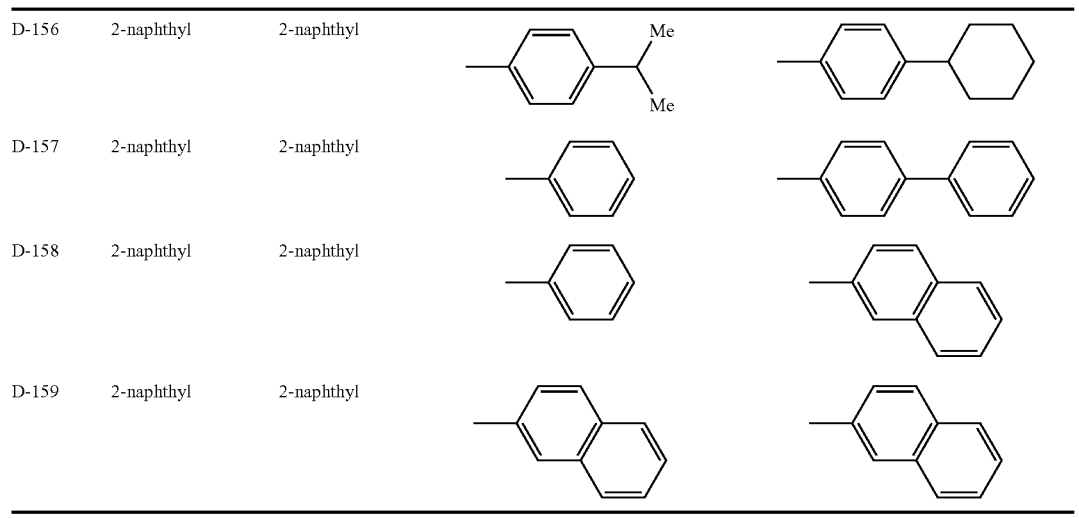

In the aromatic amine derivative of the present invention represented by the general formula (A), the general formula (A') or the general formula (A"), bonding a diphenylamine having substituent to a pyrene structure having, in particular, an alkyl group or a substituted or unsubstituted aryl group in order for preventing association between compounds enables to prolong its lifetime. Further, the aromatic amine derivatives have a strong fluorescence in their solid states, and are excellent in electric field light emission, which leads to a fluorescent quantum efficiency as high as 0.3 or greater. In addition, the aromatic amine derivatives of the present invention exhibit not only excellent capabilities of injecting and transporting holes from the metal electrode or organic thin film layers, but also excellent capabilities of injecting and transporting electrons from the metal electrode or organic thin film layers and, therefore, are usefully usable as light emitting materials, particularly as doping materials, for organic EL devices. Besides, the aromatic amine derivatives of the present invention may be used together with other hole transporting materials, electron transporting materials or doping materials.

The organic EL device of the present invention comprises an anode, a cathode, and one or plural organic thin film layers. In the case of one layer type, a light emitting layer as the organic thin film layer is disposed between the anode and cathode. The light emitting layer contains the light emitting material and may further contain a hole injecting material and an electron injecting material in order to effectively transport holes injected from the anode or electrons injected from the cathode to the light emitting material. The aromatic amine derivatives represented by the general formula (A), the general formula (A') or the general formula (A") have a superior light emitting property and excellent hole injecting ability and hole transporting ability as well as excellent electron injecting ability and electron transporting ability and, therefore, can be used as a light emitting material in the light emitting layer.

In the organic EL device of the present invention, the light emitting layer contains the aromatic amine derivative of the present invention in an amount of preferably 0.1 to 20% by weight and more preferably 1 to 10% by weight. Further, the aromatic amine derivatives of the present invention which are represented by the general formula (A), the general formula (A') or the general formula (A") exhibit not only an extremely high fluorescent quantum efficiency but also high hole transporting ability and electron transporting ability, and further are capable of forming a uniform thin film, so that the light emitting layer may be formed from the aromatic amine derivatives only.

On the other hand, in a case where the organic EL device of the present invention includes two or more organic thin film layers having at least the light emitting layer which are sandwiched between the cathode and anode, the organic thin film layers preferably include an organic layer containing the aromatic amine derivative represented by the general formula (A), the general formula (A') or the general formula (A") as an essential component which is disposed between the anode and the light emitting layer. Such an organic layer may be a hole injecting layer, a hole transporting layer, etc.

Examples of the organic EL device of a multilayer type include those having multilayer structures such as (an anode/a hole injecting layer/a light emitting layer/a cathode), (an anode/a light emitting layer/an electron injecting layer/a cathode) and (an anode/a hole injecting layer/a light emitting layer/an electron injecting layer/a cathode).

The light emitting layer may also optionally contain, in addition to the aromatic amine derivatives of the present invention, conventionally known materials such as light emitting materials, doping materials, hole injecting materials and electron injecting materials according to requirements. The organic EL device having such a multilayer structure can be prevented from suffering from deterioration in luminance and lifetime due to quenching. If required, the light emitting materials, doping materials, hole injecting materials and electron injecting materials may be used in combination with each other. The use of the doping materials enables the resultant device to be improved in luminance of light emission and efficiency of light emission, and further emit a red color light or a blue color light. Further, in the organic EL device of the present invention, the hole injecting layer, the light emitting layer and the electron injecting layer may respectively have a multilayer structure including two or more layers. In this case, the multi-layer hole injecting layer may include a hole injecting layer into which holes are injected from the electrode, and a hole transporting layer for accepting the holes from the hole injecting layer and transporting the holes to the light emitting layer. Also, the multi-layer electron injecting layer may include an electron injecting layer into which electrons are injected from the electrode, and an electron transporting layer for accepting the electrons from the electron injecting layer and transporting the electrons to the light emitting layer. These respective layers may be selectively used according to various factors such as energy level of the materials used, heat resistance, and adhesion to the organic thin film layers or the metal electrodes.

A light emitting material or a doping material to be used together with the aromatic amine derivatives of the present invention includes, for example, anthracene, naphthalene, phenanthrene, pyrene, tetracene, coronene, chrysene, fluorescein, perylene, phthaloperylene, naphtaloperylene, perinone, phthaloperinone, naphthaloperinone, diphenylbutadiene, tetraphenylbutadiene, coumarin, oxadiazole, aldazine, bisbenzooxazoline, bisstyryl, pyrazine, cyclopentadiene, quinolin metal complex, aminoquinolin metal complex, benzoquinolin metal complex, imine, diphenylethylene, vinylanthracene, diaminecarbazol, pyran, thiopyran, polymethyne, merocyanine, imidazol chelate oxinoid compound, quinacridone, rubrene and fluorescent dye, but not limited thereto.

The hole injecting material is preferably made of compounds which have a good hole transporting ability as well as excellent capabilities of accepting holes injected from the anode and injecting the holes into the light emitting layer or light emitting material, prevent excited particles produced in the light emitting layer from moving into the electron injecting layer or electron injecting material, and exhibit an excellent capability of forming a thin film. Specific examples of the hole injecting material include phthalocyanine derivatives, naphthalocyanine derivatives, porphyrin derivatives, oxazole, oxadiazole, triazole, imidazole, imidazolone, imidazolethione, pyrazoline, pyrazolone, tetrahydroimidazole, hydrazone, acylhydrazone, polyarylalkanes, stilbene, butadiene, benzidine-type triphenylamine, styrylamine-type triphenylamine, diamine-type triphenylamine and derivatives thereof, as well as polyvinylcarbazoles, polysilanes, and polymer materials such as electro-conductive polymers, though not particularly limited thereto.

Of these hole injecting materials usable in the organic EL device of the present invention, more effective hole injecting materials are aromatic tertiary amine derivatives and phthalocyanine derivatives.

Specific examples of the aromatic tertiary amine derivatives include triphenyl amine, tritolyl amine, tolyldiphenyl amine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cylcohexane, and oligomers and polymers having these aromatic tertiary amine skeletons, though not particularly limited thereto.

Specific examples of the phthalocyanine (Pc) derivatives include phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, GaPc-O—GaPc, as well as naphthalocyanine derivatives, though not particularly limited thereto.

Also, in the organic EL device of the present invention, between the light emitting layer and the anode, there is preferably disposed a layer containing these aromatic tertiary amine derivatives and/or phthalocyanine derivatives, such as the above hole transporting layer or hole injecting layer.

The electron injecting material is preferably made of compounds which have a good electron transporting ability as well as excellent capabilities of accepting electrons injected from the cathode and injecting the electrons into the light emitting layer or light emitting material, prevent excited particles produced in the light emitting layer from moving into the hole injecting layer, and exhibit an excellent capability of forming a thin film. Specific examples of the electron injecting material include fluorenone, lanthraquinodimethane, diphenoquinone, thiopyranedioxide, oxazole, oxadiazole, triazole, imidazole, perylenetetracarboxylic acid, fluorenylidenemethane, anthrone, and derivatives thereof, though not particularly limited thereto. Further, an electron accepting substance and an electron donating substance may be added to the hole injecting material and the electron injecting material, respectively, for enhancing sensitization thereof.

In the organic EL device of the present invention, among these electron injecting materials, more effective electron injecting materials are metal complex compounds and five-member ring derivatives containing a nitrogen atom.

Specific examples of the metal complex compounds include 8-hydroxyquinolinatolithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, and bis(2-methyl-8-quinolinato)(2-naphtholato)gallium, though not particularly limited thereto.

The five-member ring derivatives containing a nitrogen atom are preferably derivatives of oxazole, thiazole, oxadiazole, thiadiazole or triazole. Specific examples of the five-member ring derivative containing a nitrogen atom include 2,5-bis(1-phenyl)-1,3,4-oxazole, dimethyl POPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis [2-(5-phenyloxadiazolyl)]benzene, 1,4-bis [2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole, and 1,4-bis[2-(5-phenyltriazolyl)]benzene, though not particularly limited thereto.

In the organic EL device of the present invention, the light emitting layer may also optionally contain at least one material selected from the group consisting of light emitting materials, doping materials, hole injecting materials and electron injecting materials, in addition to the aromatic amine derivatives represented by at least one selected from the general formula (A), the general formula (A') and the general formula (A"). The organic EL device of the present invention may be further provided on a surface thereof with a protective layer, or the whole part thereof may be protected with silicone oil, resins, etc., in order to enhance stability thereof against temperature, humidity, atmosphere, etc.

The anode of the organic EL device according to the present invention may be suitably made of an electro-conductive material having a work function more than 4 eV. Examples of the electro-conductive material for the anode include carbon, aluminum, vanadium, iron, cobalt, nickel, tungsten, silver, gold, platinum, palladium and alloys thereof, metal oxides such as tin oxide and indium oxide which are used for ITO substrates or NESA substrates, and organic electro-conductive resins such as polythiophene and polypyrrole. The cathode of the organic EL device according to the present invention may be suitably made of an electro-conductive material having a work function of 4 eV or smaller. Examples of the electro-conductive material for the cathode include magnesium, calcium, tin, lead, titanium, yttrium, lithium, ruthenium, manganese, aluminum, lithium fluoride and alloys thereof, though not particularly limited thereto. Typical examples of the alloys include alloys of magnesium and silver, alloys of magnesium and indium, and alloys of lithium and aluminum, though not particularly limited thereto. The ratio between the constituting metals in the alloys may be controlled and appropriately determined depending upon a temperature and an atmosphere of vapor deposition sources or vacuum degree, etc. The anode and cathode may be constituted of two or more layers, if required.

At least one surface of the organic EL device of the present invention preferably exhibits a sufficient transparency in a wavelength range of light emitted therefrom in order to enhance an efficiency of light emission thereof. Further, the substrate for the device is also preferably transparent. The transparent electrode is formed using the above electro-conductive material by vapor deposition process, sputtering process, etc., so as to ensure a desirable transparency thereof. The electrode disposed on a light emitting surface of the device preferably has a light transmittance of 10% or greater. The substrate is not particularly limited as long as it suitably has a good mechanical and thermal strength as well as a good transparency. Examples of the substrate include glass substrates and transparent resin films. Specific examples of the transparent resin films include films made of polyethylene, ethylene-vinylacetate copolymer, ethylene-vinylalcohol copolymer, polypropylene, polystyrene, polymethylmethacrylate, polyvinylchloride, polyvinyl alcohol, polyvinylbutyral, nylons, polyether ether ketones, polysulfones, polyether sulfones, tetrafluoroethylene-perfluoroalkylvinyl ether copolymer, polyvinyl fluoride, tetrafluoroethylene-ethylene copolymer, tetrafluoroethylene-hexafluoropropylene copolymer, polychlorotrifluoroethylene, polyvinylidene fluoride, polyesters, polycarbonates, polyurethanes, polyimides, and polyether imides.

The respective layers of the organic EL device of the present invention may be formed by either a dry film-forming process such as vacuum vapor deposition, sputtering, plasma and ion-plating, or a wet film-forming process such as spin-coating, dipping and flow-coating. The thickness of the respective layers is not particularly limited, but should be adjusted to an appropriate range. When the thickness is too large, a large electric voltage must be applied to the device in order to achieve a predetermined light output, resulting in a poor efficiency of light emission. On the other hand, when the thickness is too small, pinholes tend to be formed in the layers, thereby failing to obtain a sufficient luminance of light emission even upon applying an electric field thereto. The suitable thickness of the respective layers is usually in the range of from 5 nanometers to 10 μm and preferably from 10 nanometers to 0.2 μm.

In the wet film-forming process, materials constituting the respective layers are dissolved or dispersed in a suitable solvent such as ethanol, chloroform, tetrahydrofuran and dioxane to form a thin film thereof. The solvent used for forming the respective layers is not particularly limited. Also, suitable resins or additives may be added to the respective organic thin film layers for purposes of improving a film-forming property, preventing formation of pinholes in the resultant film, etc. Examples of the resins usable for the above purposes include insulating resins such as polystyrene, polycarbonates, polyarylates, polyesters, polyamides, polyurethanes, polysulfones, polymethylmethacrylate, polymethylacrylate and celluloses as well as copolymers thereof, photo-electric conductive resins such as poly-N-vinyl carbazole and polysilanes, and electro-conductive resins such as polythiophene and polypyrrole. Examples of the additives include antioxidants, ultraviolet absorbers and plasticizers.

As described above, employing the aromatic amine derivative of the present invention for the organic thin film layer of the organic EL device enables to realize an organic EL device having a prolonged lifetime and an enhanced efficiency of light emission.

The organic EL device of the present invention is suitably applied to, for example, flat light-emitting members such as a wall-type TV flat panel displays; backlight for copiers, printers and liquid crystal displays; or light sources for measuring equipments; display panels, beacon light, etc. Further, the material of the present invention can be used not only for organic EL devices but also in other applications such as electronic photographic photosensitive articles, photoelectric converter elements, solar cells, image sensors, etc.

Following is a description regarding a process for producing the aromatic amine derivative of the present invention. A process for preparing 3,8-dihalogeno-1,6-substituted pyrene employed for the process of the present invention is selectable from well known process without particularly specified, and may be introduced, for example, from the description in Journal of Materials Chemistry, 2000, 10, pp 315-319 (Ken-ichi Sugiura et al.), etc.

Namely, 3,8-dihalogeno-1,6-substituted pyrene represented by a following general formula (1) is prepared by halogenating 1,6-substituted pyrene represented by a following general formula (0):

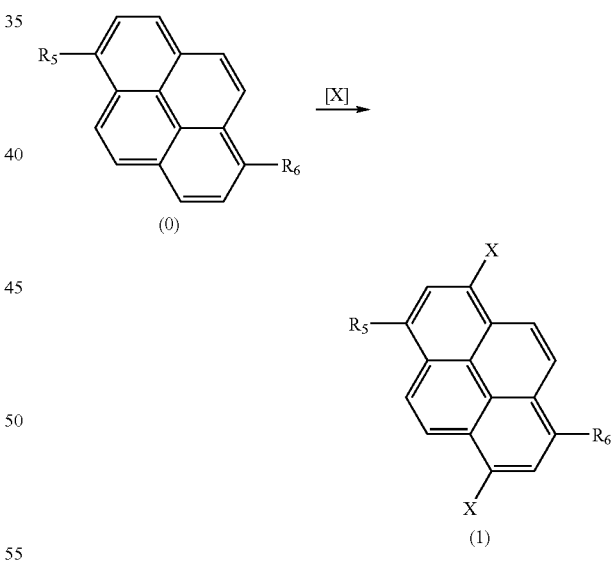

Examples of a halogen atom employed for halogenating, namely, the halogen atom represented by X in the general formula (1) include fluorine atom, chlorine atom, bromine atom, iodine atom and so on, bromine (Br) atom and iodine (I) atom being preferable.

In the general formulae (0) and (1), $R_5$ and $R_6$ each independently represents a substituted or unsubstituted alkyl group having 1 to 50 carbon atoms, a substituted or unsubstituted aryl group having 5 to 50 carbon atoms, a substituted or unsubstituted aralkyl group having 7 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a halogen atom, cyano group or a silyl group.

Examples of the alkyl group represented by the above $R_5$ or $R_6$ include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxy-isopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triamino-propyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, cyclopropyl group, cyclobutyl group, cyclopentyl group, cyclohexyl group, 4-methylcyclohexyl group, 1-adamantyl group, 2-adamantyl group, 1-norbornyl group, 2-norbornyl group, substituted or unsubstituted perfluoroalkyl group having 1 to 10 carbon atoms, etc.

Examples of the aryl group represented by the above $R_5$ or $R_6$ include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group and 4''-t-butyl-p-terphenyl-4-yl group, etc.

Examples of the aralkyl group represented by the above $R_5$ or $R_6$ include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, 1-chloro-2-phenylisopropyl group, etc.

Examples of the cycloalkyl group represented by the above $R_5$ or $R_6$ include cyclopropyl group, cyclobutyl group, cyclopentyl group, cyclohexyl group, etc.

Examples of the alkoxyl group represented by the above $R_5$ or $R_6$ include methoxy group, ethoxy group, propoxy group, isopropoxy group, butoxy group, isobutoxy group, sec-butoxy group, tert-butoxy group, various pentyloxy groups, various hexyloxy groups, etc.

Examples of the aryloxy group represented by the above $R_5$ or $R_6$ include phenoxy group, tolyloxy group, naphthyloxy group, etc.

Examples of the halogen atom represented by the above $R_5$ and $R_6$ include fluorine atom, chlorine atom, bromine atom and iodine atom, etc.

Examples of the substituent for each group represented by $R_5$ or $R_6$ include an alkyl group having 1 to 6 carbon atoms, a cycloalkyl group having 3 to 6 carbon atoms, an alkoxyl group having 1 to 6 carbon atoms, an aryloxy group having 5 to 18 carbon atoms, an aralkyloxy group having 7 to 18 carbon atoms, an arylamino group having 5 to 16 carbon atoms, a nitro group, a cyano group, an ester group having 1 to 6 carbon atoms, a halogen atom, etc.

A process for preparing 1,6-substituted pyrene represented by the general formula (0) is selectable from well known process without particularly specified, and may be introduced, for example, from 1,6-dibromo pyrene [Journal of Chemical Society Perkin, Vol. 1, page 1622 (1972)], etc.

When a halogen atom used in the halogenation is bromine atom, examples of a reagent employed for halogenation of 1,6-substituted pyrene represented by the general formula (O) include bromine, N-bromosuccinimide (NBS), KBr, $KBrO_3$, $AlBr_3$, $PBr_3$, $SbBr_3$, $FeBr_2$, $PyHBrCl_2$, $Bu_4NBr_3$ and so on while bromine and NBS are preferable. When the halogen atom used in the halogenation is except bromine atom, the above examples whose bromine atom is replaced with the halogen atom are applicable.

Regarding with the halogenation, it is preferable to be carried out among an organic solvent or a sulfuric acid such as carbon tetrachloride, chloroform, methylene chloride, acetic acid, pyridine, dimethylformamide (DMF), etc. Moreover, a peroxide such as benzoyl peroxide (BPO), 2,2'-azobisisobutyronitrile (AIBN), m-chloroperbenzoic acid (mCPBA) or so and a heavy metal salt may be added to the halogenation reaction process, and a light irradiation may be carried out during the process.

With regard to a reaction temperature for the halogenation, it is usually within a range of from a room temperature to 150° C. and preferably within a range of from the room temperature to 100° C. With regard to a reaction time for the halogenation, it is usually within a range of from 1 to 120 hours, preferably within a range of from 6 to 18 hours.

The present invention provides a process for producing an aromatic amine derivative represented by a following general formula (2) by aminating 3,8-dihalogeno-1,6-substituted pyrene represented by a following general formula (1):

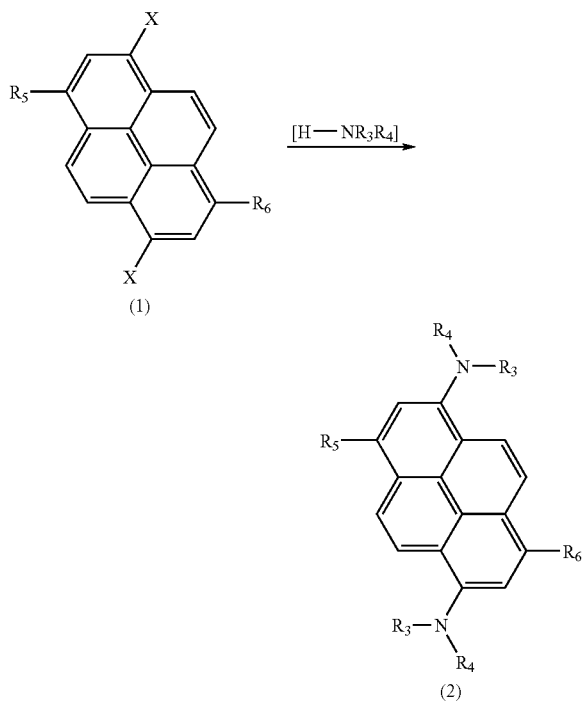

(1)

(2)

In the general formulae (1) and (2), $R_5$ and $R_6$ each independently represent the same as aforementioned.

X in the general formula (1) represents a halogen atom; and $R_3$ and $R_4$ in the general formula (2) each independently represents a substituted or unsubstituted aryl group having 5 to 50 carbon atoms or a substituted or unsubstituted alkyl group having 1 to 20 carbon atoms, a substituted or unsubstituted aryl group being preferable.

Examples of the aryl group represented by $R_3$ and $R_4$ are the same as those about the foregoing $R_1$ and $R_2$.

Examples of the alkyl group represented by $R_3$ and $R_4$ are the same as those about the foregoing $R_1$ and $R_2$.

It is preferable that the general formula (2) coincides with an aromatic amine derivative represented by a following general formula (3).

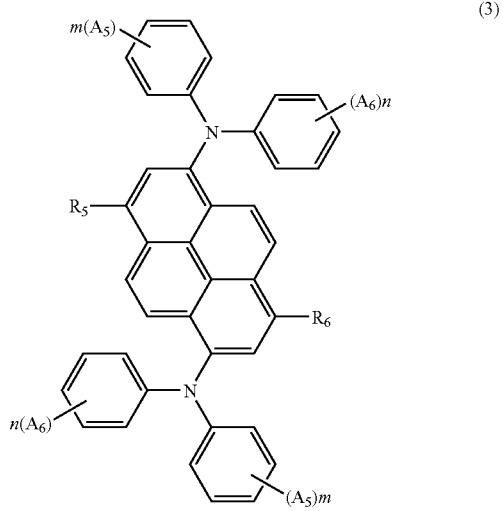

(3)

In the general formula (3), $R_5$ and $R_6$ each independently represents the same as aforementioned.

In the general formula (3), $A_5$ and $A_6$ each independently represents a hydrogen atom, a substituted or unsubstituted alkyl group having 1 to 10 carbon atoms, a substituted or unsubstituted aryl group having 5 to 50 carbon atoms, a substituted or unsubstituted aralkyl group having 7 to 50 carbon atoms, a substituted or unsubstituted cycloalkyl group having 3 to 20 carbon atoms, a substituted or unsubstituted alkoxyl group having 1 to 10 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 10 carbon atoms, or a halogen atom. Specific examples of those groups include the same whose numbers of carbon atoms coincide with those described about the foregoing $R_1$ and $R_2$.

In the general formula (3), m and n each independently represents an integer of 1 to 5; when m or n is 2 or greater, plural $A_5$ or plural $A_6$ may be the same with, or different from each other, or may bond each other to form a saturated or unsaturated ring.

Examples of the saturated or unsaturated ring are the same as those explained about the foregoing aryl group and the foregoing cycloalkyl group.

In the present invention, it is preferable to employ a transition metal as a catalyst in an occasion of aminating 3,8-dihalogeno-1,6-substituted pyrene represented by the general formula (1).

Examples of the transition metal include manganese (Mn), iron (Fe), cobalt (Co), nickel (Ni), copper (Cu), palladium (Pd), molybdenum (Mo), rhodium (Rh), ruthenium (Ru), vanadium (V), chromium (Cr), platinum (Pt) and iridium (Ir). Among those, Ni, Pd, Pt and Cu are preferable and Pd and Cu are more preferable.

Those transition metals are preferably used as minute powder of the transition metal by itself singly, as a metal transition complex, as a transition metal compound or so.

When the transition metal is used as the transition metal complex, examples of the transition metal complex include acetylacetonate complex, acetate complex, phosphine complex, diphosphine complex, Schiff base complex, porphyrin complex and so on; phosphine complex and diphosphine complex being preferable.

Following is description about a reaction condition when the transition metal is used as the transition metal complex.

The complex corresponding to a catalyst may be prepared beforehand or may be generated among the reaction system. With regard to the addition amount of the transition metal complex, it is usually 0.001 to 1 equivalent and is preferably 0.01 to 0.1 equivalent each for 3,8-dihalogeno-1,6-substituted pyrene as the material respectively.

An amination reaction in an occasion of using the transition metal complex as the catalyst will be carried out with a use of a base, and sodium-t-butoxide, cesium carbonate, potassium phosphate and so on will be preferable as the base. Particularly, sodium-t-butoxide and cesium carbonate are more preferable.

With regard to the addition amount of the base, it is usually 1 to 2 equivalent and is preferably 1 to 1.2 equivalent each for a halogen atom bonding to 3,8-dihalogeno-1,6-substituted pyrene.

With regard to the reaction solvent, employable are ether, tetrahydrofuran (THF), dioxane, dimethylformamide (DMF), toluene, xylene, etc. Among those, toluene and xylene are preferable. It is desirable that those solvent are dehydrated and/or substituted with an inert gas.

A process for dehydrating the solvent and/or substituting it with an inert gas is in accordance with usually popular processes in the field of organic synthesis. Examples include throwing desiccant such as calcium chloride or so into the solvent, or distillation of the solvent among a gas flow of nitrogen, argon or so under the presence of calcium hydride or metallic sodium, etc.

With regard to a reaction temperature for the amination, it is usually within a range of from a room temperature to 150° C. and preferably within a range of from 50 to 100° C. With regard to a reaction time for the amination, it is usually within a range of from 1 to 48 hours, preferably within a range of from 6 to 18 hours.

Further, it is preferable that the aminating reaction should be carried out among an ambient atmosphere of an inert gas including preparation of the catalyst.

Furthermore, when the above transition metals are used as the transition metal complex compounds, examples of the transition metal complex compound include halide, oxide, chalcogenide compound and so on, halide being preferable. Examples of halide include fluoride, chloride, bromide, iodide and so on, bromide and iodide being particularly preferable. It is preferable that the transition metal compound is 0 valent or monovalent.

Following is description about a reaction condition when the transition metal is used as the transition metal compound.

With regard to the addition amount of the transition metal complex compound, it is usually 0.01 to 1 equivalent and is preferably 0.1 to 0.5 equivalent each for 3,8-dihalogeno-1,6-substituted pyrene as the material respectively.

An amination reaction in an occasion of using the transition metal complex compound as the catalyst will be carried out with a use of a base, and hydroxide and salt of alkali metal or alkaline earth metal will be practical as the base, hydroxide, carbonate, hydrogencarbonate and acetate are preferable and hydroxide is particularly preferable.

With regard to the addition amount of the base, it is usually 2 to 5 equivalent and is preferably 2 to 3 equivalent each for a halogen atom bonding to 3,8-dihalogeno-1,6-substituted pyrene.

With regard to the reaction solvent, employable is a solvent with high boiling point such as xylene, decalin, dioxane, dimethylformamide (DMF), dimethylsulfoxide (DMSO), etc. Among those, xylene and decalin are preferable. It is desirable that those solvent are dehydrated and/or substituted with an inert gas.

A process for dehydrating the solvent and/or substituting it with an inert gas is in accordance with usually popular processes in the field of organic synthesis. Examples include throwing desiccant such as calcium chloride or so into the solvent, or distillation of the solvent among a gas flow of nitrogen, argon or so under the presence of calcium hydride or metallic sodium, etc.

With regard to a reaction temperature for the amination, it is usually within a range of from a room temperature to 150° C. and preferably within a range of from 100 to 150° C. With regard to a reaction time for the amination, it is usually within a range of from 1 to 48 hours, preferably within a range of from 6 to 18 hours.

Further, it is preferable that the aminating reaction should be carried out among an ambient atmosphere of an inert gas including preparation of the catalyst. The aromatic amine derivative represented by the general formula (2) produced in accordance with the process of the present invention is favorably appropriate as a charge transporting material for electronic photographic photosensitive articles or as a material for an organic EL device, and particularly, as a hole transporting material, as a light emitting material and as a doping material.

EXAMPLES

This invention will be described in further detail with reference to Examples, which does not limit the scope of this invention.

Additionally in Synthesis Examples below, the $^1$H-NMR spectra were obtained by means of DRX-500 (Trade name; produced by Brucker Optics Inc.).

Synthesis Example 1

Synthesis of Compound (D-3)

Under an atmospheric argon gas flow, 1,6-dimethyl-3,8-dibromopyrene in an amount of 3.0 g (7.7 millimole), m,m-ditolylamine in an amount of 3.4 g (18.5 millimole), palladium acetate in an amount of 0.03 g (1.5% by mole), tri-t-butylphosphine in an amount of 0.05 g (3% by mole), sodium-t-butoxide in an amount of 1.8 g (18.7 millimole) and dried toluene in an amount of 50 milliliter were placed into a three-neck flask equipped with a cooling pipe and having a capacity of 300 milliliter, and the resultant solution was stirred with heating at a temperature of 110° C. for 8 hours. After the completion of the reaction, the resultant solution was passed through a silicagel short column, and after concentrating under a reduced pressure, a precipitated crystal was separated by filtration. The crystal washed with the use of 50 milliliter of toluene and 100 milliliter of methanol, and as a result, 4.5 g of pale yellow powder was obtained. The pale yellow powder was identified as Compound (D-3) from the result of $^1$H-NMR spectrum (refer to FIG. 1) and Field Desorption Mass Spectrum (FD-MS) measurement (the yield: 98%).

[Peak absorption wavelength: 430 nanometers, Greatest fluorescent wavelength: 460 nanometers (toluene solution)]

Synthesis Example 2

Synthesis of Compound (D-38)

(1) Synthesis of Intermediate Material (1,6-diisopropylpyrene)

Under an atmospheric argon gas flow, 1,6-dibromopyrene in an amount of 20 g (55.6 millimole), isopropylmagnesiumbromide in an amount of 117 milliliter [117 millimole, 1 mole/liter (THF: tetrahydrofuran)], (diphenylphosphino ferrocene)palladium(II)dichloride in an amount of 2.27 g (5% by mole) and dried dioxane in an amount of 130 milliliter were placed into a three-neck flask equipped with a cooling pipe and having a capacity of 500 milliliter, and the resultant solution was stirred with heating at a temperature of 90° C. for 8 hours. After the completion of the reaction, adding 100 milliliter of dilute hydrochloric acid, an organic layer was separated and concentrated under a reduced pressure. Then, the organic layer was passed through a silicagel short column, and after concentrating under the reduced pressure again, a precipitated crystal was separated by filtration and as a result, 7.4 g of 1,6-diisopropyl pyrene (pale yellow powder) was obtained (the yield: 31%).

(2) Synthesis of Intermediate Material (1,6-diisopropyl-3,8-dibromopyrene)

Figure 2:
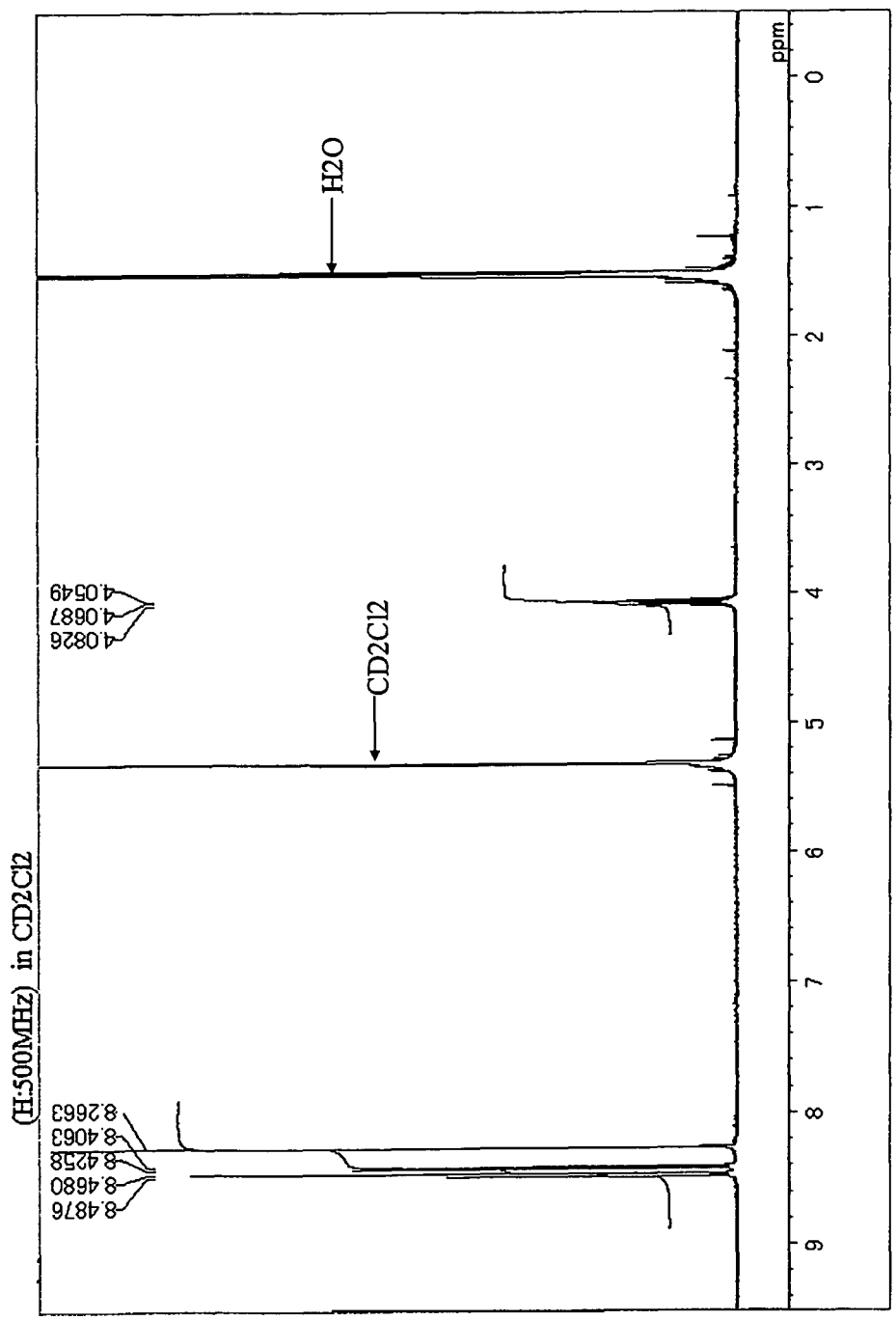
FIG. 2 is a chart showing a result of NMR measurement about 1,6-diisopropyl-3,8-dibromopyrene which is an intermediate material for Compound (D-38) as the aromatic amine derivative of the present invention.

Under an atmospheric argon gas flow, 1,6-diisopropylpyrene in an amount of 7.4 g (25.9 millimole), N-bromosuccinimide in an amount of 11 g (62.1 millimole) and dried dimethylformamide (DMF) in an amount of 250 milliliter were placed into an eggplant flask equipped with a cooling pipe and having a capacity of 1 liter, and the resultant solution was stirred with heating at a temperature of 50° C. for 4 hours. After the completion of the reaction, adding 250 milliliter of water, precipitated crystals were separated by filtration and washed with the use of 50 milliliter of water and 100 milliliter of methanol, and as a result, 3.2 g of pale yellow powder was obtained (the yield: 28%). The pale yellow powder was identified as 1,6-diisopropyl-3,8-dibromopyrene from the result of $^1$H-NMR spectrum (refer to FIG. 2) and FD-MS measurement.

(3) Synthesis of Compound (D-38)

Figure 3:
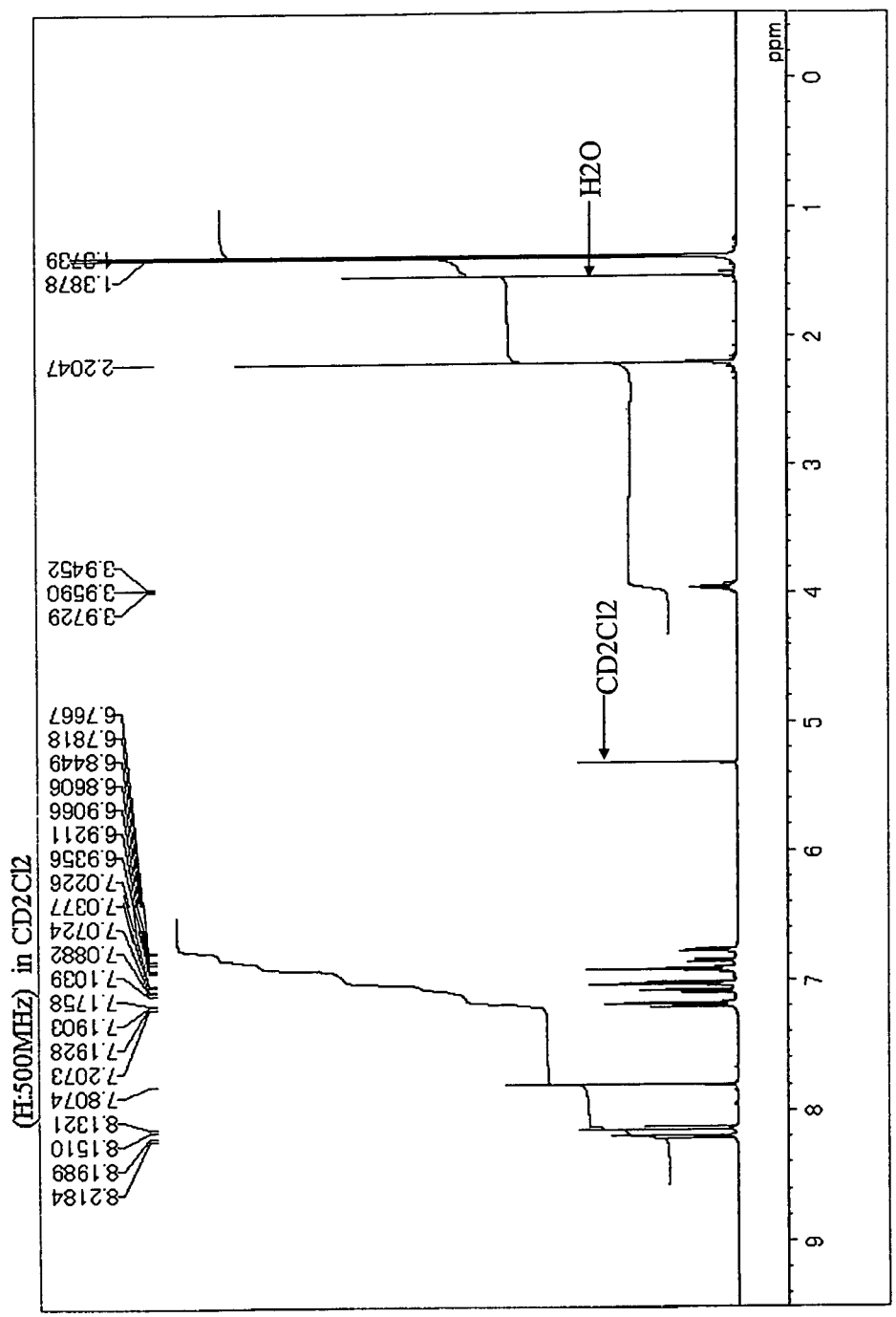
FIG. 3 is a chart showing a result of NMR measurement about Compound (D-38) as the aromatic amine derivative of the present invention.

Under an atmospheric argon gas flow, 1,6-diisopropyl-3,8-dibromopyrene in an amount of 3.0 g (6.7 millimole), 4-methyldiphenylamine in an amount of 3.0 g (16.5 millimole), palladium acetate in an amount of 0.02 g (1.5% by mole), tri-t-butylphosphine in an amount of 0.04 g (3% by mole), sodium-t-butoxide in an amount of 1.6 g (16.6 millimole) and dried toluene in an amount of 50 milliliter were placed into a three-neck flask equipped with a cooling pipe and having a capacity of 300 milliliter, and the resultant solution was stirred with heating at a temperature of 110° C. for 8 hours. After the completion of the reaction, the resultant solution was passed through a silicagel short column, and after concentrating under a reduced pressure, a precipitated crystal was separated by filtration. The crystal washed with the use of 50 milliliter of toluene and 100 milliliter of methanol, and as a result, 4.3 g of pale yellow powder was obtained. The pale yellow powder was identified as Compound (D-38) from the result of $^1$H-NMR spectrum (refer to FIG. 3) and FD-MS measurement (the yield: 98%).
[Peak absorption wavelength: 427 nanometers, Greatest fluorescent wavelength: 459 nanometers (toluene solution)]

Synthesis Example 3

Synthesis of Compound (D-39)

Figure 4:
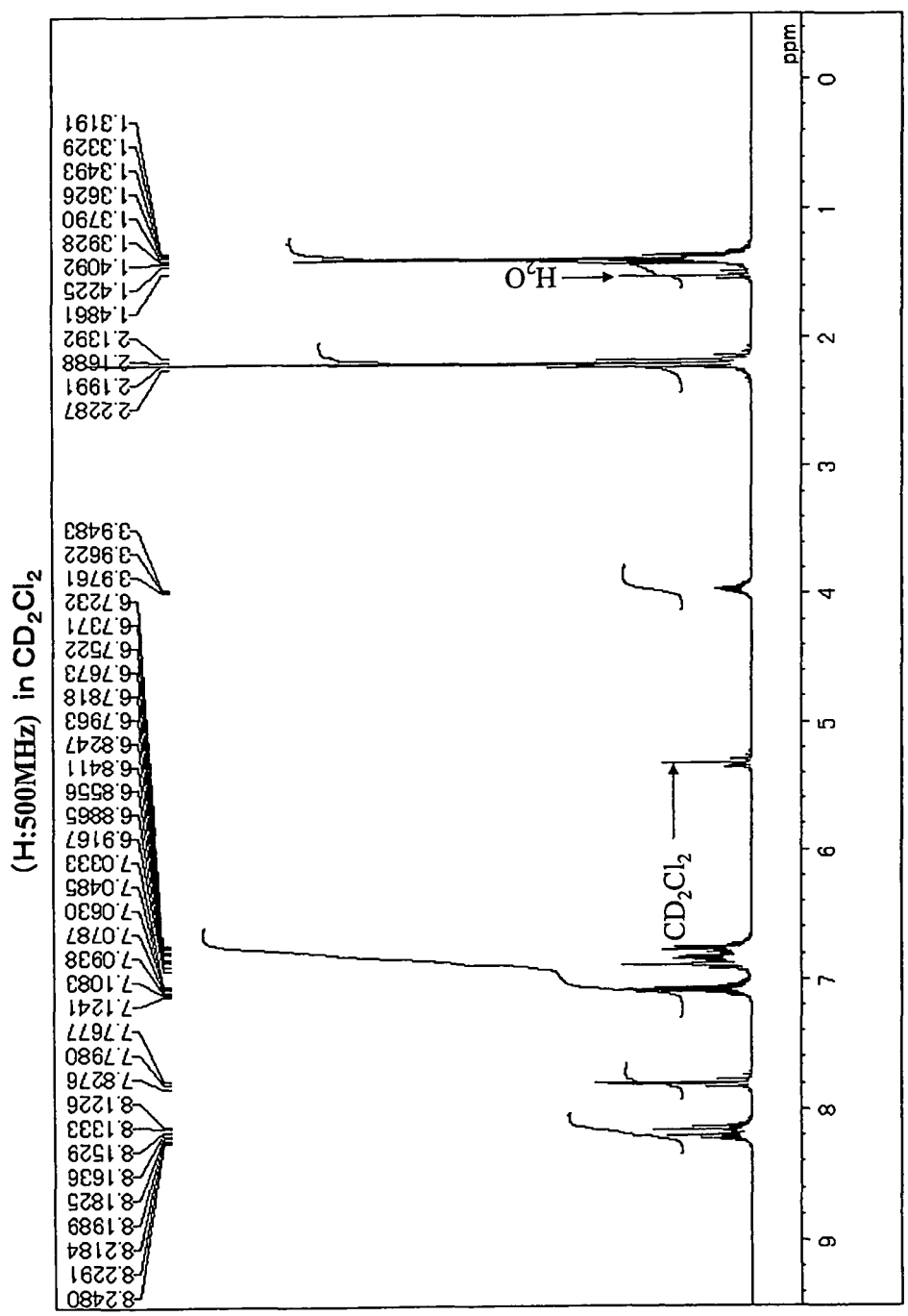
FIG. 4 is a chart showing a result of NMR measurement about Compound (D-39) as the aromatic amine derivative of the present invention.

Under an atmospheric argon gas flow, 1,6-diisopropyl-3,8-dibromopyrene in an amount of 3.0 g (6.7 millimole), m,m'-ditolylamine in an amount of 3.2 g (16.2 millimole), palladium acetate in an amount of 0.02 g (1.5% by mole), tri-t-butylphosphine in an amount of 0.04 g (3% by mol), sodium-t-butoxide in an amount of 1.6 g (16.6 millimole) and dried toluene in an amount of 75 milliliter were placed into a three-neck flask equipped with a cooling pipe and having a capacity of 300 milliliter, and the resultant solution was stirred with heating at a temperature of 110° C. for 8 hours. After the completion of the reaction, the resultant solution was passed through a silicagel short column, and after concentrating under a reduced pressure, a precipitated crystal was separated by filtration. The crystal washed with the use of 50 milliliter of toluene and 100 milliliter of methanol, and as a result, 4.5 g of pale yellow powder was obtained. The pale yellow powder was identified as Compound (D-39) from the result of $^1$H-NMR spectrum (refer to FIG. 4) and FD-MS measurement (the yield: 98%).
[Peak absorption wavelength: 429 nanometers, Greatest fluorescent wavelength: 463 nanometers (toluene solution)]

Synthesis Example 4

Synthesis of Compound (D-40)

Figure 5:
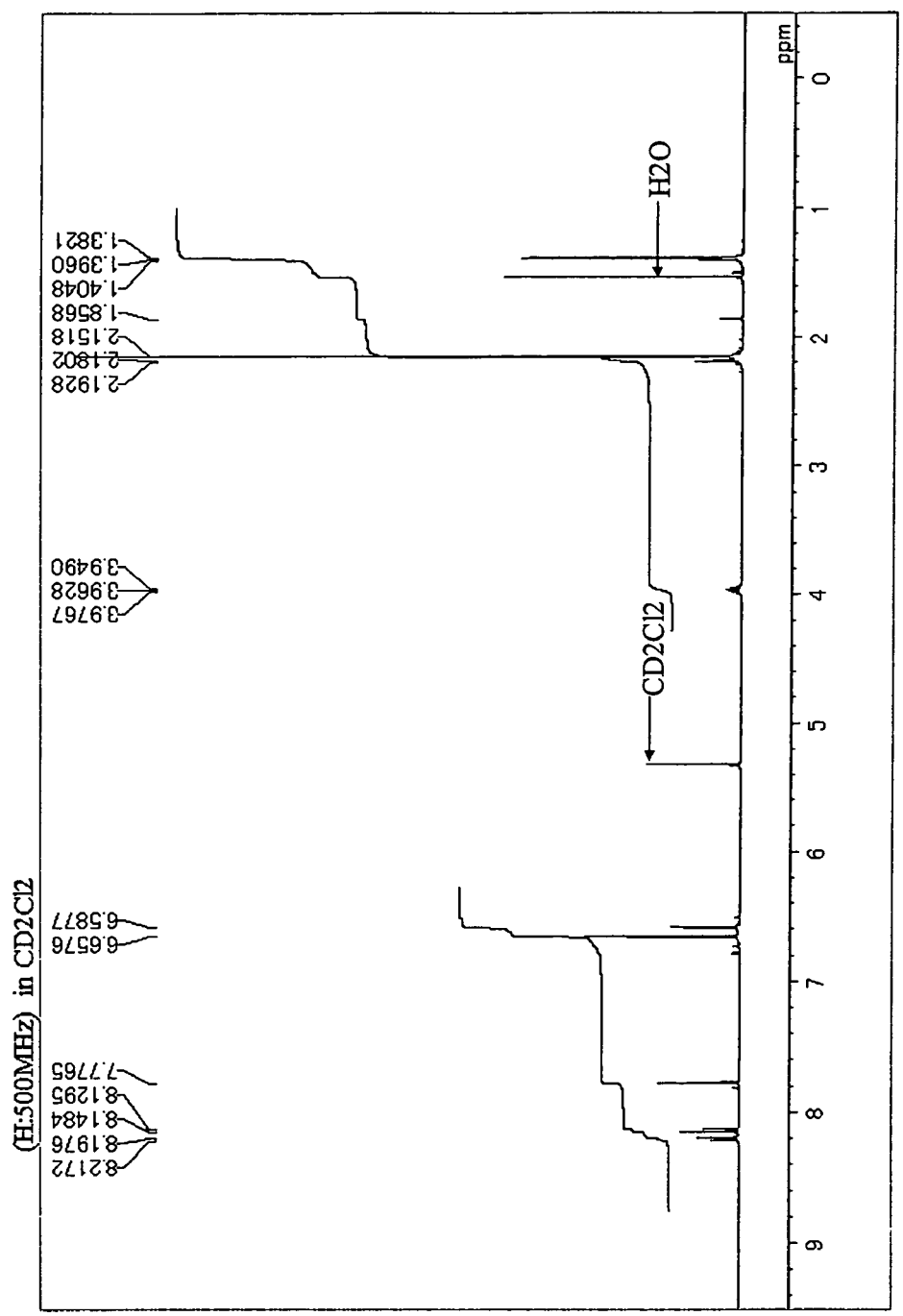
FIG. 5 is a chart showing a result of NMR measurement about Compound (D-40) as the aromatic amine derivative of the present invention.

Under an atmospheric argon gas flow, 1,6-diisopropyl-3,8-dibromo pyrene in an amount of 2.5 g (5.6 millimole), bis(3,5-dimethylphenyl)amine in an amount of 3.0 g (13.4 millimole), palladium acetate in an amount of 0.02 g (1.5% by mole), tri-t-butylphosphine in an amount of 0.04 g (3% by mole), sodium-t-butoxide in an amount of 1.3 g (13.5 millimole) and dried toluene in an amount of 50 milliliter were placed into a three-neck flask equipped with a cooling pipe and having a capacity of 300 milliliter, and the resultant solution was stirred with heating at a temperature of 110° C. for 8 hours. After the completion of the reaction, precipitated crystals were separated by filtration and washed with the use of 50 milliliter of methylene chloride and 100 milliliter of methanol, and as a result, 3.9 g of pale yellow powder was obtained. The pale yellow powder was identified as Compound (D-40) from the result of $^1$H-NMR spectrum (refer to FIG. 5) and FD-MS measurement (the yield: 95%).
[Peak absorption wavelength: 434 nanometers, Greatest fluorescent wavelength: 465 nanometers (toluene solution)]

Synthesis Example 5

Synthesis of Compound (D-77)

Figure 6:
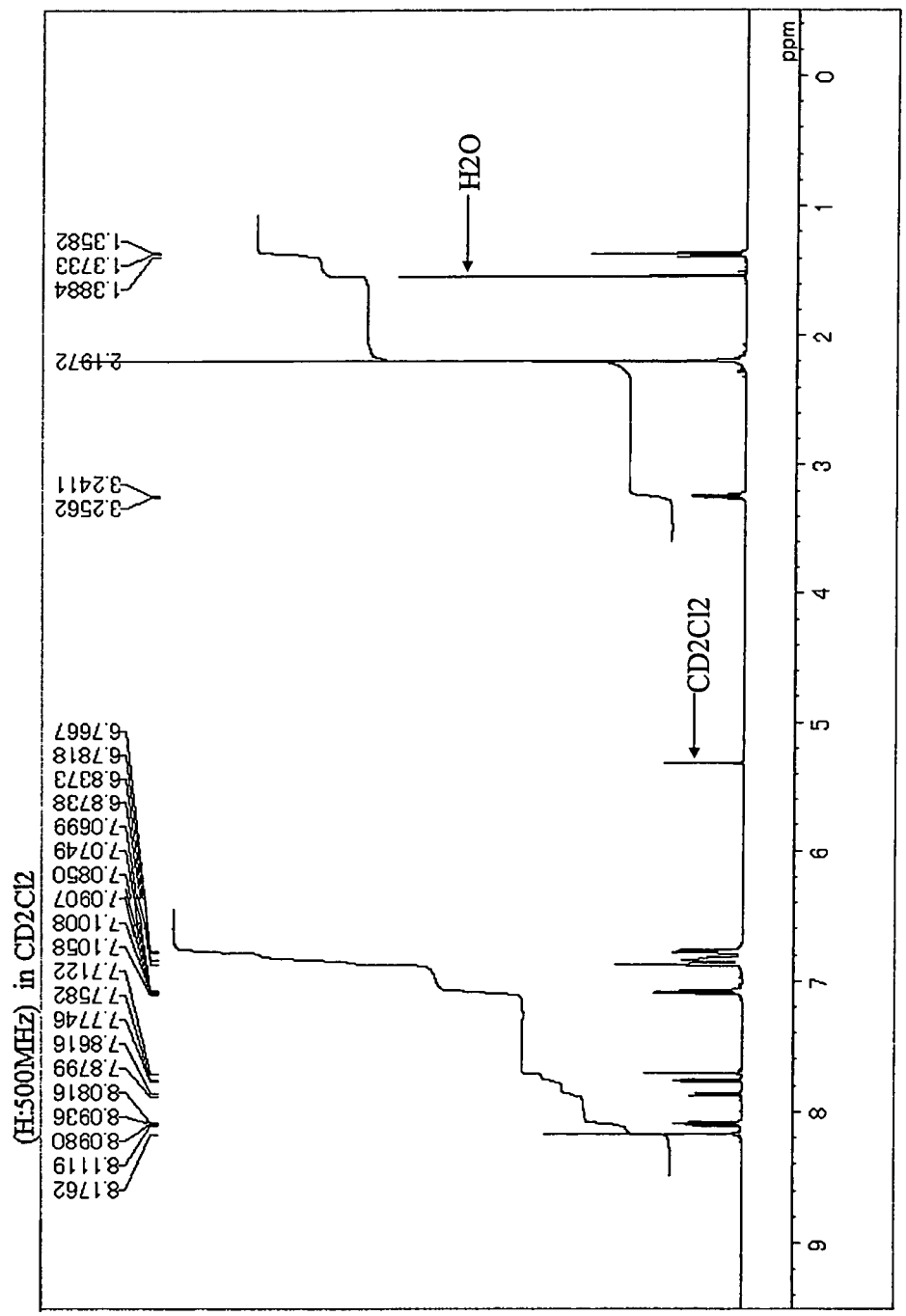
FIG. 6 is a chart showing a result of NMR measurement about Compound (D-77) as the aromatic amine derivative of the present invention.

Under an atmospheric argon gas flow, 1-ethyl-3,8-dibromopyrene in an amount of 2.5 g (6.4 millimole), m,m'-ditolylamine in an amount of 3.0 g (15.2 millimole), palladium acetate in an amount of 0.02 g (1.5% by mole), tri-t-butylphosphine in an amount of 0.04 g (3% by mol), sodium t-butoxide in an amount of 1.5 g (15.6 millimole) and dried toluene in an amount of 50 milliliter were placed into a three-neck flask equipped with a cooling pipe and having a capacity of 300 milliliter, and the resultant solution was stirred with heating at a temperature of 110° C. for 8 hours. After the completion of the reaction, the resultant solution was passed through a silicagel short column, and after concentrating under the reduced pressure, a precipitated crystal was separated by filtration. The crystal washed with the use of 50 milliliter of toluene and 100 milliliter of methanol, and as a result, 3.9 g of pale yellow powder was obtained. The pale yellow powder was identified as Compound (D-77) from the result of $^1$H-NMR spectrum (refer to FIG. 6) and FD-MS measurement (the yield: 97%).
[Peak absorption wavelength: 430 nanometers, Greatest fluorescent wavelength: 460 nanometers (toluene solution)]

Synthesis Example 6

Synthesis of Compound (D-78)

Figure 7:
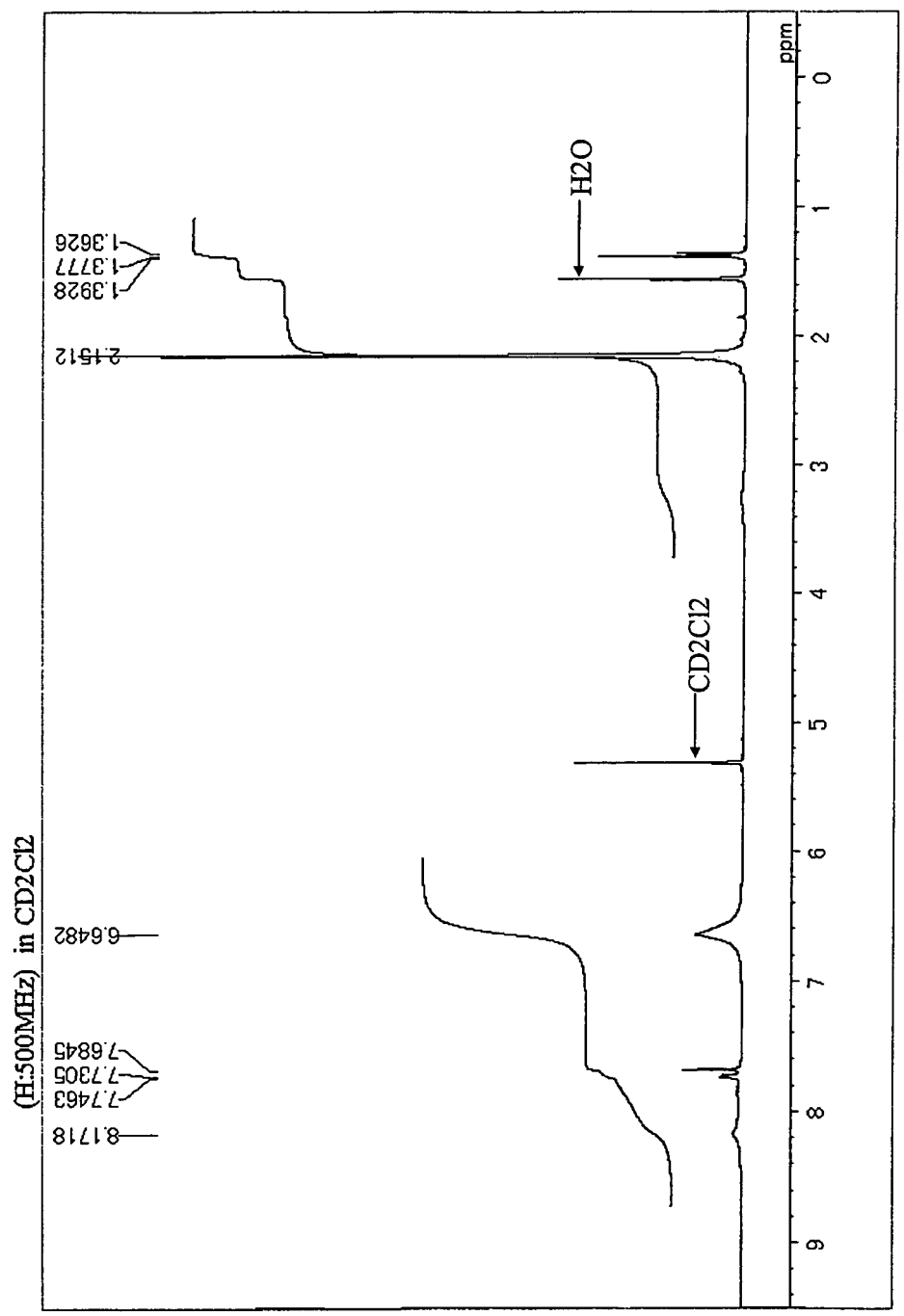
FIG. 7 is a chart showing a result of NMR measurement about Compound (D-78) as the aromatic amine derivative of the present invention.

Under an atmospheric argon gas flow, 1-ethyl-3,8-dibromopyrene in an amount of 2.5 g (6.4 millimole), bis(3,5-dimethylphenyl)amine in an amount of 3.5 g (15.5 millimole), palladium acetate in an amount of 0.02 g (1.5% by mole), tri-t-butylphosphine in an amount of 0.04 g (3% by mole), sodium-t-butoxide in an amount of 1.5 g (15.6 millimole) and dried toluene in an amount of 50 milliliter were placed into a three-neck flask equipped with a cooling pipe and having a capacity of 300 milliliter, and the resultant solution was stirred with heating at a temperature of 110° for 8 hours. After the completion of the reaction, precipitated crystal was separated by filtration and washed with the use of 50 milliliter of toluene and 100 milliliter of methanol, and as a result, 2.7 g of pale yellow powders were obtained. The pale yellow powder was identified as Compound (D-78) from the result of $^1$H-NMR spectrum (refer to FIG. 7) and FD-MS measurement (the yield: 62%).

[Peak absorption wavelength: 435 nanometers, Greatest fluorescent wavelength: 466 nanometers (toluene solution)]

Synthesis Example 7

Synthesis of Compound (D-83)

(1) Synthesis of Intermediate Material
(1,6-dicyclohexylpyrene)

Under an atmospheric argon gas flow, 1,6-dibromopyrene in an amount of 20 g (55.6 millimole), cyclohexylmagnesiumbromide in an amount of 117 milliliter [117 millimole, 1 mole/liter (THF: tetrahydrofuran)], (diphenylphosphinoferrocene)palladium(II)dichloride in an amount of 2.27 g (5% by mole), dried dioxane in an amount of 80 milliliter and THF in an amount of 70 milliliter were placed into a three-neck flask equipped with a cooling pipe and having a capacity of 500 milliliter, and the resultant solution was stirred with heating at a temperature of 90° C. for 8 hours. After the completion of the reaction, adding 100 milliliter of dilute hydrochloric acid, an organic layer was separated and concentrated under a reduced pressure. Then, the organic layer was passed through a silicagel short column, and after concentrating under the reduced pressure again, a precipitated crystal was separated by filtration and as a result, 7.0 g of 1,6-dicyclohexylpyrene (pale yellow powder) was obtained (the yield: 71%).

(2) Synthesis of Intermediate Material
(1,6-dicyclohexyl-3,8-dibromopyrene)

Figure 8:
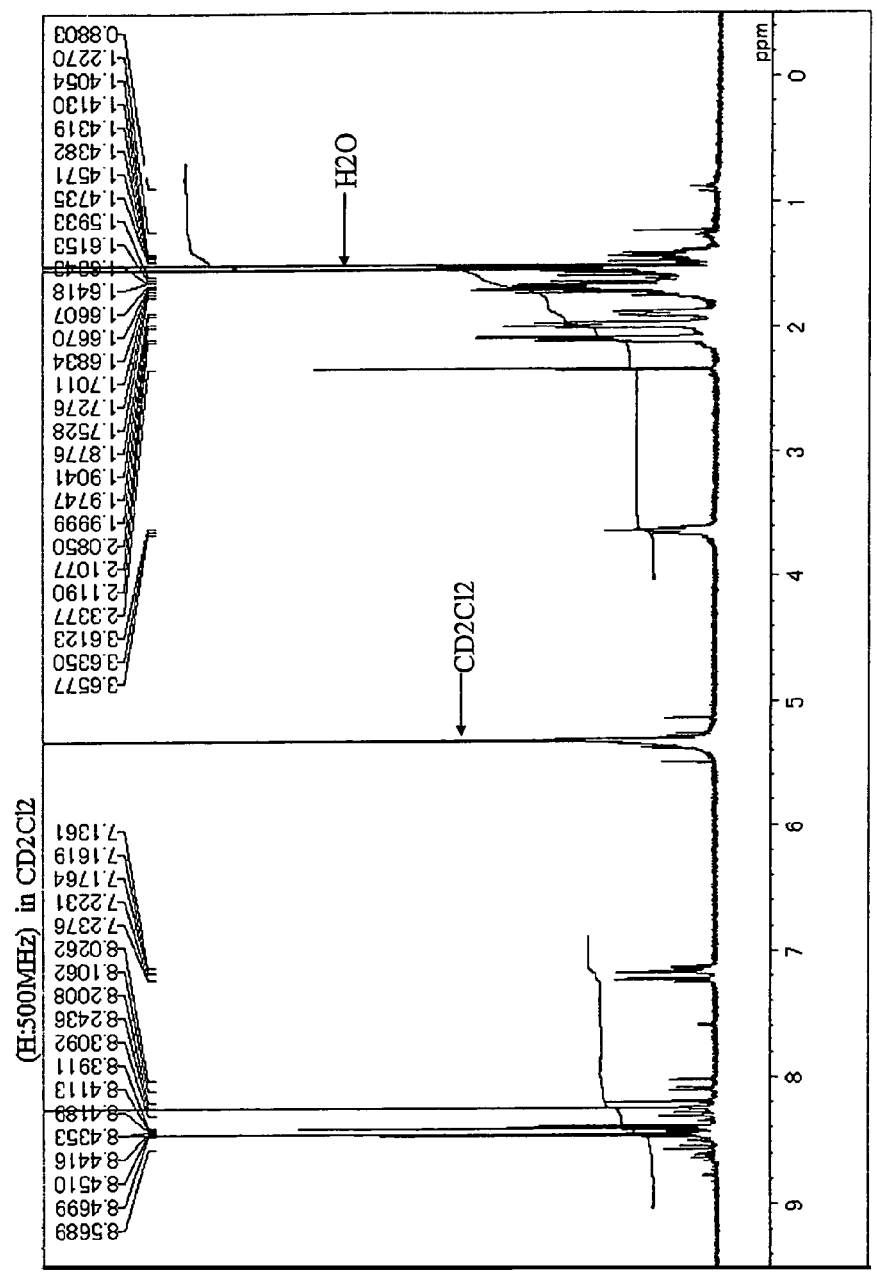
FIG. 8 is a chart showing a result of NMR measurement about 1,6-dicyclohexyl-3,8-dibromopyrene which is an intermediate material for Compound (D-83) as the aromatic amine derivative of the present invention.

Under an atmospheric argon gas flow, 1,6-dicyclohexylpyrene in an amount of 10.4 g (28.4 millimole), N-bromosuccinimide in an amount of 12.1 g (68.2 millimole) and dried dimethylformamide (DMF) in an amount of 300 milliliter were placed into an eggplant flask equipped with a cooling pipe and having a capacity of 1 liter, and the resultant solution was stirred with heating at a temperature of 50° C. for 7 hours. After the completion of the reaction, adding 300 milliliter of water, precipitated crystal was separated by filtration and washed with the use of 50 milliliter of water and 100 milliliter of methanol, and as a result, 6.2 g of pale yellow powder was obtained (the yield: 42%). The pale yellow powder was identified as 1,6-dicyclohexyl-3,8-dibromopyrene from the result of $^1$H-NMR spectrum (refer to FIG. 8) and FD-MS measurement.

(3) Synthesis of Compound (D-83)

Figure 9:
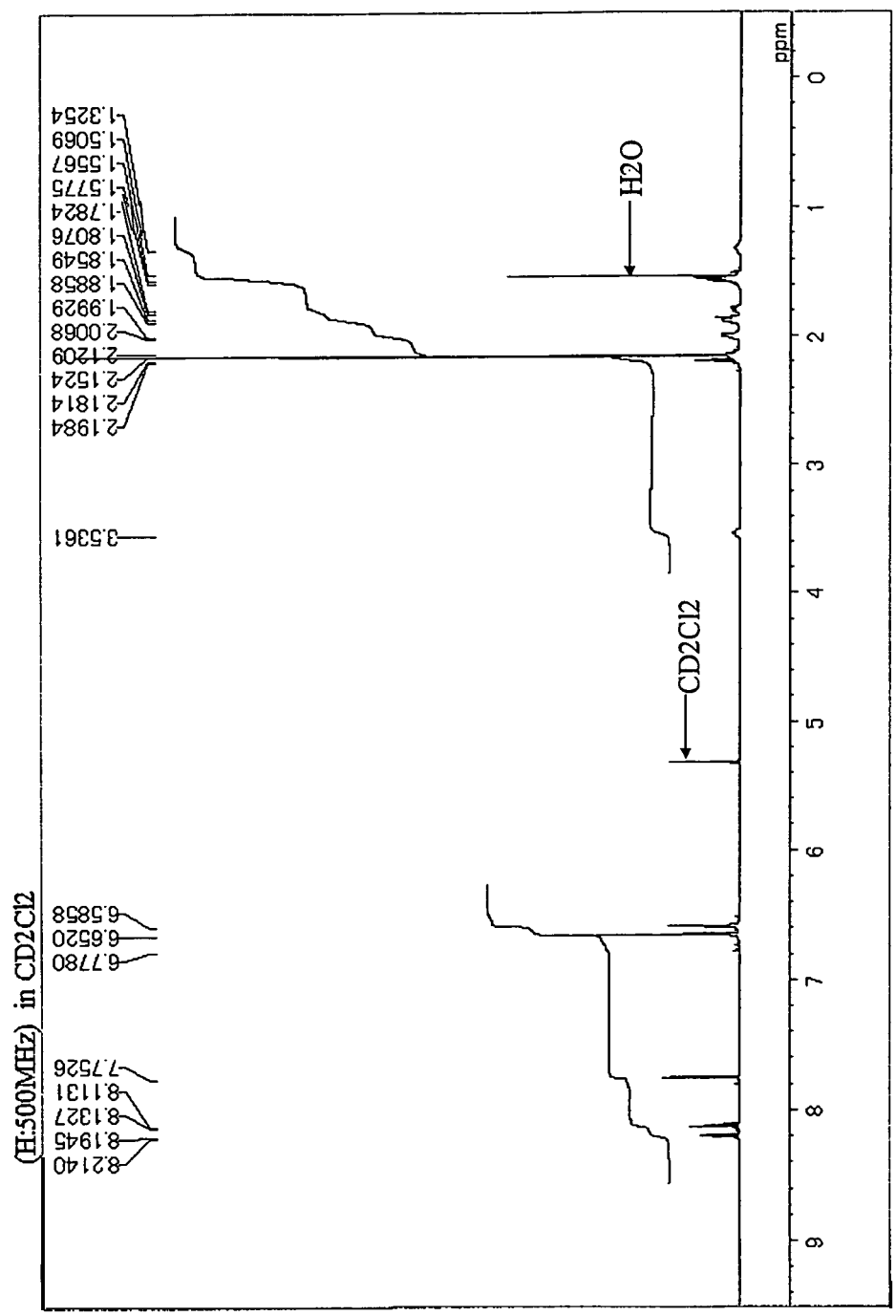
FIG. 9 is a chart showing a result of NMR measurement about Compound (D-83) as the aromatic amine derivative of the present invention.

Under an atmospheric argon gas flow, 1,6-dicyclohexyl-3,8-dibromopyrene in an amount of 3.0 g (5.7 millimole), bis(3,5-dimethylphenyl)amine in an amount of 3.1 g (13.7 millimole), palladium acetate in an amount of 0.02 g (1.5% by mole), tri-t-butylphosphine in an amount of 0.04 g (3% by mole), sodium-t-butoxide in an amount of 1.3 g (13.5 millimole) and dried toluene in an amount of 75 milliliter were placed into a three-neck flask equipped with a cooling pipe and having a capacity of 300 milliliter, and the resultant solution was stirred with heating at a temperature of 110° C. for 8 hours. After the completion of the reaction, the resultant solution was passed through a silicagel short column, and after concentrating under a reduced pressure, a precipitated crystal was separated by filtration. The crystal washed with the use of 50 milliliter of toluene and 100 milliliter of methanol, and as a result, 4.5 g of pale yellow powder was obtained. The pale yellow powder was identified as Compound (D-83) from the result of $^1$H-NMR spectrum (refer to FIG. 9) and FD-MS measurement (the yield: 97%).
[Peak absorption wavelength: 434 nanometers, Greatest fluorescent wavelength: 465 nanometers (toluene solution)]

Synthesis Example 8

Synthesis of Compound (D-101)

Figure 10:
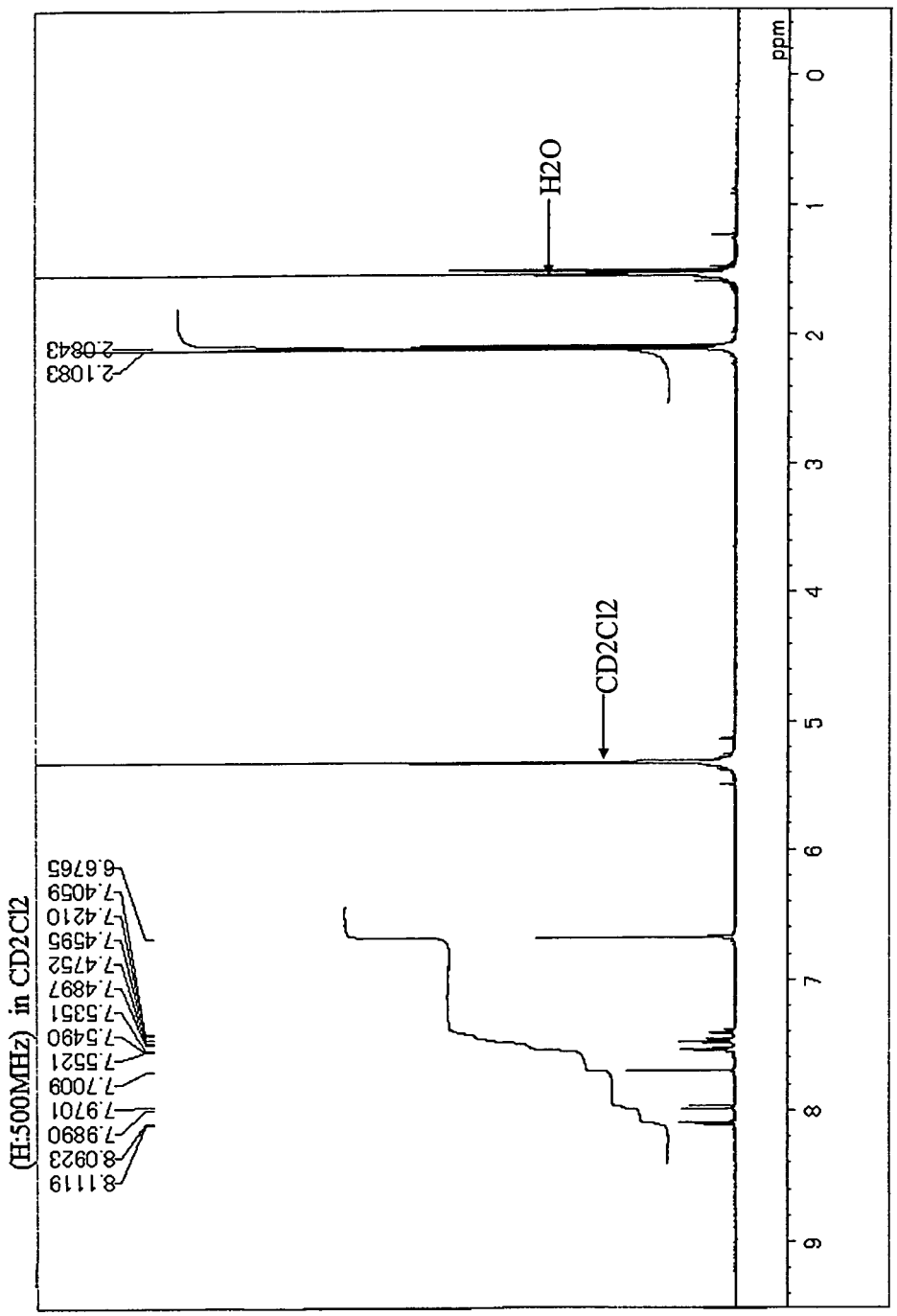
FIG. 10 is a chart showing a result of NMR measurement about Compound (D-101) as the aromatic amine derivative of the present invention.

Under an atmospheric argon gas flow, 1,6-diphenyl-3,8-dibromopyrene in an amount of 3.0 g (5.8 millimole), bis(3,4,5-trimethylphenyl)amine in an amount of 3.6 g (14.2 millimole), palladium acetate in an amount of 0.02 g (1.5% by mole), tri-t-butylphosphine in an amount of 0.04 g (3% by mole), sodium-t-butoxide in an amount of 1.4 g (14.5 millimole) and dried toluene in an amount of 50 milliliter were placed into a three-neck flask equipped with a cooling pipe and having a capacity of 300 milliliter, and the resultant solution was stirred with heating at a temperature of 110° C. for 8 hours. After the completion of the reaction, precipitated crystal was separated by filtration and washed with the use of 50 milliliter of toluene and 100 milliliter of methanol, and as a result, 5.0 g of pale yellow powder was obtained. The pale yellow powder was identified as Compound (D-101) from the result of $^1$H-NMR spectrum (refer to FIG. 10) and FD-MS measurement (the yield: 99%).
[Peak absorption wavelength: 460 nanometers, Greatest fluorescent wavelength: 498 nanometers (toluene solution)]

Synthesis Example 9

Synthesis of Compound (D-109)

(1) Synthesis of Intermediate Material
(1,6-di(2-biphenyl)pyrene)

Under an atmospheric argon gas flow, 1,6-dibromopyrene in an amount of 9.7 g (27.0 millimole), 2-biphenylboronic acid in an amount of 12.8 g (64.8 millimole), tetrakis(triphenylphosphine)palladium(0) in an amount of 1.25 g (4% by mole), sodium carbonate aqueous solution in an amount of 61 milliliter (122 millimole, 2M), and dimethoxyethane (DME) in an amount of 120 milliliter were placed into a three-neck flask equipped with a cooling pipe and having a capacity of 200 milliliter, and the resultant solution was stirred with heating at a temperature of 90° C. for 8 hours. After the completion of the reaction, adding 50 milliliter of water, precipitated crystal was separated by filtration and washed with the use of 50 milliliter of water and 100 milliliter of ethanol, and as a result, 13.3 g of 1,6-di(2-biphenyl)pyrene (white powder) was obtained (the yield: 97%).

(2) Synthesis of Intermediate Material
(1,6-di(2-biphenyl)-3,8-dibromopyrene)

Figure 11:
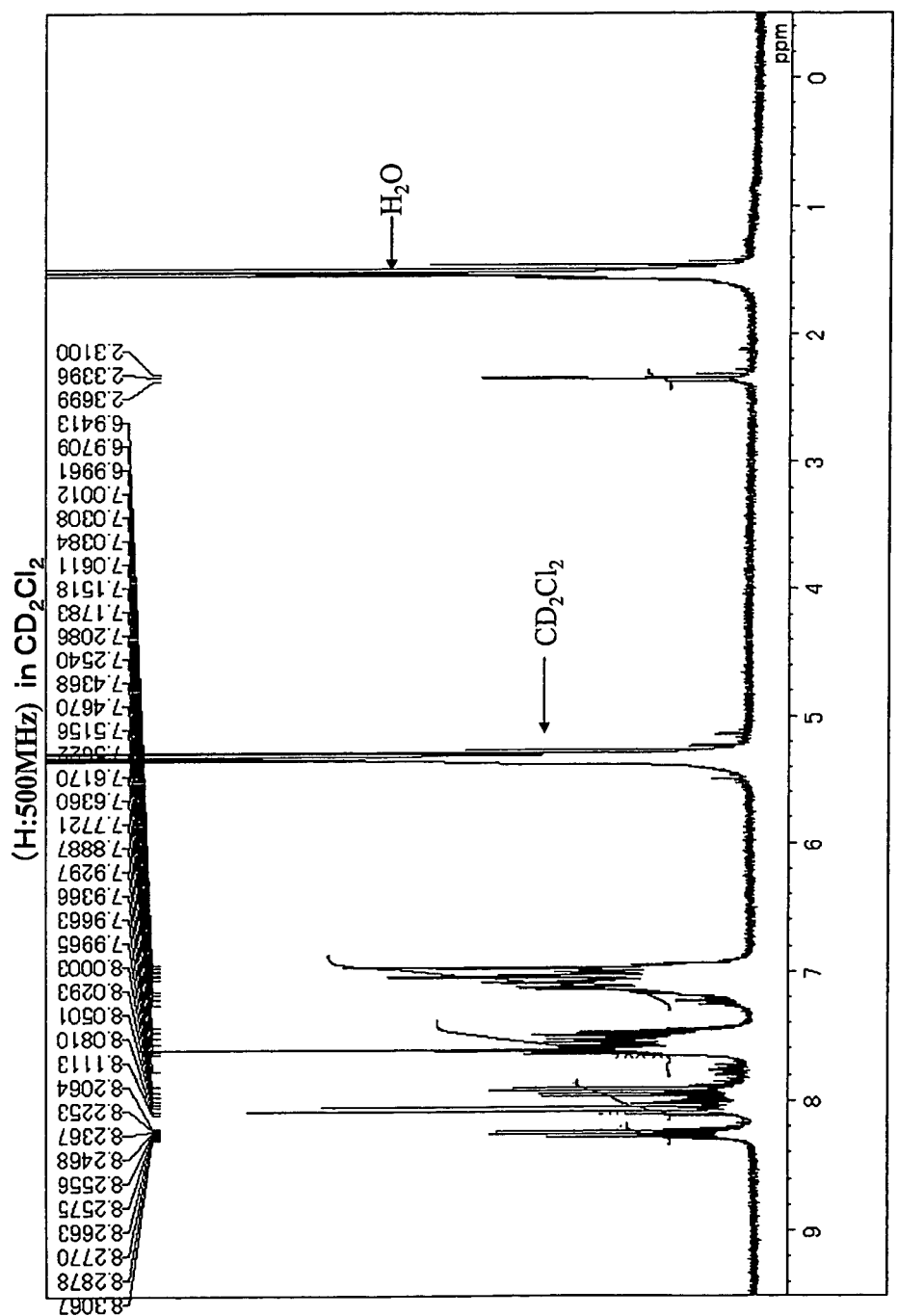
FIG. 11 is a chart showing a result of NMR measurement about 1,6-di(2-biphenyl)-3,8-dibromopyrene which is an intermediate material for Compound (D-109) as the aromatic amine derivative of the present invention.

Under an atmospheric argon gas flow, 1,6-di(2-biphenyl)pyrene in an amount of 13.2 g (26.1 millimole), N-bromosuccinimide in an amount of 9.8 g (55 millimole) and dried dimethylformamide (DMF) in an amount of 550 milliliter were placed into an eggplant flask equipped with a cooling pipe and having a capacity of 1 liter, and the resultant solution was stirred with heating at a temperature of 50° C. for 8 hours. After the completion of the reaction, adding 300 milliliter of water, precipitated crystal was separated by filtration and washed with the use of 50 milliliter of water and 100 milliliter of methanol, and as a result, 10.5 g of pale yellow powder was obtained (the yield: 61%). The pale yellow powder was identified as 1,6-di(2-biphenyl)-3,8-dibromopyrene from the result of $^1$H-NMR spectrum (refer to FIG. 11) and FD-MS measurement.

(3) Synthesis of Compound (D-109)

Figure 12:
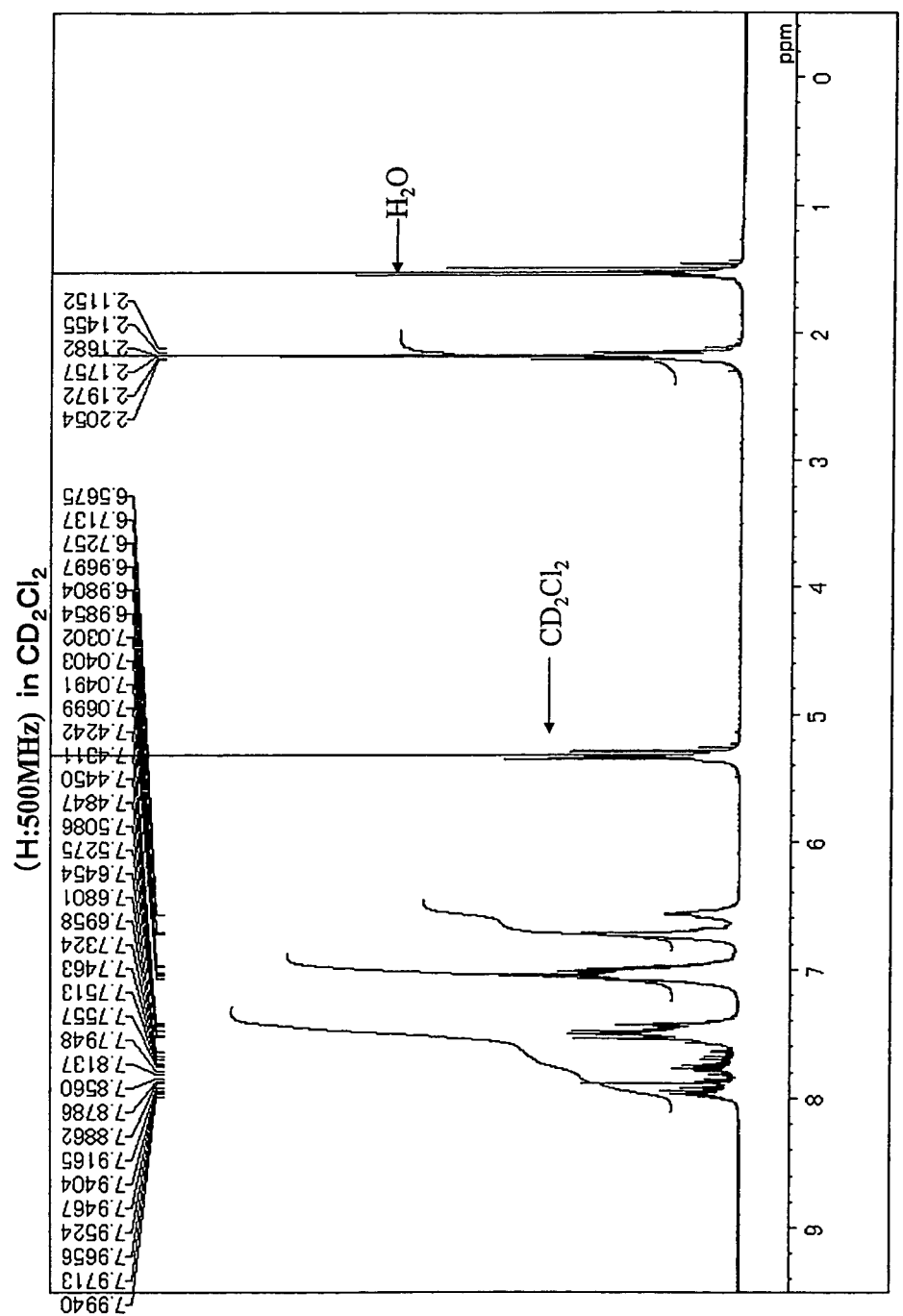
FIG. 12 is a chart showing a result of NMR measurement about Compound (D-109) as the aromatic amine derivative of the present invention.

Under an atmospheric argon gas flow, 1,6-di(2-biphenyl)-3,8-dibromopyrene in an amount of 3.5 g (5.2 millimole), m,m'-ditolylamine in an amount of 2.5 g (12.6 millimole), palladium acetate in an amount of 20 milligram (1.5% by mole), tri-t-butylphosphine in an amount of 36 milligram (3% by mol), sodium-t-butoxide in an amount of 1.3 g (13.5 millimole) and dried toluene in an amount of 75 milliliter were placed into a three-neck flask equipped with a cooling pipe and having a capacity of 300 milliliter, and the resultant solution was stirred with heating at a temperature of 110° C. for 8 hours. After the completion of the reaction, the resultant solution was passed through a silicagel short column, processed re-precipitation with a use of a toluene-methanol and as a result, 3.9 g of yellow crystal was obtained. The yellow crystal was identified as Compound (D-109) from the result of $^1$H-NMR spectrum (refer to FIG. 12) and FD-MS measurement (the yield: 82%).
[Peak absorption wavelength: 442 nanometers, Greatest fluorescent wavelength: 474 nanometers (toluene solution)]

Synthesis Example 10

Synthesis of Compound (D-110)

Figure 13:
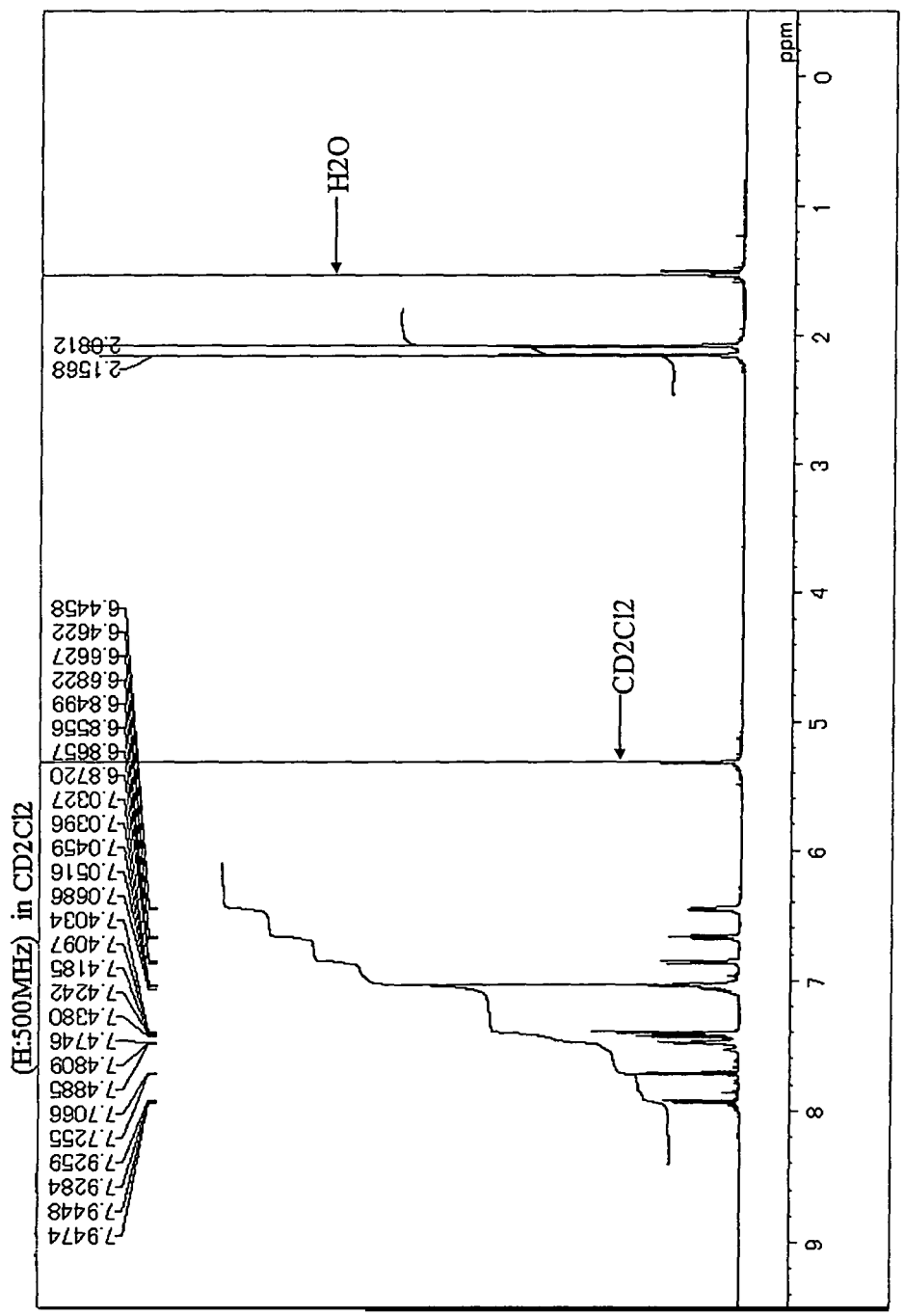
FIG. 13 is a chart showing a result of NMR measurement about Compound (D-110) as the aromatic amine derivative of the present invention.

Under an atmospheric argon gas flow, 1,6-di(2-biphenyl)-3,8-dibromopyrene in an amount of 3.0 g (4.5 millimole), bis(3,4-dimethylphenyl)amine in an amount of 2.4 g (10.8 millimole), palladium acetate in an amount of 20 milligram (1.5% by mole), tri-t-butylphosphine in an amount of 27 milligram (3% by mole), sodium-t-butoxide in an amount of 1.3 g (13.5 millimole) and dried toluene in an amount of 50 milliliter were placed into a three-neck flask equipped with a cooling pipe and having a capacity of 300 milliliter, and the resultant solution was stirred with heating at a temperature of 110° C. for 8 hours. After the completion of the reaction, precipitated crystal was separated by filtration and washed with the use of 50 milliliter of methylene chloride and 100 milliliter of methanol, and as a result, 3.9 g of yellow crystal was obtained. The yellow crystal was identified as Compound (D-110) from the result of $^1$H-NMR spectrum (refer to FIG. 13) and FD-MS measurement (the yield: 94%).
[Peak absorption wavelength: 455 nanometers, Greatest fluorescent wavelength: 488 nanometers (toluene solution)]

Synthesis Example 11

Synthesis of Compound (D-115)

Figure 14:
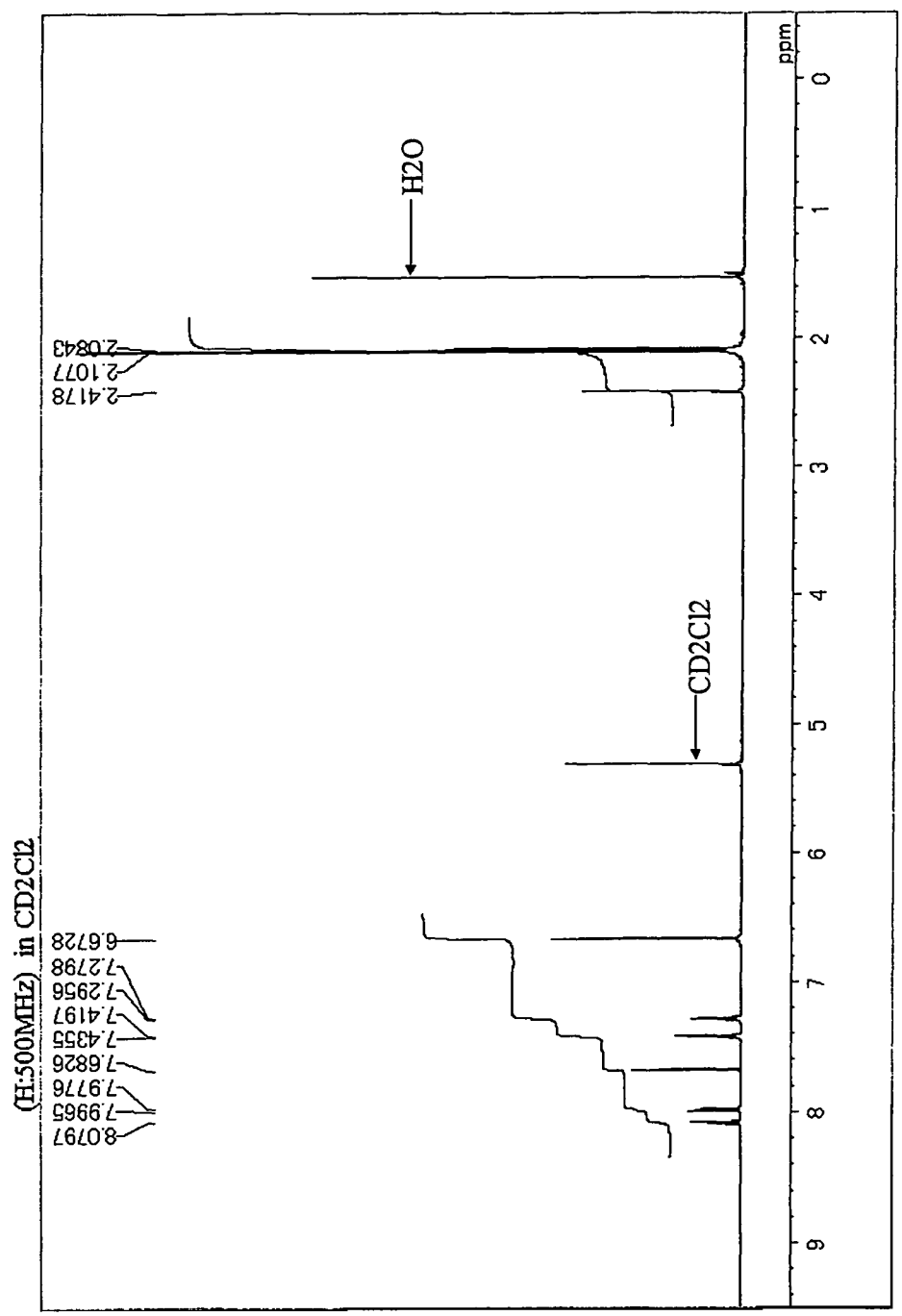
FIG. 14 is a chart showing a result of NMR measurement about Compound (D-115) as the aromatic amine derivative of the present invention.

Under an atmospheric argon gas flow, 1,6-di(4-methylphenyl)-3,8-dibromopyrene in an amount of 3.0 g (5.5 millimole), bis (3,4,5-trimethylphenyl)amine in an amount of 3.4 g (13.4 millimole), palladium acetate in an amount of 0.02 g (1.5% by mole), tri-t-butylphosphine in an amount of 0.03 g (3% by mole), sodium-t-butoxide in an amount of 1.3 g (13.5 millimole) and dried toluene in an amount of 75 milliliter were placed into a three-neck flask equipped with a cooling pipe and having a capacity of 300 milliliter, and the resultant solution was stirred with heating at a temperature of 110° C. for 8 hours. After the completion of the reaction, precipitated crystal was separated by filtration and washed with the use of 50 milliliter of methylene chloride and 100 milliliter of methanol, and as a result, 4.4 g of yellow crystal was obtained. The yellow crystal was identified as Compound (D-115) from the result of $^1$H-NMR spectrum (refer to FIG. 14) and FD-MS measurement (the yield: 89%).
[Peak absorption wavelength: 459 nanometers, Greatest fluorescent wavelength: 494 nanometers (toluene solution)]

Synthesis Example 12

Synthesis of Compound (D-122)

(1) Synthesis of Intermediate Material (1,6-di(4-cyanophenyl)pyrene)

Under an atmospheric argon gas flow, 1,6-dibromopyrene in an amount of 7.1 g (19.8 millimole), 4-cyanophenylboronic acid in an amount of 7.0 g (47.5 millimole), tetrakis(triphenylphosphine)palladium(0) in an amount of 0.46 g (2% by mole), sodium carbonate aqueous solution in an amount of 30 milliliter (59.4 millimole, 2M), dimethoxyethane (DME) in an amount of 60 milliliter and dried THF in an amount of 70 milliliter were placed into a three-neck flask equipped with a cooling pipe and having a capacity of 200 milliliter, and the resultant solution was stirred with heating at a temperature of 90° C. for 8 hours. After the completion of the reaction, adding 50 milliliter of water, precipitated crystal was separated by filtration and washed with the use of 50 milliliter of water and 100 milliliter of ethanol, and as a result, 7.8 g of pale yellow powder was obtained (the yield: 98%).

(2) Synthesis of Intermediate Material (1,6-di(4-cyanophenyl)-3,8-dibromopyrene)

Figure 15:
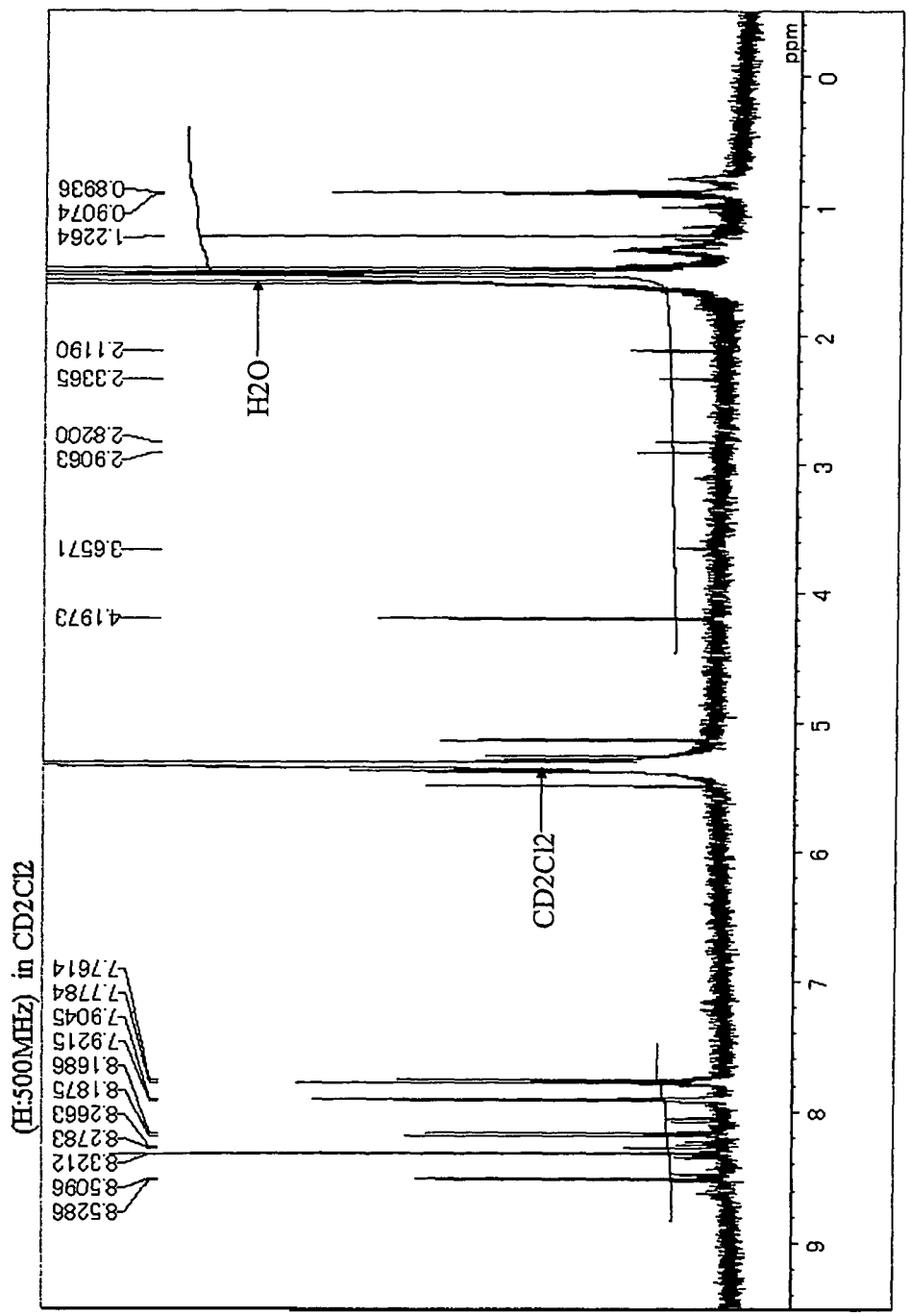
FIG. 15 is a chart showing a result of NMR measurement about 1,6-di(4-cyanophenyl)-3,8-dibromopyrene which is an intermediate material for Compound (D-122) as the aromatic amine derivative of the present invention.

Under an atmospheric argon gas flow, 1,6-di(4-cyanophenyl)pyrene in an amount of 12.8 g (31.7 millimole), N-bromosuccinimide in an amount of 13.5 g (76 millimole) and dried dimethylformamide (DMF) in an amount of 450 milliliter were placed into an eggplant flask equipped with a cooling pipe and having a capacity of 1 liter, and the resultant solution was stirred with heating at a temperature of 50° C. for 8 hours. After the completion of the reaction, adding 300 milliliter of water, precipitated crystal was separated by filtration and washed with the use of 50 milliliter of water and 100 milliliter of methanol, and as a result, 16.3 g of pale yellow powder was obtained (the yield: 41%). The pale yellow powder was identified as 1,6-di(4-cyanophenyl)-3,8-dibromopyrene from the result of $^1$H-NMR spectrum (refer to FIG. 15) and FD-MS measurement.

(3) Synthesis of Compound (D-122)

Figure 16:
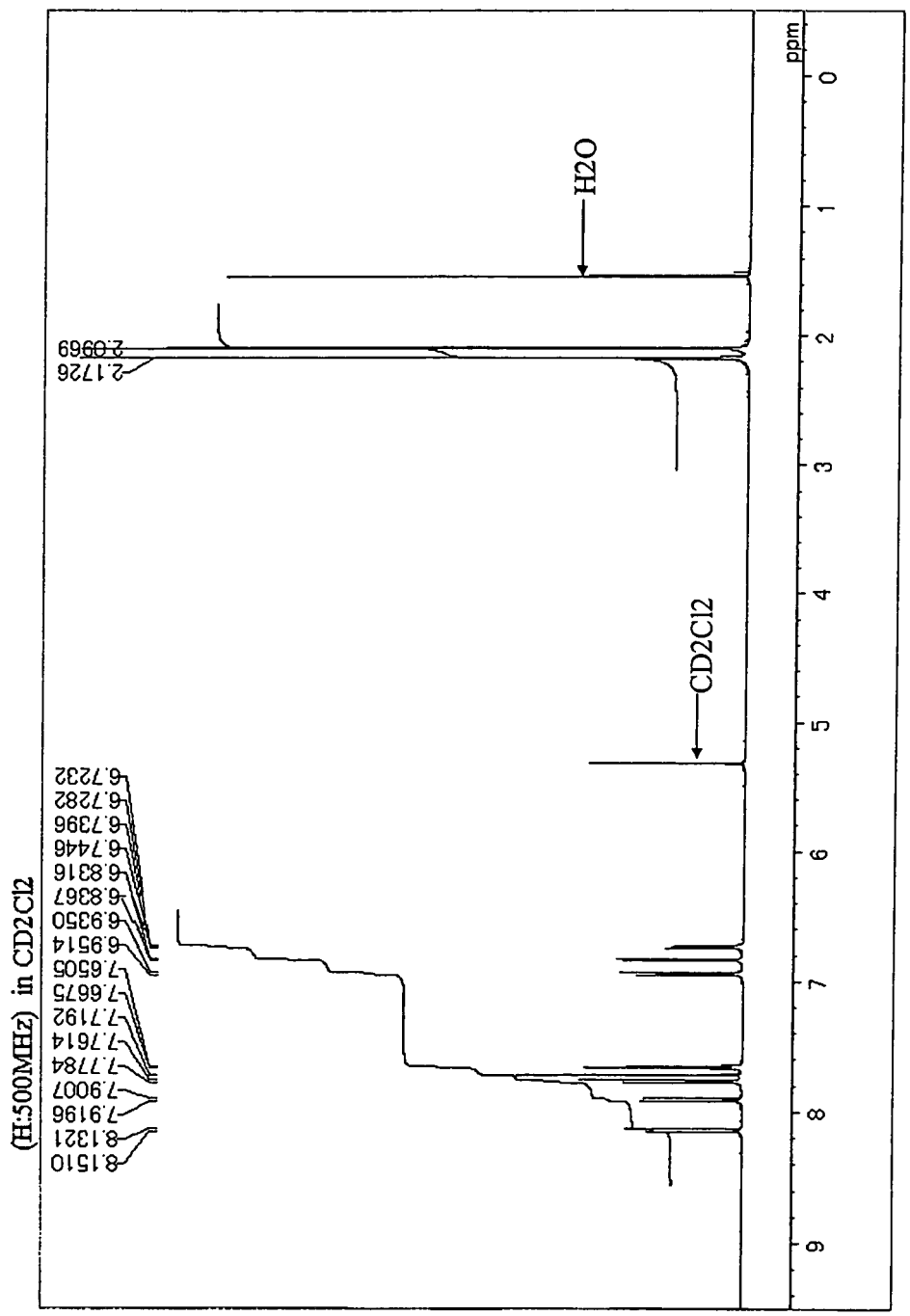
FIG. 16 is a chart showing a result of NMR measurement about Compound (D-122) as the aromatic amine derivative of the present invention.

Under an atmospheric argon gas flow, 1,6-di(4-cyanophenyl)-3,8-dibromopyrene in an amount of 3.0 g (5.3 millimole), bis(3,4-dimethylphenyl)amine in an amount of 3.0 g (13.3 millimole), palladium acetate in an amount of 0.02 g (1.5% by mole), tri-t-butylphosphine in an amount of 0.03 g (3% by mole), sodium-t-butoxide in an amount of 1.2 g (12.8 millimole) and dried toluene in an amount of 50 milliliter were placed into a three-neck flask equipped with a cooling pipe and having a capacity of 300 milliliter, and the resultant solution was stirred with heating at a temperature of 110° C. for 8 hours. After the completion of the reaction, precipitated crystal was separated by filtration and washed with the use of 50 milliliter of methylene chloride and 100 milliliter of methanol, and as a result, 3.4 g of yellow crystal was obtained. The yellow crystal was identified as Compound (D-122) from the result of $^1$H-NMR spectrum (refer to FIG. 16) and FD-MS measurement (the yield: 74%).
[Peak absorption wavelength: 475 nanometers, Greatest fluorescent wavelength: 526 nanometers (toluene solution)]

Synthesis Example 13

Synthesis of Compound (D-148)

(1) Synthesis of Intermediate Material (1,6-di(2-naphthyl)pyrene)

Under an atmospheric argon gas flow, 1,6-dibromopyrene in an amount of 10.3 g (28.6 millimole), 2-naphthylboronic acid in an amount of 11.8 g (68.7 millimole), tetrakis(triphenylphosphine)palladium(0) in an amount of 0.66 g (2% by mole), sodium carbonate aqueous solution in an amount of 43 milliliter (59.4 millimole, 2M), dimethoxyethane (DME) in an amount of 100 milliliter and dried THF in an amount of 70 milliliter were placed into a three-neck flask equipped with a cooling pipe and having a capacity of 200 milliliter, and the resultant solution was stirred with heating at a temperature of 90° C. for 8 hours. After the completion of the reaction, adding 50 milliliter of water, precipitated crystal was separated by filtration and washed with the use of 50 milliliter of water and 100 milliliter of ethanol, and as a result, 13.2 g of 1,6-di(2-naphthyl)pyrene (pale yellow powder) was obtained (the yield: 99%).

(2) Synthesis of Intermediate Material (1,6-di(2-naphthyl)-3,8-dibromopyrene)

Figure 17:
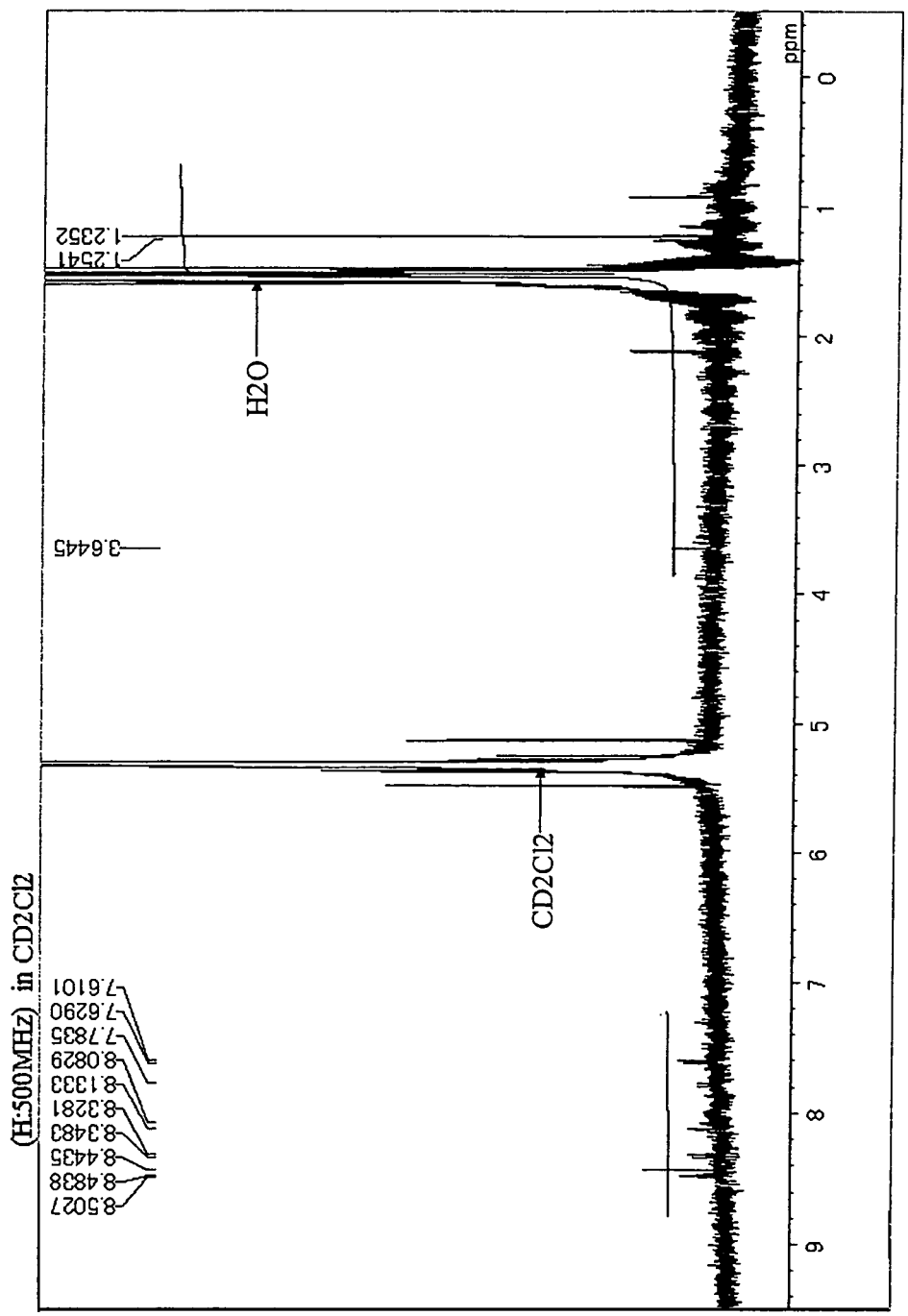
FIG. 17 is a chart showing a result of NMR measurement about 1,6-di(2-naphthyl)-3,8-dibromopyrene which is an intermediate material for Compound (D-148) as the aromatic amine derivative of the present invention.

Under an atmospheric argon gas flow, 1,6-di(2-naphthyl) pyrene in an amount of 13 g (28.6 millimole), N-bromosuccinimide in an amount of 11.8 g (68.7 millimole) and dried dimethylformamide (DMF) in an amount of 450 milliliter were placed into an eggplant flask equipped with a cooling pipe and having a capacity of 1 liter, and the resultant solution was stirred with heating at a temperature of 50° C. for 8 hours. After the completion of the reaction, adding 300 milliliter of water, precipitated crystal was separated by filtration and washed with the use of 50 milliliter of water and 100 milliliter of methanol, and as a result, 7.0 g of pale yellow powder was obtained (the yield: 40%). The pale yellow powder was identified as 1,6-di(2-naphthyl)-3,8-dibromopyrene from the result of $^1$H-NMR spectrum (refer to FIG. 17) and FD-MS measurement.

(3) Synthesis of Compound (D-148)

Figure 18:
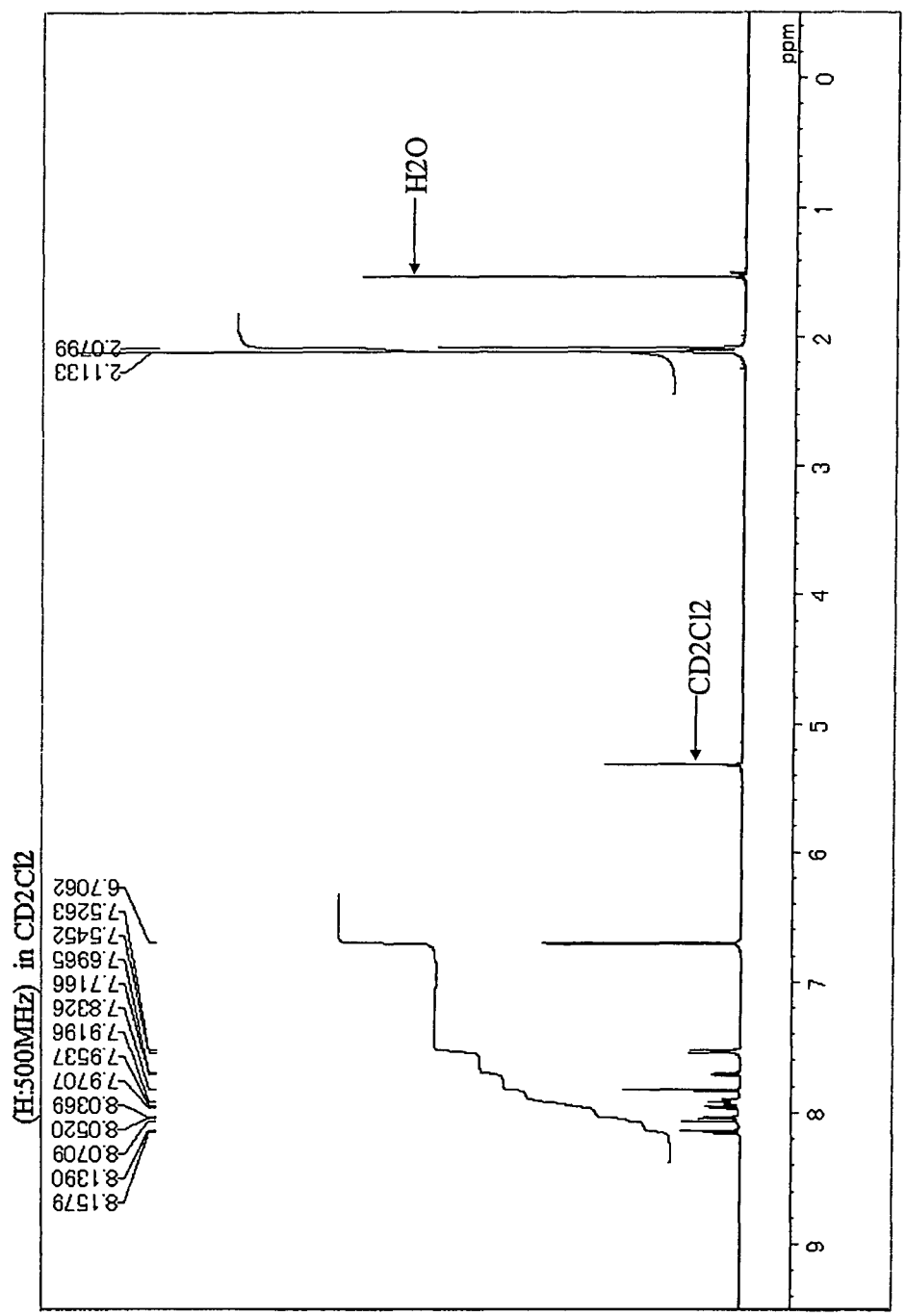
FIG. 18 is a chart showing a result of NMR measurement about Compound (D-148) as the aromatic amine derivative of the present invention.

Under an atmospheric argon gas flow, 1,6-di(2-naphthyl)-3,8-dibromopyrene in an amount of 2.0 g (3.3 millimole), bis(3,4,5-trimethylphenyl)amine in an amount of 2.0 g (7.9 millimole), palladium acetate in an amount of 0.01 g (1.5% by mole), tri-t-butylphosphine in an amount of 0.02 g (3% by mole), sodium-t-butoxide in an amount of 0.75 g (7.8 millimole) and dried toluene in an amount of 50 milliliter were placed into a three-neck flask equipped with a cooling pipe and having a capacity of 300 milliliter, and the resultant solution was stirred with heating at a temperature of 110° C. for 8 hours. After the completion of the reaction, precipitated crystal was separated by filtration and washed with the use of 50 milliliter of methylene chloride and 100 milliliter of methanol, and as a result, 2.9 g of yellow crystal was obtained. The yellow crystal was identified as Compound (D-148) from the result of $^1$H-NMR spectrum (refer to FIG. 18) and FD-MS measurement (the yield: 96%).

[Peak absorption wave length: 466 nanometers, Greatest fluorescent wavelength: 506 nanometers (toluene solution)]

Example 1

(1) Fabrication of an Organic EL Device

A 130 nanometers-thick transparent electrode made of indium tin oxide was formed on a glass substrate having a size of 25 mm×75 mm×1.1 mm. The glass substrate was cleaned by application of ultrasonic wave in isopropyl alcohol and then by exposure to ultraviolet ray and ozone.

Subsequently, the glass substrate having the transparent electrode which had been cleaned was attached to a substrate holder of a vacuum vapor deposition apparatus. Then, after reducing a degree of vacuum in a vacuum chamber of the vacuum vapor deposition apparatus down to $1\times10^{-3}$ Pa, a hole injecting layer, a hole transporting layer, a light emitting layer, an electron transporting layer, an electron injecting layer and cathode layer were successively laminated on the anode layer in accordance with following vapor deposition conditions. As a result, an organic EL device was fabricated.
Hole Injecting Layer:
N',N''-bis[4-(diphenylamino)phenyl]-N',N''-diphenylbiphenyl-4,4'-diamine as material; vapor deposition condition of 2 nanometers/second; film thickness of 60 nanometers;
Hole Transporting Layer:
N,N,N',N'-tetrakis(4-biphenyl)-4,4'-benzidine as material; vapor deposition condition of 2 nanometers/second; film thickness of 20 nanometers
Light Emitting Layer:
Employing 1,4-bis[10-(2-biphenyl)anthracene-9-yl]benzene (H-1) as a light emitting material, and employing the above Compound (D-3) as a doping material, a simultaneous vapor deposition of compound (H-1) and the above Compound (D-3) with a weight ratio of 40:2 was carried out at vapor deposition condition of 2 nanometers/second about (H-1), and vapor deposition condition of 0.2 nanometers/second about Compound (D-3); film thickness of 40 nanometers
Electron Transporting Layer:
Tris(8-hydroxyquinolino)aluminum as material; vapor deposition condition of 2 nanometers/second; film thickness of 20 nanometers
Electron Injecting Layer:
Lithium fluoride as material; vapor deposition condition of 0.1 nanometers/second; film thickness of 1 nanometer
Cathode Layer:
Aluminum as material; vapor deposition condition of 2 nanometers/second;
film thickness of 200 nanometers
(2) Evaluation of the Organic EL Device As a result of subjecting the organic EL device obtained in the above term (1) to a test by feeding electric current, it was confirmed that a blue light (main wavelength of light emission: 468 nanometers) with a luminance of 821 cd/m$^2$ was emitted at a voltage of 6.7 V and a current density of 10 mA/cm$^2$. Further, driving with a constant electric current starting from an initial luminance of 2,000 cd/m$^2$, a half lifetime of luminance when the initial luminance reduced to one half was 2,800 hours or longer.

Example 2 to 8

Examples 2 to 8 were conducted in a similar manner as Example 1 except that 10-(4-(naphthalene-1-yl)phenyl)-9-(naphthalene-3-yl)anthracene (H-2) was used instead of Compound (H-1) as the light emitting material and following materials are used instead of Compound (D-3) as the doping material resultantly fabricating organic EL devices.

Example 2

Compound (H-2) and the foregoing Compound (D-38) with a weight ratio of 40:2

Example 3

Compound (H-2) and the foregoing Compound (D-39) with a weight ratio of 40:2

Example 4

Compound (H-2) and the foregoing Compound (D-40) with a weight ratio of 40:2

Example 5

Compound (H-2) and the foregoing Compound (D-77) with a weight ratio of 40:2

Example 6

Compound (H-2) and the foregoing Compound (D-78) with a weight ratio of 40:2

Example 7

Compound (H-2) and the foregoing Compound (D-82) with a weight ratio of 40:2

Example 8

Compound (H-2) and the foregoing Compound (D-83) with a weight ratio of 40:2

The devices fabricated above were tested by feeding electric current in the same manner as Example 1 (2), and the results are shown in Table 1.

As shown in Table 1, blue light emission was observed about all organic EL devices of Examples 1 to 8 with luminance of 700 cd/m$^2$ or greater, up to 1,000 cd/m$^2$ or greater as the maximum value; the half lifetime under the luminance degradation accelerated condition was 2,000 hours or longer, up to 5,000 hours or longer as the maximum value.

Comparative Examples 1 to 4

Comparative Examples 1 to 4 were carried out in similar manners as Example 1 except that following materials were used instead of Compound (H-1) as the light emitting material employed in the light emitting layer and instead of Compound (D-3) as the doping material and resultantly, organic EL devices were fabricated.

Comparative Example 1

Only Compound (H-1) was used

Comparative Example 2

Compound (H-1) and 1,6-bis(diphenylamino)pyrene (Compound (A)) with a weight ratio of 40:2

Comparative Example 3

Compound (H-1) and N,N'-bis-m-tolyl-N,N'-diphenyl-1,6-diamino pyrene (Compound (B)) with a weight ratio of 40:2

Comparative Example 4

Compound (H-1) and 2,5,8,11-tetrakis(t-butyl)perylene (Compound (C)) with a weight ratio of 40:2

The devices fabricated above were tested by feeding electric current in the same manner as Example 1 (2), and the results are shown in Table 2.

TABLE 1

| | Example | | | | | | | |
|---|---|---|---|---|---|---|---|---|
| | 1 | 2 | 3 | 4 | 5 | 6 | 7 | 8 |
| Driving Voltage (V) | 6.7 | 7.7 | 7.3 | 7.8 | 7.5 | 7.4 | 7.5 | 7.5 |
| Luminance (cd/m$^2$) | 821 | 715 | 827 | 884 | 773 | 887 | 960 | 1018 |
| Color of light emission | Blue | Blue | Blue | Blue | Blue | Blue | Blue | Blue |
| Main wavelength of light emission (nm) | 468 | 468 | 469 | 472 | 470 | 472 | 469 | 473 |
| Half Lifetime (hours) | 2800 hours or longer | 2000 hours or longer | 3000 hours or longer | 3000 hours or longer | 2500 hours or longer | 4000 hours or longer | 3500 hours or longer | 5000 hours or longer |

TABLE 2

|  | Comparative Example | | | |
|---|---|---|---|---|
|  | 1 | 2 | 3 | 4 |
| Driving Voltage (V) | 5.9 | 6.4 | 6.3 | 5.5 |
| Luminance (cd/m$^2$) | 167 | 615 | 657 | 326 |
| Color of light emission | Blue | Blue | Blue | Blue |
| Main wavelength of light emission (nm) | 438 | 464 | 465 | 462 |
| Half Lifetime (hours) | 50 | 480 | 1000 | 100 |

Examples 9 to 15

Comparative Examples 9 to 15 were carried out in similar manners as Example 1 except that following materials were used instead of Compound (H-1) as the light emitting material employed in the light emitting layer and instead of Compound (D-3) as the doping material and resultantly, organic EL devices were fabricated.

Example 9

Compound (H-1) and the foregoing Compound (D-97) with a weight ratio of 40:2

Example 10

Compound (H-1) and the foregoing Compound (D-101) with a weight ratio of 40:3

Example 11

Compound (H-2) and the foregoing Compound (D-101) with a weight ratio of 40:3

Example 12

Compound (H-1) and the foregoing Compound (D-148) with a weight ratio of 40:3

Example 13

Compound (H-2) and the foregoing Compound (D-148) with a weight ratio of 40:3

Example 14

Compound (H-2) and the foregoing Compound (D-148) with a weight ratio of 40:4

Example 15

Compound (H-1) and the foregoing Compound (D-93) with a weight ratio of 40:2

The devices fabricated above were tested by feeding electric current in the same manner as Example 1 (2), and the results are shown in Table 3.

TABLE 3

|  | Example | | | | | | |
|---|---|---|---|---|---|---|---|
|  | 9 | 10 | 11 | 12 | 13 | 14 | 15 |
| Driving Voltage (V) | 6.8 | 9 | 7.7 | 6.6 | 8.9 | 8.3 | 6.7 |
| Luminance (cd/m$^2$) | 1595 | 1702 | 1855 | 1923 | 1777 | 1866 | 1208 |
| Color of light emission | Green | Green | Green | Green | Green | Green | Green |
| Main wavelength of light emission (nm) | 500 | 505 | 507 | 516 | 515 | 517 | 486 |
| Half Lifetime (hours) | 5000 hours or longer | 20000 hours or longer | 20000 hours or longer | 20000 hours or longer | 20000 hours or longer | 20000 hours or longer | 5000 hours or longer |

As shown in Table 3, green light emission was observed about all organic EL devices of Examples 9 to 15 with luminance of 1200 cd/m$^2$ or greater, up to 1,900 cd/m$^2$ or greater as the maximum value; the half lifetime under the luminance degradation accelerated condition was 5,000 hours or longer, up to 20,000 hours or longer as the maximum value. They are practical enough.

Comparative Examples 5 and 6

Comparative Examples 5 and 6 were carried out in similar manners as Example 1 except that following materials were used instead of Compound (H-1) as the light emitting material employed in the light emitting layer and instead of Compound (D-3) as the doping material and resultantly, organic EL devices were fabricated.

Comparative Example 5

Compound (H-1) and 9,10-bis(diphenylamino)anthracene (compound (D)) with a weight ratio of 40:3

Comparative Example 6

Tris(8-hydroxyquinolino) aluminum (H-3) and 10-(2-benzthiazoyl)-1,1,7,7-tetramethyl-2,3,6,7-tetrahydro-1H,5H,11H-benz[1]pyrano[6,7,8-ij]quinolysine-11-on (Compound (E)) with a weight ratio of 40:0.5

The devices fabricated above were tested by feeding electric current in the same manner as Example 1 (2), and the results are shown in Table 4.

TABLE 4

|  | Comparative Example | |
|---|---|---|
|  | 5 | 6 |
| Driving Voltage (V) | 6.8 | 6.5 |
| Luminance (cd/m$^2$) | 805 | 1000 |
| Color of light emission | Green | Green |

TABLE 4-continued

| | Comparative Example | |
|---|---|---|
| | 5 | 6 |
| Main wavelength of light emission (nm) | 515 | 525 |
| Half Lifetime (hours) | 2700 | 1800 |

The results of above Examples and Comparative Examples verify that introducing a substituent into pyrene skeleton of diaminopyrene remarkably improves half lifetime of the organic EL devices in particular. This shows a substitution on pyrene skeleton and an amino substituent were able to suppress concentration quenching that may be caused by an association between dopants.

Industrial Applicability

The organic EL device employing the aromatic amine derivative represented by the general formula (A), general formula (A') or general formula (A") of the present invention provides practically enough luminance at low applied voltage, an enhanced current efficiency of light emission and a long lifetime without degradation even after a long time usage. Therefore, they are extremely applicable as the organic EL devices having highly practical performance.

Further, in accordance with the process for producing an aromatic amine derivative of the present invention, an aromatic amine derivative having a three-dimensionally bulky substituent in central pyrene skeleton can be efficiently produced.

The invention claimed is:

1. An aromatic amine derivative represented by general formula (A):

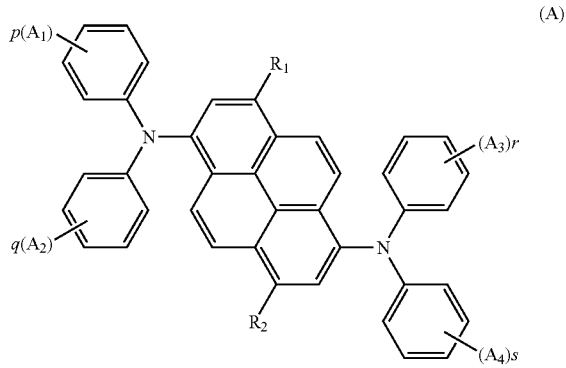

(A)

wherein $R_1$ and $R_2$ are each independently selected from the group consisting of a substituted or unsubstituted aryl group having 5 to 25 carbon atoms, and a substituted or unsubstituted cycloalkyl group having 3 to 25 carbon atoms;

$A_1$, $A_2$, $A_3$ and $A_4$ each independently represents a hydrogen atom, a substituted or unsubstituted alkyl group having 1 to 20 carbon atoms, a substituted or unsubstituted aryl group having 5 to 25 carbon atoms, or a substituted or unsubstituted cycloalkyl group having 3 to 25 carbon atoms, however, a case where any substituent of each group represented by $R_1$, $R_2$, $A_1$, $A_2$, $A_3$ and $A_4$ comprises a vinyl group is excluded;

p, q, r and s each independently represents an integer of 1 to 5; when p represents an integer of 2 or greater, each of plural $A_1$ may be the same with, or different from each other, and may bond each other to form a saturated or unsaturated ring; when q represents an integer of 2 or greater, each of plural $A_2$ may be the same with, or different from each other, and may bond each other to form a saturated or unsaturated ring; when r represents an integer of 2 or greater, each of plural $A_3$ may be the same with, or different from each other, and may bond each other to form a saturated or unsaturated ring; and when s represents an integer of 2 or greater, each of plural $A_4$ may be the same with, or different from each other, and may bond each other to form a saturated or unsaturated ring.

2. The aromatic amine derivative according to claim 1, wherein at least one of p, q, r and s represents an integer of 2 or greater.

3. An aromatic amine derivative represented by general formula (A'):

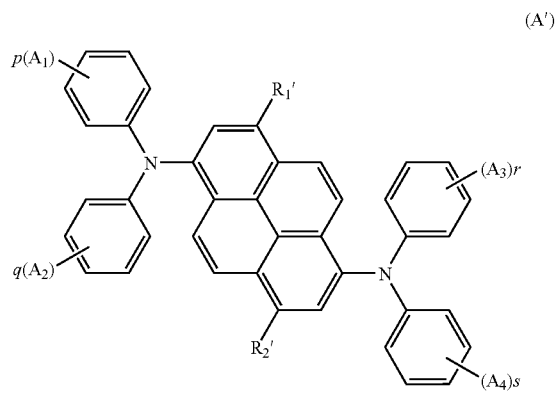

(A')

wherein $R_1'$ and $R_2'$ each independently represents a hydrogen atom or an alkyl group having 1 to 20 carbon atoms; excluding a case where both $R_1'$ and $R_2'$ are hydrogen atoms;

$A_1$, $A_2$, $A_3$ and $A_4$ each independently represents a hydrogen atom, a substituted or unsubstituted alkyl group having 1 to 20 carbon atoms, a substituted or unsubstituted aryl group having 5 to 25 carbon atoms, or a substituted or unsubstituted cycloalkyl group having 3 to 25 carbon atoms;

however, at least one of $A_1$, $A_2$, $A_3$ and $A_4$ bonds to meta-position of a bonding position where a nitrogen atom bonds;

further, a case where any substituent of each group represented by $R_1'$, $R_2'$, $A_1$, $A_2$, $A_3$ and $A_4$ comprises a vinyl group is excluded;

p, q, r and s each independently represents an integer of 1 to 5; when p represents an integer of 2 or greater, each of plural $A_1$ may be the same with, or different from each other, and may bond each other to form a saturated or unsaturated ring; when q represents an integer of 2 or greater, each of plural $A_2$ may be the same with, or different from each other, and may bond each other to form a saturated or unsaturated ring; when r represents an integer of 2 or greater, each of plural $A_3$ may be the same with, or different from each other, and may bond each other to form a saturated or unsaturated ring; and when s represents an integer of 2 or greater, each of plural $A_4$ may be the same with, or different from each other, and may bond each other to form a saturated or unsaturated ring.

4. An aromatic amine derivative represented by general formula (A"):

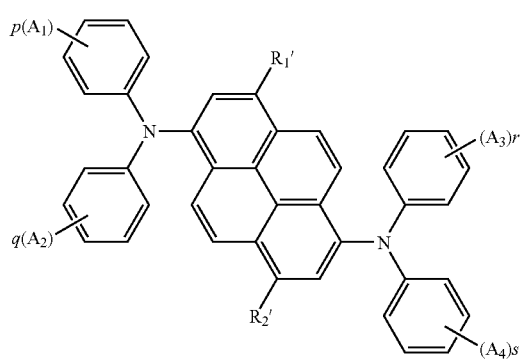

wherein
$R_1'$ and $R_2'$ each independently represents a hydrogen atom or an alkyl group selected from the group consisting of a methyl group, an ethyl group, a propyl group, and an isopropyl group; excluding a case where both $R_1'$ and $R_2'$ are hydrogen atoms;

$A_1, A_2, A_3$ and $A_4$ each independently represents a hydrogen atom, a substituted or unsubstituted alkyl group having 1 to 20 carbon atoms, a substituted or unsubstituted aryl group having 5 to 25 carbon atoms, or a substituted or unsubstituted cycloalkyl group having 3 to 25 carbon atoms;

however, when $A_1, A_2, A_3$ and $A_4$ all represent alkyl groups, a total sum made by adding numbers of carbon atoms in $A_1, A_2, A_3$ and $A_4$ does not exceed 10;

further, a case where any substituent of each group represented by $R_1', R_2', A_1, A_2, A_3$ and $A_4$ comprises a vinyl group is excluded;

p, q, r and s each independently represents an integer of 1 to 5; when p represents an integer of 2 or greater, each of plural $A_1$ may be the same with, or different from each other, and may bond each other to form a saturated or unsaturated ring; when q represents an integer of 2 or greater, each of plural $A_2$ may be the same with, or different from each other, and may bond each other to form a saturated or unsaturated ring; when r represents an integer of 2 or greater, each of plural $A_3$ may be the same with, or different from each other, and may bond each other to form a saturated or unsaturated ring; and when s represents an integer of 2 or greater, each of plural $A_4$ may be the same with, or different from each other, and may bond each other to form a saturated or unsaturated ring.

5. The aromatic amine derivative according to claim 1, which is a doping material for an organic electroluminescence device.

6. An organic electroluminescence device which comprises:
at least one organic thin film layer comprising a light emitting layer sandwiched between a pair of electrodes consisting of an anode and a cathode,
wherein at least one of the at least one organic thin film layer comprises the aromatic amine derivative according to claim 1 singly or as a component of a mixture.

7. The organic electroluminescence device according to claim 6, wherein the at least one organic thin film layer comprises an organic layer having the aromatic amine derivative between the anode and the light emitting layer.

8. The organic electroluminescence device according to claim 6, wherein the light emitting layer contains the aromatic amine derivative in an amount of 0.1 to 20% by weight.

9. The aromatic amine derivative according to claim 1, wherein $R_1$ and $R_2$ are each independently selected from the group consisting of phenyl group, o-biphenyl group, 4-methylphenyl group, α,α-dimethylbenzyl group, 4-cyanophenyl group, 2-phenylethyl group, 1-naphthyl group, and 2-naphthyl group;

$A_1, A_2, A_3$ and $A_4$ are each independently selected from the group consisting of hydrogen atom, methyl group, t-butyl group, isopropyl group, n-propyl group, 2-butyl group, 2-naphthyl group, α,α-dimethylbenzyl group, phenyl group, trifluoromethyl group, and cyclohexyl group; and p, q, r and s each independently represents an integer of 1 to 3, when any of p, q, r and s is 2 or 3, two $A_1, A_2, A_3$ or $A_4$ groups may bond each other to form butane-1,4-diyl group or propane-1,3-diyl group.

10. The aromatic amine derivative according to claim 3, which is a doping material for an organic electroluminescence device.

11. An organic electroluminescence device which comprises:
at least one organic thin film layer comprising a light emitting layer sandwiched between a pair of electrodes consisting of an anode and a cathode,
wherein at least one of the at least one organic thin film layer comprises the aromatic amine derivative according to claim 3 singly or as a component of a mixture.

12. The organic electroluminescence device according to claim 11, wherein the at least one organic thin film layer comprises an organic layer having the aromatic amine derivative between the anode and the light emitting layer.

13. The organic electroluminescence device according to claim 11, wherein the light emitting layer comprises the aromatic amine derivative in an amount of 0.1 to 20% by weight.

14. The aromatic amine derivative according to claim 4, which is a doping material for an organic electroluminescence device.

15. An organic electroluminescence device which comprises:
at least one organic thin film layer comprising a light emitting layer sandwiched between a pair of electrodes consisting of an anode and a cathode,
wherein at least one of the at least one organic thin film layer comprises the aromatic amine derivative according to claim 4 singly or as a component of a mixture.

16. The organic electroluminescence device according to claim 15, wherein the at least one organic thin film layer comprises an organic layer having the aromatic amine derivative between the anode and the light emitting layer.

17. The organic electroluminescence device according to claim 15, wherein the light emitting layer comprises the aromatic amine derivative in an amount of 0.1 to 20% by weight.

* * * * *